United States Patent
Koyuncu et al.

(10) Patent No.: US 12,084,419 B2
(45) Date of Patent: Sep. 10, 2024

(54) CELL METABOLISM MODULATING COMPOUNDS AND USES THEREOF

(71) Applicant: CRESCENTA BIOSCIENCES, Union, NJ (US)

(72) Inventors: Emre Koyuncu, Princeton, NJ (US); Hahn Kim, Princeton, NJ (US)

(73) Assignee: CRESCENTA BIOSCIENCES, Union, NJ (US)

(*) Notice: Subject to any disclaimer, the term of this patent is extended or adjusted under 35 U.S.C. 154(b) by 17 days.

(21) Appl. No.: 17/361,052

(22) Filed: Jun. 28, 2021

(65) Prior Publication Data

US 2022/0002243 A1 Jan. 6, 2022

Related U.S. Application Data

(60) Provisional application No. 63/045,079, filed on Jun. 27, 2020.

(51) Int. Cl.
*C07D 209/86* (2006.01)
*A61K 45/06* (2006.01)

(52) U.S. Cl.
CPC ............ *C07D 209/86* (2013.01); *A61K 45/06* (2013.01); *C07B 2200/07* (2013.01)

(58) Field of Classification Search
CPC ............................. C07D 209/86; A61K 45/06
USPC .......................................................... 514/411
See application file for complete search history.

(56) References Cited

U.S. PATENT DOCUMENTS

| | | | |
|---|---|---|---|
| 3,542,785 A | 11/1970 | William et al. | |
| 3,555,034 A | 1/1971 | Diebold et al. | |
| 3,668,207 A | 6/1972 | William et al. | |
| 4,009,181 A | 2/1977 | Berger et al. | |
| 4,775,680 A * | 10/1988 | Gillard ............ | C07D 209/94 |
| | | | 548/439 |
| 5,522,385 A | 6/1996 | Lloyd et al. | |
| 5,541,196 A | 7/1996 | Fournet et al. | |
| 5,755,218 A | 5/1998 | Johansson et al. | |
| 5,819,726 A | 10/1998 | Rubsamen et al. | |
| 5,855,913 A | 1/1999 | Hanes et al. | |
| 5,906,202 A | 5/1999 | Schuster et al. | |
| 5,957,124 A | 9/1999 | Lloyd et al. | |
| 5,971,951 A | 10/1999 | Ruskewicz | |
| 5,985,309 A | 11/1999 | Edwards et al. | |
| 5,985,320 A | 11/1999 | Edwards et al. | |
| 6,098,620 A | 8/2000 | Lloyd et al. | |
| 6,138,668 A | 10/2000 | Patton et al. | |
| 6,167,880 B1 | 1/2001 | Gonda et al. | |
| 6,228,383 B1 | 5/2001 | Hansen et al. | |
| 6,303,582 B1 | 10/2001 | Eljamal et al. | |
| 6,349,719 B2 | 2/2002 | Gonda | |
| 6,387,390 B1 | 5/2002 | Deaver et al. | |
| 6,408,854 B1 | 6/2002 | Gonda et al. | |
| 6,423,344 B1 | 7/2002 | Platz et al. | |
| 6,427,682 B1 | 8/2002 | Klimowicz et al. | |
| 6,431,167 B1 | 8/2002 | Gonda et al. | |
| 6,447,753 B2 | 9/2002 | Edwards et al. | |

(Continued)

FOREIGN PATENT DOCUMENTS

| | | |
|---|---|---|
| DE | 2431292 A1 | 1/1976 |
| EP | 0307077 A1 | 3/1989 |

(Continued)

OTHER PUBLICATIONS

Masato Furuhashi, et al., Reduction of circulating FABP4 level by treatment with omega-3 fatty acid ethyl esters, Lipids in Health and Disease, 2016, pp. 1-9, 15(5).

Yan Li, et al., Concerted Dynamic Motions of an FABP4 Model and Its Ligands Revealed by Microsecond Molecular Dynamics Simulations, Biochemistry, 2014, pp. 6409-6417, 53.

Heying Pei, et al., Therapeutic potential of a synthetic FABP4 inhibitor 8g on atherosclerosis in ApoE-deficient mice: the inhibition of lipid accumulation and inflammation, RSC Adv., 2016, pp. 52518-52527, 6.

(Continued)

*Primary Examiner* — Kristin A Vajda
(74) *Attorney, Agent, or Firm* — Gearhart Law, LLC

(57) ABSTRACT

A novel class of compounds according to Formula I, II, or III, wherein $W_1$-$W_4$, $Z_1$-$Z_4$, $Z_1$-$Z_5$, X, Y, n, and $R_1$-$R_8$ are as defined in the claims and description of embodiments that bind to fatty acid binding protein FABP4 and modulate adipocyte metabolism to drive enhanced glucose utilization, as well as pharmaceutical compositions comprising the class of compounds, in combination with a pharmaceutically acceptable diluent or carrier, and optionally, further in combination with a therapeutically active agent, and the use of these compounds in medicine and for the preparation of a medicament in the treatment of disorders acting on the FABP4. In examples, the ring Z contains $Z_1$-$Z_4$. In other examples, the ring Z contains $Z_1$-$Z_5$.

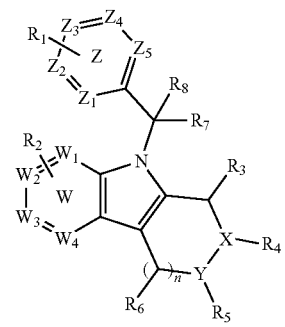

44 Claims, No Drawings

(56) References Cited

U.S. PATENT DOCUMENTS

| | | | |
|---|---|---|---|
| 6,467,476 | B1 | 10/2002 | Ivri et al. |
| 6,503,480 | B1 | 1/2003 | Edwards et al. |
| 6,509,006 | B1 | 1/2003 | Platz et al. |
| 6,540,153 | B1 | 4/2003 | Ivri |
| 6,540,154 | B1 | 4/2003 | Ivri et al. |
| 6,543,443 | B1 | 4/2003 | Klimowicz et al. |
| 6,543,448 | B1 | 4/2003 | Smith et al. |
| 6,546,927 | B2 | 4/2003 | Litherland et al. |
| 6,546,929 | B2 | 4/2003 | Burr et al. |
| 6,550,472 | B2 | 4/2003 | Litherland et al. |
| 7,160,909 | B2 | 1/2007 | Kinnick et al. |
| 7,160,990 | B2 | 1/2007 | Guss et al. |
| 2005/0009817 | A1 | 1/2005 | Savoy et al. |
| 2009/0140448 | A1 | 6/2009 | Aoki et al. |
| 2010/0056377 | A1 | 3/2010 | Nagasawa et al. |
| 2011/0077250 | A1 | 3/2011 | Ryder |
| 2012/0122837 | A1 | 5/2012 | Cheng et al. |
| 2012/0134998 | A1 | 5/2012 | Hotamisligil et al. |
| 2013/0116231 | A1 | 5/2013 | Wilson et al. |
| 2013/0116234 | A1 | 5/2013 | Ceccarelli et al. |
| 2013/0261099 | A1 | 10/2013 | Branchaud et al. |
| 2014/0057900 | A1 | 2/2014 | McKnight et al. |
| 2015/0057326 | A1 | 2/2015 | Wu |
| 2016/0113937 | A1 | 4/2016 | David et al. |
| 2016/0346186 | A1 | 12/2016 | Cotsarelis et al. |
| 2017/0216241 | A1 | 8/2017 | Ojima et al. |
| 2018/0105586 | A1 | 4/2018 | Hotamisligil et al. |

FOREIGN PATENT DOCUMENTS

| | | | | |
|---|---|---|---|---|
| WO | | 1996015111 | A1 | 5/1996 |
| WO | WO | 00/15229 | A1 | 3/2000 |
| WO | WO | 00/15230 | A1 | 3/2000 |
| WO | WO | 00/47734 | A1 | 8/2000 |
| WO | WO | 00/59506 | A1 | 10/2000 |
| WO | WO | 01/54694 | A1 | 8/2001 |
| WO | WO | 02/40448 | A1 | 5/2002 |
| WO | | 2002044152 | A1 | 6/2002 |
| WO | WO- | 2004063156 | A1 * | 7/2004 ........... C07D 209/88 |
| WO | | 2008061671 | A2 | 5/2008 |
| WO | | 2010056631 | A1 | 5/2010 |
| WO | | 2012006612 | A3 | 5/2012 |
| WO | | 2012/139028 | A2 | 10/2012 |
| WO | | 2013062344 | A1 | 5/2013 |
| WO | | 2013189841 | A1 | 12/2013 |
| WO | | 2014029723 | A1 | 2/2014 |
| WO | | 2014040938 | A1 | 3/2014 |
| WO | | 2014093552 | A1 | 6/2014 |
| WO | | 2014146994 | A1 | 9/2014 |
| WO | | 2014177593 | A1 | 11/2014 |
| WO | | 2014/201327 | A1 | 12/2014 |
| WO | | 2014201326 | A1 | 12/2014 |
| WO | | 2016040222 | A1 | 3/2016 |
| WO | | 2016061642 | A1 | 4/2016 |
| WO | | 2017023905 | A1 | 2/2017 |
| WO | | 2017034986 | A1 | 3/2017 |
| WO | | 2017191599 | A1 | 11/2017 |
| WO | | 2017198756 | A1 | 11/2017 |
| WO | | 2018078624 | A1 | 5/2018 |
| WO | | 2018231772 | A1 | 12/2018 |
| WO | | 2019018785 | A2 | 1/2019 |
| WO | | 2021263246 | A1 | 12/2021 |

OTHER PUBLICATIONS

Min Shi, et al., Pharmacological inhibition of fatty acid-binding protein 4 (FABP4) protects against renal ischemia-reperfusion injury, RSC Adv., 2018, pp. 15207-15214, 8.

Yan Wang, et al., Discovery of FDA-Approved Drugs as Inhibitors of Fatty Acid Binding Protein 4 Using Molecular Docking Screening, Journal of Chemical Information and Modeling, 2014, pp. 3046-3050, 54.

Wanhua Lin, et al., BMS309403 Stimulates Glucose Uptake in Myotubes through Activation of AMP-Activated Protein Kinase, PLOS ONE, 2012, pp. 1-8, 7(8).

Holger Kuehne, et al., Design and synthesis of selective, dual fatty acid binding protein 4 and 5 inhibitors, Bioorganic & Medicinal Chemistry Letters, 2016, pp. 5092-5097, 26.

Ge Liu, et al., The natural compound GL22, isolated from Ganoderma mushrooms, suppresses tumor growth by altering lipid metabolism and triggering cell death, Cell Death and Disease, 2018, pp. 1-14.

Sergio Oddi, et al., The anti-inflammatory agent bindarit acts as a modulator of fatty acid-binding protein 4 in human monocytic cells, Scientific Reports, 2019, pp. 1-11.

Mika Hirose, et al., Structure of the human-heart fatty-acid-binding protein 3 in complex with the fluorescent probe 1-anilinonaphthalene-8-sulphonic acid, Journal of Synchrotron Radiation, 2013, pp. 923-928, 20.

Yan Wang, et al., Pimozide, a Novel Fatty Acid Binding Protein 4 Inhibitor, Promotes Adipogenesis of 3T3-L1 Cells by Activating PPARγ, ACS Chemical Neuroscience, 2015, pp. 211-218, 6.

Qinyuan Xu, et al., Design, synthesis and biological evaluation of thiazole- and indole-based derivatives for the treatment of type II diabetes, European Journal of Medicinal Chemistry, 2012, pp. 70-81, 52.

Hisanorj Uehara, et al., Exogenous fatty acid binding protein 4 promotes human prostate cancer cell progression, International Journal of Cancer, 2014, pp. 2558-2568, 135.

Mary Y.K. Lee, et al., Chronic administration of BMS309403 improves endothelial function in apolipoprotein E-deficient mice and in cultured human endothelial cells, British Journal of Pharmacology, 2011, pp. 1564-1576, 162.

Maria J. P. Van Dongen, et al., Structure-Based Screening As Applied to Human FABP4: A Highly Efficient Alternative to HTS for Hit Generation, J. Am. Chem. Soc., 2002, pp. 11874-11880, 124(40).

Ann V. Hertzel, et al., Identification and Characterization of a Small Molecule Inhibitor of Fatty Acid Binding Proteins, Journal of Medicinal Chemistry, 2009, pp. 6024-6031, 52.

William T. Berger, et al., Targeting Fatty Acid Binding Protein (FABP) Anandamide Transporters—A Novel Strategy for Development of Anti-Inflammatory and Anti-Nociceptive Drugs, PLOS ONE, 2012, pp. 1-12, 7(12).

Kantaro Nishigori, et al., Development of a Radioiodinated Triazolopyrimidine Probe for Nuclear Medical Imaging of Fatty Acid Binding Protein 4, PLOS ONE, 2014, pp. 1-10, 9(4).

P. Mosinska, et al., FABP4 blocker attenuates colonic hypomotility and modulates white adipose tissue-derived hormone levels in mouse models mimicking constipation-predominant IBS, Neurogastroenterol Motil, 2018, pp. 1-13, 30(5).

A. L. Bingham et al., Chem. Commun., 603-604 (2001).

Barf et al. "N-Benzyl-indolo carboxylic acids: Design and synthesis of potent and selective adipocyte fatty-acid binding protein (A-FABP) inhibitors", Bioorganic & Medicinal Chemistry Letters. 2009. 19, pp. 1745-1748, especially: p. 1745, col. 1, para 2; p. 1747, Table 2, Compound 18.

CAS Registry No. 116475-42-4, Sep. 25, 1988 (Year: 1988).

CAS Registry No. 2129127-97-3, Sep. 22, 2017 (Year: 2017).

CAS Registry No. 2440468-27-0, Jul. 3, 2020 (Year: 2020).

Conrad, Maker of Immune Actiation in COVID-19, retrieved from https://medicine.osu.edu/news/marker-of-immune-activation-in-covid-19 Feb. 1, 2021.

Dutta et al. Int. J. Mol. Sci. 2019, 20, 644; Curbing Lipids: Impacts ON Cancer and Viral Infection (Year: 2019).

Dyall et al. Antimicrobial Agents and Chemotherapy, 2014, vol. 58 No. 8, p. 4885-4893 (Year: 2014).

Escote et al. "A study of fatty acid binding protein 4 in HIV-1 infection and in combination antiretroviral therapy-related metabolic disturbances and lipodystrophy", HIV Medicine, 2011, 12, pp. 428-437, especially: abstract.

Flynn et al. "Correlation and Prediction of Mass Transport across Membranes I: Influence of Alkyl Chain Length on Flux-Determining Properties of Barrier and Diffusant", Journal of Pharmaceutical Sciences. 1972. vol. 61, No. 6, pp. 838-852, especially: p. 843, col. 2, para 2.

Hotamisligil et al., Science. Nov. 22, 1996;274(5291):1377-9.

(56) References Cited

OTHER PUBLICATIONS

Hu and Qiao, Endocrine. Oct. 2011;40(2):196-202.
Jones Keith, Roset Xavier, Rossiter Sharon, Whitfield Philip: "Demethylation of 2,4-dimethoxyquinolines: the synthesis of atanine", Organic & Biomolecular Chemistry, England, Dec. 4, 2003 (Dec. 4, 2003), England, pp. 4380-4383, XP055898196, Retrieved from the Internet <URL:https://pubs.rsc.org/en/content/articlepdf/2003/ob/b311281k> [retrieved on Mar. 7, 2022], DOI: 10.1039/b311281k.
Kay, David et al., Synthesis of 2-aminomethylene-1,2-dihydroimidazo[1,2-a] quinolin-1-ones, Chemistry and Industry, 1988, pp. 94-95.
Kuhne et al., Bioorg Med Chem Lett. Oct. 15, 2016;26(20):5092-5097.
Lan et al., J Lipid Res. Apr. 2011;52(4):646-56.
Lepre et al. "Theory and Applications of NMR-Based Screening in Pharmaceutical Research", Chem. Rev. 2004. vol. 104, pp. 3641-3675, especially: p. 3666, col. 2, para 3; p. 3669, col. 2, para 2.
Makowski et al., Nat Med. Jun. 2001; 7(6): 699-705.
Mansoor et al. "2-ethylpyridine, a cigarette smoke component, causes mitochondrial damage in human retinal pigment epithelial cells in vitro", Indian J Ophthalmol. 2014. vol. 62(1), p. 1622, especially: abstract; p. 2, para 3.
Masanori Tayu et al., Org. Biomol. Chem. (2013) 11 496.
Pubchem CID 110167588 (Year 2016).
PubChem CID 1264779 (Year: 2005).
Pubchem CID 15270263 (Year 2007).
PubChem CID 398603831 (2009).
PubChem CID 68577135 (Year: 2012).
PubChem CID 82577974 (Year: 2014).
PubChem CID 83835851 (Year: 2014).
PubChem CID 2729601 (Year: 2009).
PubChem CID 24847096 (Year: 2018).
Saksi et al., Circ Cardiovasc Genet. Oct. 2014;7(5):588-98.
Sanders et al. ,JAMA. 2020;323(18):1824-1836, doi: 10.1001/jama.2020.6019, published on line Apr. 13, 2020, (Year: 2020).
Sarangi et al. Diagnosis, prevention, and treatment of corona-virus disease: a review. Expert Review of Anti-infective therapy 2021, 1944103.
Schmidt P. et al., Heilmittelchemische Studien in der heterocyclischen Reihe. 22. Mitteilung. Pyrazolo-pyrimidine, Helvitica Chimica Acta, vol. 41, Issue4 1958 pp. 1052-1060.
Shaughnessy et al., Diabetes Jun. 2000; 49(6): 904-911.
Shum et al., J Clin Invest. Aug. 2006; 116(8):2183-2192.
Sokolowski et al. Effects of non-steroidal anti-inflammatory drugs and other eicosanoids consensus report in times of COVD-19. Preprint on Authorea, 1-28, Nov. 26, 2021.
Sulsky et al., Bioorg Med Chem Lett. Jun. 15, 2007;17(12):3511-5.
Tagami et al., ACS Med Chem Lett. Apr. 14, 2016; 7(4): 435-439.
Tuncman et al., Proc Natl Acad Sci U S A. May 2, 2006;103(18):6970-5.
Vannelli et al.: "The Antituberculosis Drug Ethionamide Is Activated by a Flavoprotein Monooxygenase", The Journal of Biological Chemistry, vol. 277, No. 15, 2002, pp. 12824-12829, XP002283431, DOI: 10.1074/jbc.M110751200.
Wang et al., Oncotarget. Apr. 5, 2016;7(14):18984-98.
Yan et al., Placenta. Mar. 2016;39:94-100.
Zhu et al. "From SARS and MERS to CoVID-19: a brief summary and comparison of severe acute respiratory infections caused by three highly pathogenic human coronavirus," Respiratory Research, 2020 21 :224 https://doi.org/10.1186/s12931-020-01479-w (Year: 2020).
International Search Report & Written Opinion received for PCT Appl. No. PCT/US21/40584, mailed on Dec. 10, 2021, 10 pages.
International Preliminary Report on Patentability received for PCT Application No. PCT/US2021/014250, mailed on Jun. 9, 2021, 8 pages.
International Search Report received for PCT Application No. PCT/US2021/014250, mailed on Jun. 9, 2021, 4 pages.
International Preliminary report of Patentability received for PCT Appl. No. PCT/US21/40588, mailed on Jan. 10, 2023, 10 pages.
International Search Report received for PCT Application No. PCT/US21/40588, mailed on Dec. 7, 2021, 6 pages.
Constance E. Runyan, et al., Impaired phagocytic function in CX3CR1+ tissue-resident skeletal muscle macrophages prevents muscle recovery after influenza A virus-induced pneumonia in old mice, Aging Cell, 2020, pp. 1-20, 19.
Hibah Shaath, et al., Single-Cell Transcriptome Analysis Highlights a Role for Neutrophils and Inflammatory Macrophages in the Pathogenesis of Severe COVID-19, Cells, 2020, pp. 1-19, 9, 2374.
Dylan Sheerin, et al., Systematic evaluation of transcriptomic disease risk and diagnostic biomarker overlap between COVID-19 and tuberculosis: a patient-level meta-analysis, medRxiv, 2020, pp. 1-26.
Rajnish Kumar Singh, et al., HIF1α-Regulated Expression of the Fatty Acid Binding Protein Family Is Important for Hypoxic Reactivation of Kaposi's Sarcoma-Associated Herpesvirus, J. Virol., 2021, pp. e02063-20, 95(12).
Johan Smith, et al., An overview of acute lung injury in general and in particular viral infections with specific reference to nebulized surfactant and anticoagulation, Journal of Respiratory Diseases and Medicine, 2020, pp. 1-27, 2.
Chiao-Fang Teng, et al., A biphasic response pattern of lipid metabolomics in the stage progression of hepatitis B virus X tumorigenesis, Molecular Carcinogenesis, 2016, pp. 105-114, 55(1).
Prasad Tongaonkar, et al., RTD-1 therapeutically normalizes synovial gene signatures in rat autoimmune arthritis and suppresses proinflammatory mediators in RA synovial fibroblasts, Physiol. Genomics, 2019, pp. 657-667, 51(12).
Miguel A. Vega, et al., MAFB and MAF Transcription Factors as Macrophage Checkpoints for COVID-19 Severity, Front. Immunol., 2020, pp. 1-9, 11.
Li Wang, et al., Novel gene-specific translation mechanism of dysregulated, chronic inflammation reveals promising, multifaceted COVID-19 therapeutics, bioRxiv, 2020, pp. 1-36.
Jun Wu, et al., Immunity-and-matrix-regulatory cells derived from human embryonic stem cells safely and effectively treat mouse lung injury and fibrosis, Cell Research, 2020, pp. 794-809, 30.
Gang Xu, et al., The differential immune responses to COVID-19 in peripheral and lung revealed by single-cell RNA sequencing, Cell Discovery, 2020, pp. 1-14, 6:73.
Dan Zhang, et al., COVID-19 infection induces readily detectable morphologic and inflammation-related phenotypic changes in peripheral blood monocytes, J. Leukoc. Biol., 2020, pp. 1-10.
Ji-Yuan Zhang, et al., Single-cell landscape of immunological responses in patients with COVID-19, Nature Immunology, 2020, pp. 1107-1118, 21.
Bin Zhang, et al., CD127 imprints functional heterogeneity to diversify monocyte responses in human inflammatory diseases, bioRxiv, 2020, pp. 1-34.
Yuanqi Gong, et al., FABP4 inhibitors suppress inflammation and oxidative stress in murine and cell models of acute lung injury, Biochemical and Biophysical Research Communications, 2018, pp. 1115-1121, 496.
Yooju Jung, et al., Functional inhibition of fatty acid binding protein 4 ameliorates impaired ciliogenesis in GCs, Biochemical and Biophysical Research Communications, 2021, pp. 28-33, 539.
Tjeerd Barf, et al., N-Benzyl-indolo carboxylic acids: Design and synthesis of potent and selective adipocyte fatty-acid binding protein (A-FABP) inhibitors, Bioorganic & Medicinal Chemistry Letters, 2009, pp. 1745-1748, 19.
Rune Ringom, et al., Substituted benzylamino-6-(trifluoromethyl)pyrimidin-4(1H)-ones: a novel class of selective human A-FABP inhibitors, Bioorganic & Medicinal Chemistry Letters, 2004, pp. 4449-4452, 14.
Fredik Lehmann, et al., Discovery of inhibitors of human adipocyte fatty acid-binding protein, a potential type 2 diabetes target, Bioorganic & Medicinal Chemistry Letters, 2004, pp. 4445-4448, 14.
Haiyan Cai, et al., Discovery of highly selective inhibitors of human fatty acid binding protein 4 (FABP4) by virtual screening, Bioorganic & Medicinal Chemistry Letters, 2010, pp. 3675-3679, 20.
Masato Furuhashi, et al., Fatty acid-binding proteins: role in metabolic diseases and potential as drug targets, Nature Reviews Drug Discovery, 2008, pp. 489-503, 7.

(56) References Cited

OTHER PUBLICATIONS

Xiujie Liu, et al., New aromatic substituted pyrazoles as selective inhibitors of human adipocyte fatty acid-binding protein, Bioorganic & Medicinal Chemistry Letters, 2011, pp. 2949-2952, 21.
Yoko Beniyama, et al., Structure-guided design, synthesis and in vitro evaluation of a series of pyrazole-based fatty acid binding protein (FABP) 3 ligands, Bioorganic & Medicinal Chemistry Letters, 2013, pp. 1662-1666, 23.
An Cheng, et al., Development of FABP3 ligands that inhibit arachidonic acid-induced α-synuclein oligomerization, Brain Research, 2019, pp. 190-197.
Holger Kuehne, et al., Design and synthesis of selective, dual fatty acid binding protein 4 and 5 inhibitors, Bioorganic & Medicinal Chemistry Letters, 2016, pp. 5092-5097, 26(20).
Kazuya Matsuo, et al., Inhibition of MPTP-induced α-synuclein oligomerization by fatty acid binding protein 3 ligand in MPTP-treated mice, Neuropharmacology, 2019, pp. 164-174.
Haiyan Cai, et al., Novel fatty acid binding protein 4 (FABP4) inhibitors: Virtual screening, synthesis and crystal structure determination, European Journal of Medicinal Chemistry, 2015, pp. 241-250, 90.
Yang Zhou, et al., The discovery of novel and selective fatty acid binding protein 4 inhibitors by virtual screening and biological evaluation, Bioorganic & Medicinal Chemistry, 2016, pp. 4310-4317, 24.
Alba Bosquet, et al., FABP4 inhibitor BMS309403 decreases saturated-fatty-acid-induced endoplasmic reticulum stress-associated inflammation in skeletal muscle by reducing p38 MAPK activation, BBA—Molecular and Cell Biology of Lipids, 2018, pp. 604-613, 1863.
Yuta Okamura, et al., Vasculo-protective effect of BMS-309403 is independent of its specific inhibition of fatty acid-binding protein 4, Pflugers Arch—Eur. J. Physiol., 2017, pp. 1-12.
Toshihiko Okada, et al., Synthesis of BMS-309403-Related Compounds, Including [14C]BMS-309403, a Radioligand for Adipocyte Fatty Acid Binding Protein, Chem. Pharm. Bull, 2012, pp. 164-168, 60(1).
Hong Lan, et al., Small-molecule inhibitors of FABP4/5 ameliorate dyslipidemia but not insulin resistance in mice with diet-induced obesity, Journal of Lipid Research, 2011, pp. 646-656, 52.
International Search Report and Written Opinion of the International Searching Authority dated Oct. 27, 2021 for PCT/US21/39740, pp. 1-17.
Masato Furuhashi, et al., Lipid Chaperones and Metabolic Inflammation, International Journal of Inflammation, 2011, pp. 1-13.
Ding-Ding Gao, et al., From hit to lead: Structure-based discovery of naphthalene-1-sulfonamide derivatives as potent and selective inhibitors of fatty acid binding protein 4, European Journal of Medicinal Chemistry, 2018, pp. 44-59, 154.
Giuseppe Floresta, et al., 3D-QSAR assisted identification of FABP4 inhibitors: An effective scaffold hopping analysis/QSAR evaluation, Bioorganic Chemistry, 2019, pp. 276-284, 84.
Giuseppe Floresta, et al., Adipocyte fatty acid binding protein 4 (FABP4) inhibitors. A comprehensive systematic review, European Journal of Medicinal Chemistry, 2017, pp. 854-873, 138.
Thereza Cristina Lonzetti Bargut, et al., Eicosapentaenoic acid (EPA) vs. Docosahexaenoic acid (DHA): Effects in epididymal white adipose tissue of mice fed a high-fructose diet, Prostaglandins, Leukotrienes and Essential Fatty Acids, 2017, pp. 14-24, 123.
Min Shi, et al., Pharmacological inhibition of fatty acid-binding protein 4 alleviated kidney inflammation and fibrosis in hyperuricemic nephropathy, European Journal of Pharmacology, 2020, pp. 1-9, 887.
Yu-Long He, et al., Development of FABP4/5 inhibitors with potential therapeutic effect on type 2 Diabetes Mellitus, European Journal of Medicinal Chemistry, 2021, pp. 1-14, 224.
Hao-Chi Hsu, et al., The Antinociceptive Agent SBFI-26 Binds to Anandamide Transporters FABP5 and FABP7 at Two Different Sites, Biochemistry, 2017, pp. 3454-3462, 56.
Ewgenij Proschak, et al., Opportunities and Challenges for Fatty Acid Mimetics in Drug Discovery, Journal of Medicinal Chemistry, 2017, pp. 5235-5266, 60.
Haixia Su, et al., Exploration of Fragment Binding Poses Leading to Efficient Discovery of Highly Potent and Orally Effective Inhibitors of FABP4 for Anti-inflammation, Journal of Medicinal Chemistry, 2020, pp. 4090-4106, 63(8).
Bernd Kuhn, et al., A Real-World Perspective on Molecular Design, Journal of Medicinal Chemistry, 2016, pp. 4087-4102, 59(9).
Uno Tagami, et al., Interaction Analysis of FABP4 Inhibitors by X-ray Crystallography and Fragment Molecular Orbital Analysis, ACS Med. Chem. Lett., 2016, pp. 435-439, 7(4).
Hai-Yan Cai, et al., Benzbromarone, an old uricosuric drug, inhibits human fatty acid binding protein 4 in vitro and lowers the blood glucose level in db/db mice, Acta Pharmacologica Sinica, 2013, pp. 1387-1402, 34.
A. W. Zimmerman, et al., New insights into the structure and function of fatty acid-binding proteins, Cell. Mol. Life Sci., 2002, pp. 1096-1116, 59.
Christiane Look, et al., BMS309403 directly suppresses cardiac contractile function, Naunyn-Schmiedeberg's Arch Pharmacol, 2011, pp. 255-263, 384.
Gordon S. Lee, et al., Fatty Acid Binding Proteins Expressed at theHuman Blood-Brain Barrier Bind Drugs in an Isoform-Specific Manner, Pharm. Res., 2015, pp. 3432-3446, 32.
S. M. Berge, et al., Pharmaceutical salts, J. Pharm. Sci., 1977, pp. 1-19, 66(1).
Philip L. Gould, Salt selection for basic drugs, International Journal of Pharmaceutics, 1986, pp. 201-217, 33 (1-3).
Mino R. Caira, et al., Preparation and crystal characterization of a polymorph, a monohydrate, and an ethyl acetate solvate of the antifungal fluconazole, Journal of Pharmaceutical Sciences, 2004, pp. 601-611, 93(3).
Elsa C. Van Tonder, et al., Preparation and physicochemical characterization of 5 niclosamide solvates and 1 hemisolvate, AAPS PharmSciTech, 2004, pp. 1-10, 5(1).
Ann Bingham, et al., delta-Sulfanilamide, Acta Crystallographica Section C Crystal Structure Communications, 2008, pp. 205-207, C64.
Hans Bundgaard, Design of Prodrugs, 1985, Oxford : Elsevier, Amsterdam; New York.
V. Stella, Pro-drugs: An Overview and Definition, ACS Symposium Series, vol. 14, 1975, pp. 1-115, Chapter 1.
Giorgio Bertolini, et al., A New Rational Hypothesis for the Pharmacophore of the Active Metabolite of Leflunomide, a Potent Immunosuppressive Drug, J. Med. Chem., 1997, pp. 2011-2016, 40(13).
D. Shan, et al., Prodrug strategies based on intramolecular cyclization reactions, J. Pharm. Sci, 1997, pp. 765-767, 86(7).
Kenneth D. Bagshawe, Antibody-directed enzyme prodrug therapy: A review, Drug Development Research, 1995, pp. 220-230, 34(2).
Thorsteinn Loftsson, et al., The pharmacokinetics and transdermal delivery of loteprednol etabonate and related soft steroids, Advanced Drug Delivery Reviews, 1994, pp. 293-299, 14(2-3).
R. Ferroni, et al., Cyclic guanidines: synthesis and antiplatelet activity of 4,6,7,8-tetrahydro-1H-imidazo[1,2-a]pyrazolo[3,4-d]pyrimidin-7-ones and 1,4,6,7,8,9-hexahydropyrazolo[3',4':4,5]pyrimido[2,1-c] [1,2,4]triazin-7-ones, Arzneimittelforschung, 1990, pp. 1328-1331, 40(12).
T. Iwaoka, et al., Determination of (+)- and (−)-nicardipine concentrations in human serum and their correlation with the antihypertensive effect after oral administration of racemic nicardipine, European Journal of Clinical Pharmacology, 1995, pp. 345-349, 48.
C. H. Lochmueller, et al., Chromatographic resolution of enantiomers selective review, J. Chromatogr., 1975, pp. 283-302, 113(3).
Peyton Jacob III, Resolution of (+/−)-5-bromornicotine. Synthesis of (R)- and (S)-nornicotine of high enantiomeric purity, J. Org. Chem., 1982, pp. 4165-4167, 47(21).
Antoine Fakhry Abdelmassih, et al., Single cell sequencing unraveling genetic basis of severe COVID19 in obesity, Obes. Med., 2020, 20:100303.

(56) References Cited

OTHER PUBLICATIONS

Srinivasa Reddy Bonam, et al., Adjunct Immunotherapies for the Management of Severely Ill COVID-19 Patients, Cell Reports Medicine, 2020, 100016, 1(2).

Pierre Bost, et al., Host-Viral Infection Maps Reveal Signatures of Severe COVID-19 Patients, Cell, 2020, pp. 1475-1488, 181(7).

Blai Coll, et al., The fatty acid binding protein-4 (FABP4) is a strong biomarker of metabolic syndrome and lipodystrophy in HIV-infected patients, Atherosclerosis, 2008, pp. 147-153, 199(1).

Christophe Desterke, et al., PPARγ Cistrome Repression during Activation of Lung Monocyte-Macrophages in Severe COVID-19, iScience, 2020, p. 101611, 23(10).

Prashant Dogra, et al., Innate Immunity Plays a Key Role in Controlling Viral Load in COVID-19: Mechanistic Insights from a Whole-Body Infection Dynamics Model, ACS Pharmacol. Transl. Sci., 2021, pp. 248-265, 4(1).

Marat Fudim, et al., Implications for Neuromodulation Therapy to Control Inflammation and Related Organ Dysfunction in COVID-19, Journal of Cardiovascular Translational Research, 2020, pp. 894-899, 13.

Luis F> Garcia, Immune Response, Inflammation, and the Clinical Spectrum of COVID-19, Front. Immunol., 2020, pp. 1-13, vol. 11.

Anne Geller, et al., Could the Induction of Trained Immunity by B-Glucan Serve as a Defense Against COVID-19?, Front. Immunol., 2020, pp. 1-11, vol. 11.

Lara Gibellini, et al., Different origin of adipogenic stem cells influences the response to antiretroviral drugs, Experimental Cell Research, 2015, pp. 160-169, 337(2).

Lisa Giovannini-Chami, et al., The 'one airway, one disease' concept in light of Th2 inflammation, Eur. Respir. J., 2018, pp. 1-12, vol. 52.

Jean-Baptiste Gorin, et al., Plasma FABP4 is associated with liver disease recovery during treatment-induced clearance of chronic HCV infection, Sci. Rep., 2020, pp. 1-10, vol. 10.

Monika Bociaga-Jasik, et al., Metabolic complications and selected cytokines in HIV-infected individuals, Polskie Archiwum Medycyny Wewnetrznej, 2014, pp. 26-35, 124 (1-2).

Rogan A. Grant, et al., Alveolitis in severe SARS-CoV-2 pneumonia is driven by self-sustaining circuits between infected alveolar macrophages and T cells, bioRXiv, 2020, pp. 1-33.

Masha Hajivalili, et al., Gaining insights on immune responses to the novel coronavirus, COVID-19 and therapeutic challenges, Life Sci., 2020, pp. 1-12, vol. 257.

Aaron W. James, et al., Lentiviral Delivery of PPARγ shRNA Alters the Balance of Osteogenesis and Adipogenesis, Improving Bone Microarchitecture, Tissue Eng. Part A., 2014, pp. 2699-2710, 20(19-20).

Yan Jiang, et al., Exploring the mechanism of Shengmai Yin for coronary heart disease based on systematic pharmacology and chemoinformatics, Bioscience Reports, 2020, pp. 1-24, 40(6).

Yong-Jiu Jin, et al., Identification of a Novel Binding Site Between HIV Type 1 Nef C-Terminal Flexible Loop and AP2 Required for Nef-Mediated CD4 Downregulation, AIDS Res. Hum. Retroviruses, 2013, pp. 725-731, 29(4).

Ashley L. St. John, et al., Early insights into immune responses during COVID-19, J. Immunol., 2020, pp. 555-564, 205.

Leila Mohamed Khosroshahi, et al., Dysregulation of the immune response in coronavirus disease 2019, Cell Biology International, 2020, pp. 1-6.

Anna Klinke, et al., Emerging therapies for right ventricular dysfunction and failure, Cardiovasc. Diagn. Ther., 2020, pp. 1735-1767, 10(5).

Minfeng Liao, et al., The landscape of lung bronchoalveolar immune cells in COVID-19 revealed by single-cell RNA sequencing, Nature Medicine, 2020, pp. 842-844, 26.

Zhongshun Liu, et al., Histone Deacetylase Inhibitor SAHA Induces Expression of Fatty Acid-Binding Protein 4 and Inhibits Replication of Human Cytomegalovirus, Virol. Sin., 2021, pp. 1352-1362, 36(6).

Yu Liu, et al., The roles of PPARγ and its agonists in autoimmune diseases: A comprehensive review, J. Autoimmun., 2020, pp. 1-12.

Jinglu Lyu, et al., Reflection on lower rates of COVID-19 in children: Does childhood immunizations offer unexpected protection?, Med. Hypotheses, 2020, 143.

Lucy MacDonald, et al., COVID-19 and Rheumatoid Arthritis share myeloid pathogenic and resolving pathways, bioRxiv, pp. 1-29, 2020.

L. Lamara Mahammed, et al., Immunopathological mechanisms in SARS-CoV-2 infection, ASJP, 2019, pp. 2453-3555, 5(1).

Patrick W. G. Mallon, et al., Effect of Rosiglitazone on Peroxisome Proliferator-Activated Receptor γ Gene Expression in Human Adipose Tissue Is Limited by Antiretroviral Drug-Induced Mitochondrial Dysfunction, The Journal of Infectious Diseases, 2008, pp. 1794-1803, 198(12).

Roberta Goncalves Marangoni, et al., Adipocytic Progenitor Cells Give Rise to Pathogenic Myofibroblasts: Adipocyte-to-Mesenchymal Transition and Its Emerging Role in Fibrosis in Multiple Organs, Current Rheumatology Reports, 2020, pp. 1-8, 22:79.

Pierre S. Maximus, et al., Adipocytokines: Are they the Theory of Everything?, Cytokine, 2020, pp. 1-11.

Mario Luca Morieri, et al., Adipokines levels in HIV infected patients: lipocalin-2 and fatty acid binding protein-4 as possible markers of HIV and antiretroviral therapy-related adipose tissue inflammation, BMC Infect. Dis., 2018, pp. 1-9, 18:10.

Leo Nicolai, et al., Vascular neutrophilic inflammation and immunothrombosis distinguish severe COVID-19 from influenza pneumonia, J. Thromb. Haemost., 2020, pp. 1-8.

Youdong Pan, et al., Survival of tissue-resident memory T cells requires exogenous lipid uptake and metabolism, Nature, 2017, pp. 252-256, 543(7644).

Gaetano Zirro, et al., Imperfect storm: is interleukin-33 the Achilles heel of COVID-19?, Lancet. Rheumatol, 2020, pp. e779-e790, 2(12).

Ivon Johanna Rodriguez, et al., Human immune response to SARS-CoV-2: What is known? A scoping review, Infectio, 2020, pp. 26-35, 24(3).

\* cited by examiner

CELL METABOLISM MODULATING COMPOUNDS AND USES THEREOF

CROSS-REFERENCE TO RELATED APPLICATIONS SECTION

This application claims priority to U.S. Provisional Patent Application Ser. 63/045,079 filed on Jun. 27, 2020, the entire contents of which are hereby incorporated by reference in their entirety.

FIELD OF THE EMBODIMENTS

This invention relates to novel compounds for treatment or prophylaxis of diseases related to metabolism and inflammation, including, but not limited to, type-2 diabetes, obesity, cardiovascular disease, asthma, cancer and other diseases. Compounds in this invention particularly interact with fatty acid binding protein (FABP) 4 and improve glucose consumption in adipocytes.

BACKGROUND OF THE EMBODIMENTS

FABPs are a family of proteins that reversibly bind free fatty acids and other lipid molecules and facilitate their transport in cells. To date, nine different FABP isoforms have been identified in mammals. FABP isoforms display differential expression patterns in different tissues. Fatty acid binding protein 4 (FABP4), also often referred to as aP2 in literature, is primarily expressed in adipocytes and macrophages, and mediates key metabolic and inflammatory pathways in these cells such as lipid storage and degradation, signaling and eicosanoid production. In addition, FABP4 is also secreted to plasma and has been proposed to act as an adipose-derived factor regulating systemic glucose homeostasis.

Genetic knockout studies in mice provided insights into tissue-specific and systemic functions of FABP4. Importantly, when mice bearing a homozygous deletion of the FABP4 gene subjected to prolonged high-fat diet they gained weight comparable to wild-type but were protected from hyperglycemia and insulin-resistance (Hotamisligil et al., Science. 1996 Nov. 22; 274(5291):1377-9). In addition, FABP4-deficiency significantly protected apolipoprotein E (ApoE) knockout mice from atherosclerosis, a phenotype attributed to FABP4 modulation of inflammatory pathways in macrophages (Makowski et al., Nat Med. 2001 June; 7(6): 699-705). FABP4 expression has also been detected in airway epithelial cells and FABP4-deficiency was demonstrated to be protective in a mice mouse model of allergic lung inflammation (Shum et al., J Clin Invest. 2006 August; 116(8):2183-2192).

Several reports have been published in literature linking FABP4 expression level and functions with a number of pathologies in humans. For instance, reduced risk of type-2 diabetes and coronary heart disease was observed in individuals bearing genetic variations in the promoter region of FABP4 (rs77878271) that result in reduced expression of this gene (Tuncman et al., Proc Natl Acad Sci USA. 2006 May 2; 103(18):6970-5). Same polymorphism was also associated with reduced atherosclerotic disease manifestations in an independent study (Saksi et al., Circ Cardiovasc Genet. 2014 October; 7(5):588-98). Furthermore, triple-negative breast cancer patients with a single nucleotide polymorphism in the 3' untranslated region (UTR) of FABP4 (rs1054135-GG genotype) that also results in reduced FAB4 expression was associated with reduced risk of disease progression and a prolonged disease-free survival time (Wang et al., Oncotarget. 2016 Apr. 5; 7(14):18984-98). Increased expression of FABP4 has been observed in preeclamptic placenta and proposed to have a role in the pathogenesis of preeclampsia (Yan et al., Placenta. 2016 March; 39:94-100). Similarly, granulosa cells of polycystic ovary syndrome patients also show increased FABP4 expression and this was related to the clinical characterization of the disease (Hu and Qiao, Endocrine. 2011 October; 40(2):196-202). Collectively, these studies demonstrated the active role of FAPB4 in regulating systemic metabolism and inflammation, and suggested that pharmacological targeting of FABP4 can be used as a strategy for the treatment of a variety of diseases linked to FABP4 functions.

Adipocytes play a central role in the systemic glucose homeostasis. One of their primary roles is taking up excess glucose in plasma and storing it in the form of lipids. Adipocyte dysfunction due to metabolic stress and inflammation often leads to complications such as hyperglycemia and insulin resistance. It is noteworthy that FABP4-deficient mice showed increased glucose deposition to adipose tissue. Adipocytes isolated from these animals showed significantly elevated rate of glucose conversion into fatty acids compared to their wild-type counterparts. (Shaughnessy et al., Diabetes 2000 June; 49(6): 904-911). Thus, increasing glucose consumption in adipocytes can be achieved by targeting FABP4.

While the literature and certain prior art patent applications (e.g., WO 00/47734, WO 00/15229, WO 00/15230, WO 02/40448, WO 01/54694, WO 00/59506 and WO 2004/063156) have provided various presentations of the concept of the FABP inhibition, in general, and that of the FABP4 inhibition, in particular, none of the discussions in these prior art documents provides solution(s) of all of the unmet needs, as does the present invention. Specifically, the present invention describes a novel class of compounds that bind to FABP4 and modulate adipocyte metabolism to drive enhanced glucose utilization.

SUMMARY OF THE EMBODIMENTS

The present invention, in one of its embodiments, relates to a compound of Formula (I):

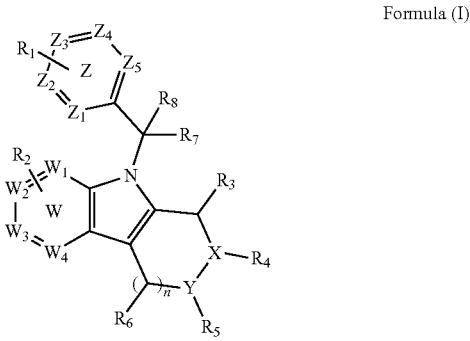

Formula (I)

Wherein:
$W_{1-4}$ and $Z_1$-$Z_5$ are each independently —C, —CH, $CH_2$, O, S, or N;
X is independently $CH_2$, N or $CHR_4$;
Y is independently $CH_2$, or $CHR_5$;
n is a number between 0 and 3;

One or more $R_1$'s on the ring Z are independently selected from the group consisting of: CN, OH, COOH, $OCH_3$, $CF_3$, $CONH_2$, $B(OH)_2$, $B(OR)_2$, an acid isostere, a substituted amine, ethers, and a halogen, substituted or unsubstituted alkyl, substituted or unsubstituted cyclic or heterocyclic, substituted or unsubstituted cycloaryl or cychloheteroaryl, wherein the substituted cycloaryl or cychloheteroaryl may be substituted with hydrogen, CN, OH, COOH, $OCH_3$, $CF_3$, $CONH_2$, $B(OH)_2$, $B(OR)_2$, an acid isostere, a substituted amine, ethers, and a halogen, substituted or unsubstituted alkyl, substituted or unsubstituted cyclic or heterocyclic, substituted or unsubstituted cycloaryl or cychloheteroaryl, $SO_2NH_2$;

One or more $R_2$'s on the ring W are independently selected from the group consisting of: CN, OH, CHF2, CH2F, $CF_3$, COOH, $CONH_2$, $B(OH)_2$, $B(OR)_2$, an acid isostere, a halogen, and a bicyclic heteroaryl;

$R_7$ is hydrogen or CN, COOH, $CONH_2$, $B(OH)_2$, $B(OR)_2$ or an acid isostere;

R is alkyl;

$R_3$, $R_4$, $R_5$ or $R_8$, or $R_6$ when n is not zero, is each independently selected from:
(1) hydrogen;
(2) alkyl or ether having 1 to 12 carbon atoms,
(3) a substituted amine, or
(4) —$(CH_2)_m$ G, wherein m is 1 to 12 and G is independently selected from:
  (a) cycloalkyl containing 3 to 6 carbon atoms,
  (b) aryl or heteroaryl,
  (c) $CF_3$, $CF_2H$ or $CFH_2$, or
  (d) a heterocycle,
provided that $R_3$, $R_4$, $R_5$, $R_8$, or $R_6$ are not all hydrogen;
or pharmaceutically acceptable salts or stereoisomers thereof.

It is an object of the present invention is the compound according to Formula (I), (II), or (III) for use in the treatment of disorders acting on the fatty acid binding protein (FABP4).

Yet another object of the present invention is a pharmaceutical composition comprising a compound according to Formula (I), (II), or (III) as active ingredient, in combination with a pharmaceutically acceptable diluent or carrier for use in the treatment of disorders acting on the FABP4. Here, the pharmaceutical composition can further comprise an additional therapeutically active agent.

Yet another object of the present invention is a method for the treatment of disorders acting on the FABP4, which comprises administering to a subject in need of such treatment (preferably, a human) an effective amount of a compound according to Formula (I), (II), or (III) including, optionally, the co-administration with other therapeutic agents, either as a single (or multiple) dosing, and either simultaneously or sequentially.

Yet another object of the present invention is a method for inhibiting FABP4, which comprises administering to a subject in need of such treatment (preferably, a human) an effective amount of a compound according to Formula (I), (II), or (III).

Yet another object of the present invention is the use of a compound according to Formula (I), (II), or (III) for the manufacture of a medicament for use in the treatment of disorders acting on the fatty acid binding protein FABP4. Examples of such disorders include type 2 diabetes, hyperglycemia, metabolic syndrome, obesity, atherosclerosis, intracranial atherosclerotic disease, non-alcoholic steatohepatitis, asthma, vascular dementia, multiple sclerosis, Alzheimer's disease, other chronic inflammatory and autoimmune/inflammatory diseases, chronic heart disease, polycystic ovary syndrome, preeclampsia, and cancer.

Other features and advantages of the invention will be apparent from the detailed description and the claims.

DESCRIPTION OF THE PREFERRED EMBODIMENTS

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be.

The invention, in one embodiment, is a compound of Formula (I) comprising:

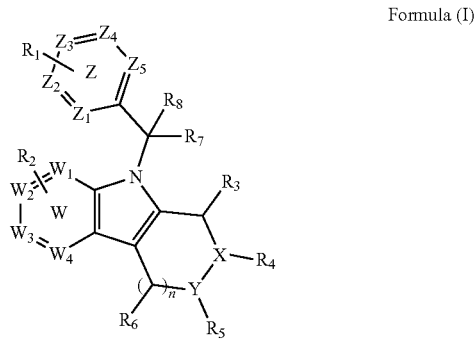

Formula (I)

Wherein:

$W_{1-4}$ and $Z_1$-$Z_5$ are each independently —C, —CH, $CH_2$, O, S, or N;

X is independently $CH_2$, N or $CHR_4$;

Y is independently $CH_2$, or $CHR_5$;

n is a number between 0 and 3;

One or more $R_1$'s on the ring Z are independently selected from the group consisting of: CN, OH, COOH, $OCH_3$, $CF_3$, $CONH_2$, $B(OH)_2$, $B(OR)_2$, an acid isostere, a substituted amine, ethers, and a halogen, substituted or unsubstituted alkyl, substituted or unsubstituted cyclic or heterocyclic, substituted or unsubstituted cycloaryl or cychloheteroaryl, wherein the substituted cycloaryl or cychloheteroaryl may be substituted with hydrogen, CN, OH, COOH, $OCH_3$, $CF_3$, $CONH_2$, $B(OH)_2$, $B(OR)_2$, an acid isostere, a substituted amine, ethers, and a halogen, substituted or unsubstituted alkyl, substituted or unsubstituted cyclic or heterocyclic, substituted or unsubstituted cycloaryl or cychloheteroaryl, $SO_2NH_2$;

One or more $R_2$'s on the ring W are independently selected from the group consisting of: CN, OH, CHF2, CH2F, $CF_3$, COOH, $CONH_2$, $B(OH)_2$, $B(OR)_2$, an acid isostere, a halogen, and a bicyclic heteroaryl;

$R_7$ is hydrogen or CN, COOH, $CONH_2$, $B(OH)_2$, $B(OR)_2$ or an acid isostere;

R is alkyl;

$R_3$, $R_4$, $R_5$ or $R_8$, or $R_6$ when n is not zero, is each independently selected from:

(1) hydrogen;
(2) substituted or unsubstituted alkyl or ether having 1 to 12 carbon atoms,
(3) a substituted amine, or
(4) —(CH$_2$)$_m$ G, wherein m is 1 to 12 and G is independently selected from:
 (a) cycloalkyl containing 3 to 6 carbon atoms,
 (b) aryl or heteroaryl,
 (c) CF$_3$, CF$_2$H or CFH$_2$, or
 (d) a heterocycle,
provided that R$_3$, R$_4$, R$_5$, R$_8$, or R$_6$ are not all hydrogen; or pharmaceutically acceptable salts or stereoisomers thereof.

In addition, the compound of Formula I, where R$_1$ and R$_2$ are both present, each is independently CN, COOH, or CONH$_2$.

In addition, the compound of Formula I, where the Formula I includes multiple R$_1$'s and R$_2$'s.

In addition, the compound of Formula I, wherein R$_3$, R$_4$, R$_5$, R$_8$, or R$_6$ when n is not zero, is each independently alkyl having 4 carbon atoms.

In addition, the compound of Formula I, wherein R$_3$, R$_4$, R$_5$, R$_8$, or R$_6$ when n is not zero, is each independently alkyl having 5 carbon atoms.

In addition, the compound of Formula I, wherein R$_3$, R$_4$, R$_5$, R$_8$, or R$_6$ when n is not zero, is each independently alkyl having 6 carbon atoms.

In addition, the ring Z of the compound of Formula I may have varying size (e.g., may be a five-membered ring, a six-membered ring, etc.).

In some examples, the ring Z of the compound of Formula I contains Z$_1$-Z$_4$.

In other examples, the ring Z of the compound of Formula I contains Z$_1$-Z$_5$.

In examples, the one or more R$_1$'s on the ring Z is the halogen.

In examples, the one or more R$_1$'s on the ring Z is the CN.

In examples, the one or more R$_1$'s on the ring Z is the CF$_3$.

In examples, the one or more R$_2$'s on the ring W is the halogen.

In examples, the one or more R$_1$'s on the ring Z comprise the CN and/or the halogen.

In examples, the one or more R$_1$'s on the ring Z comprise the CN and/or the halogen and the one or more R$_2$'s on the ring W comprise another halogen. In some examples, the halogen is identical to the other halogen. In other examples, the halogen differs from the other halogen.

In another of the embodiments, the invention is a compound of Formula (II), comprising:

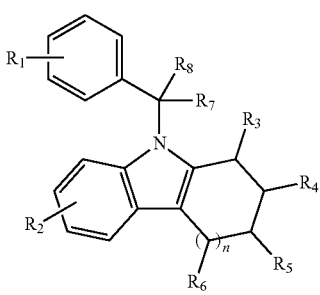

Formula (II)

Wherein:
n=0, 1, or 2;
R$_1$ is selected from the group consisting of: CN, COOH, CONH$_2$, B(OH)$_2$, B(OR)$_2$, an acid isostere, a halogen;

R$_2$ is selected from the group consisting of: CN, COOH, CONH$_2$, B(OH)$_2$, B(OR)$_2$, an acid isostere, a halogen, and a bicyclic compound;
R$_7$ is hydrogen or CN, COOH, CONH$_2$, B(OH)$_2$, B(OR)$_2$ or an acid isostere;
R is alkyl;
R$_3$, R$_4$, R$_5$ or R$_8$, or R$_6$ when n is not zero, is each independently selected from:
(1) hydrogen;
(2) alkyl having 1 to 12 carbon atoms, or
(3) —(CH$_2$)$_m$ G, wherein m is 1 to 12 and G is independently selected from:
 (a) cycloalkyl containing 3 to 6 carbon atoms
 (b) aryl or heteroaryl, or
 (c) CF$_3$, CF$_2$H or CFH$_2$
provided that G is not a nitrogen or oxygen-containing group; and
provided that R3, R4, R5, R8, or R6 are not all hydrogen; or pharmaceutically acceptable salts thereof.

In addition, the compound of Formula II, where when R$_1$ and R$_2$ are both present, each is independently CN, COOH, or CONH$_2$.

In addition, the compound of Formula II includes multiple R$_1$'s and R$_2$'s.

In addition, the compound of Formula II, wherein R$_3$, R$_4$, R$_5$, R$_8$, or R$_6$ when n is not zero, is each independently alkyl having 4 carbon atoms.

In addition, the compound of Formula I, wherein R$_3$, R$_4$, R$_5$, R$_8$, or R$_6$ when n is not zero, is each independently alkyl having 5 carbon atoms.

In addition, the compound of Formula I, wherein R$_3$, R$_4$, R$_5$, R$_8$, or R$_6$ when n is not zero, is each independently alkyl having 6 carbon atoms.

In yet another embodiment, the invention is a compound of Formula (III) comprising:

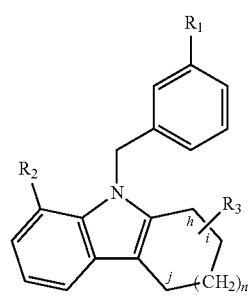

Formula (III)

Wherein:
n=0, 1 or 2;
R$_1$ and R$_2$ are each independently CN, COOH, CONH$_2$, B(OH)$_2$, B(OR)$_2$ or an acid isostere;
R is alkyl;
R$_3$ is independently selected from:
(1) alkyl having 1 to 12 carbon atoms;
(2) —(CH$_2$)$_m$G, wherein m is 1 to 12 and G is independently selected from:
 (a) cycloalkyl containing 3 to 6 carbon atoms; and
 (b) phenyl; and
provided that G is not a nitrogen or oxygen-containing group;
or pharmaceutically acceptable salts thereof.

A compound according to Formula III, wherein n=0 and R$_3$ is attached to the h-, i-, or j-position.

A compound according to Formula III, wherein n=1 and R₃ is attached to the h-, i-, or j-position.

A compound according to Formula III, wherein n=2 and R₃ is attached to the h-, i-, or j-position.

A compound according to Formula III, which is a pure optical isomer.

A compound according to Formula III, which is the (+)-isomer.

Definition

As used herein, the term "acid isostere" includes, but is not limited to, the following functional groups, where R is an alkyl group:

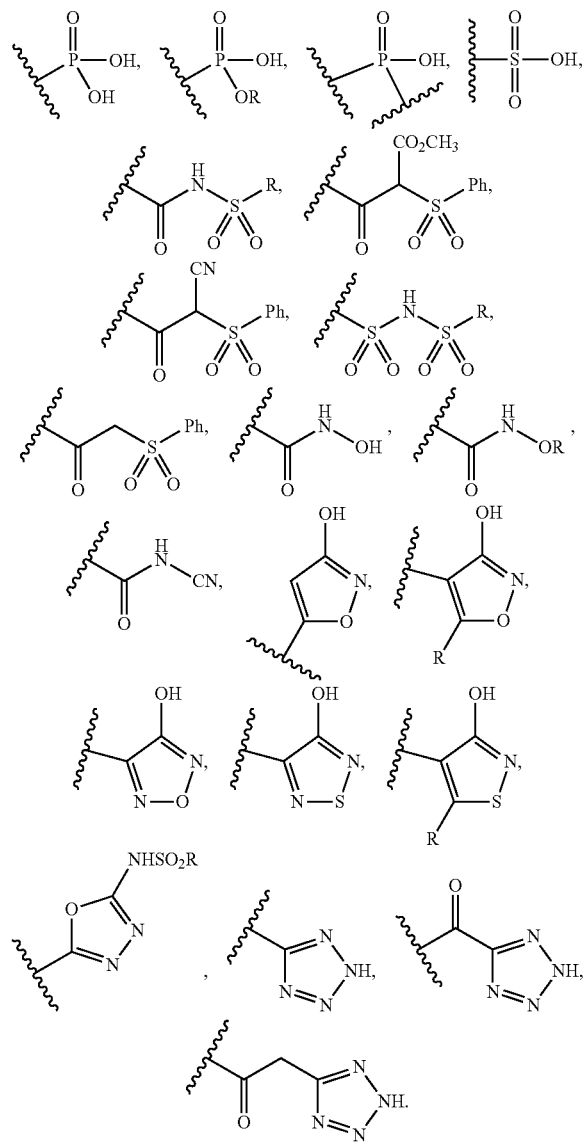

The term "alkyl" refers to a saturated, straight- or branched-chain hydrocarbon group having from 1 to 10 carbon atoms. Representative alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl, and the like, and longer alkyl groups, such as heptyl, octyl, and the like. As used herein, "lower alkyl" means an alkyl having from 1 to 6 carbon atoms.

The term "alkylenyl" refers to a divalent alkyl group.

The term "alkoxy" as used herein includes —O-(alkyl), wherein alkyl is defined above.

The term "amino" as used herein refers to an —NH₂ group.

"Aryl" means a mono-, bi-, or tricyclic aromatic group, wherein all rings of the group are aromatic and all ring atoms are carbon atoms. For bi- or tricyclic systems, the individual aromatic rings are fused to one another. Examples of aryl groups are 6 and 10 membered aryls. Further examples of aryl groups include, but are not limited to, phenyl, naphthalene, and anthracene.

The term "cyano" as used herein means a substituent having a carbon atom joined to a nitrogen atom by a triple bond.

The term "deuterium" as used herein means a stable isotope of hydrogen having one proton and one neutron.

The term "halo" represents chloro, fluoro, bromo, or iodo. In some embodiments, halo is chloro, fluoro, or bromo. The term "halogen" as used herein refers to fluorine, chlorine, bromine, or iodine.

The term "hydroxy" means an —OH group.

The term "oxo" means an =O group and may be attached to a carbon atom or a sulfur atom.

The term "N-oxide" refers to the oxidized form of a nitrogen atom.

As used herein, the term "cycloalkyl" refers to a saturated or partially saturated, monocyclic, fused polycyclic, bridged polycyclic, or spiro polycyclic carbocycle having from 3 to 15 carbon ring atoms. A non-limiting category of cycloalkyl groups are saturated or partially saturated, monocyclic carbocycles having from 3 to 6 carbon atoms. Illustrative examples of cycloalkyl groups include, but are not limited to, the following moieties:

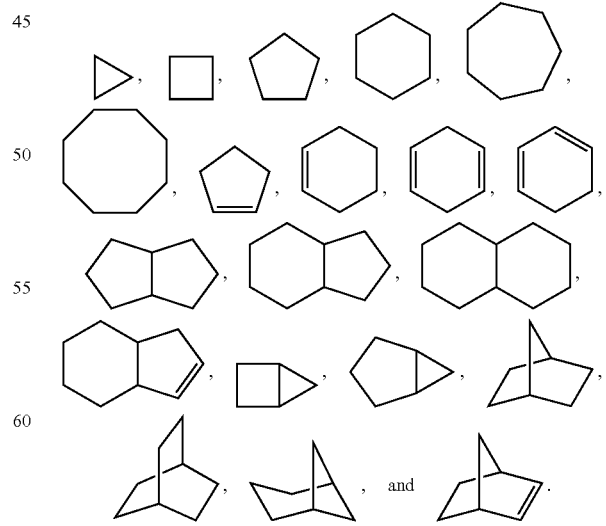

"Heterocycloalkyl" as used herein refers to a monocyclic, or fused, bridged, or spiro polycyclic ring structure that is saturated or partially saturated and has from three to 12 ring atoms selected from carbon atoms and up to three heteroatoms selected from nitrogen, oxygen, and sulfur. The ring structure may optionally contain up to two oxo groups on carbon or sulfur ring members, or an N-oxide. Illustrative heterocycloalkyl entities include, but are not limited to:

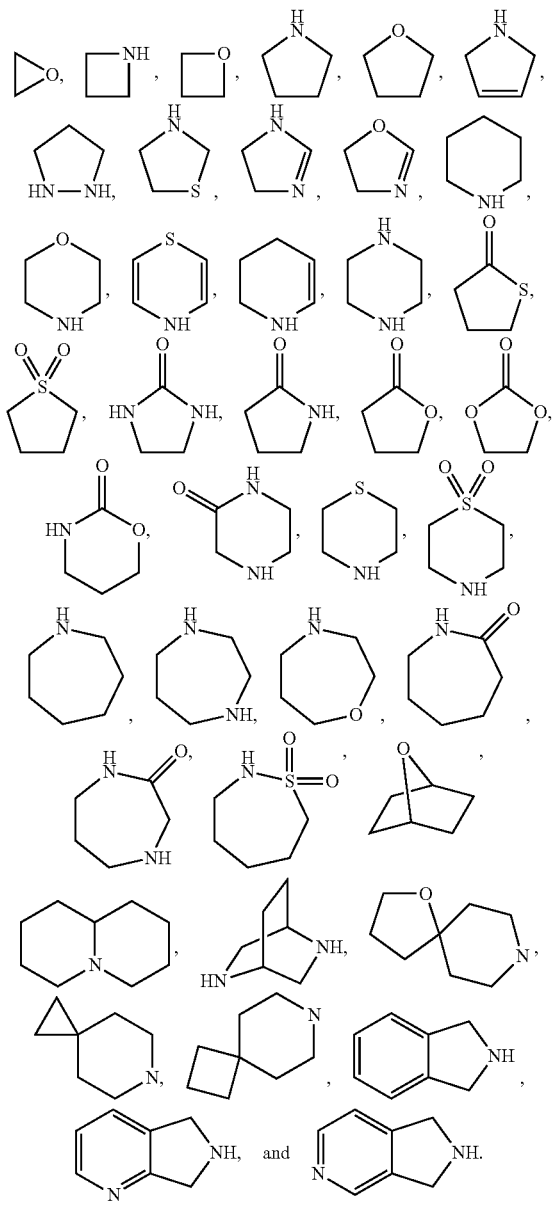

As used herein, the term "heteroaryl" refers to a monocyclic, or fused polycyclic, aromatic heterocycle having from three to 15 ring atoms that are selected from carbon, oxygen, nitrogen, and sulfur. Suitable heteroaryl groups do not include ring systems that must be charged to be aromatic, such as pyrylium. Suitable 5-membered heteroaryl rings (as a monocyclic heteroaryl or as part of a polycyclic heteroaryl) have one oxygen, sulfur, or nitrogen ring atom, or one nitrogen plus one oxygen or sulfur, or 2, 3, or 4 nitrogen ring atoms. Suitable 6-membered heteroaryl rings (as a monocyclic heteroaryl or as part of a polycyclic heteroaryl) have 1, 2, or 3 nitrogen ring atoms. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The term "bicyclic heteroaryl" refers to a heteroaryl as defined above, having two constituent aromatic rings, wherein the two rings are fused to one another and at least one of the rings is a heteroaryl as defined above. Bicyclic heteroaryls include bicyclic heteroaryl groups comprising 1, 2, 3, or 4 heteroatom ring atoms selected from O, N or S. In certain embodiments, wherein the heteroatom is N it can be an N-oxide. Bicyclic heteroaryls also include 8-, 9-, or 10-membered bicyclic heteroaryl groups. Bicyclic heteroaryls also include 8-, 9-, or 10-membered bicyclic heteroaryl groups that have 1, 2, 3, or 4 heteroatom ring atoms selected from O, N or S. Illustrative examples of bicyclic heteroaryls include, but are not limited to:

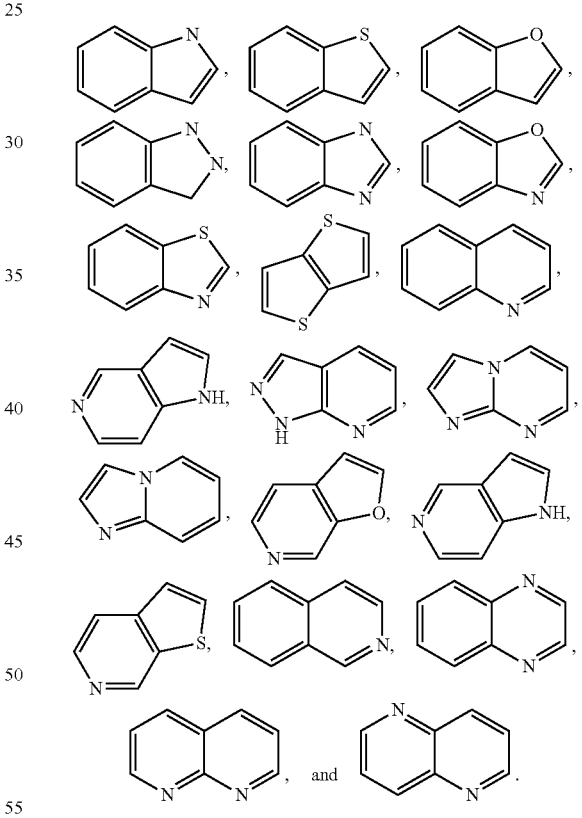

Those skilled in the art will recognize that the species of heteroaryl, cycloalkyl, and heterocycloalkyl groups listed or illustrated above are not exhaustive, and that additional species within the scope of these defined terms may also be selected.

As used herein, the term "substituted" means that the specified group or moiety bears one or more suitable substituents. As used herein, the term "unsubstituted" means that the specified group bears no substituents. As used herein, the term "optionally substituted" means that the specified group is unsubstituted or substituted by the specified number of substituents. Where the term "substituted" is used to describe a structural system, the substitution is meant to occur at any valency-allowed position on the system.

As used herein, the expression "one or more substituents" denotes one to maximum possible number of substitution(s) that can occur at any valency-allowed position on the system. In a certain embodiment, one or more substituent means 1, 2, 3, 4, or 5 substituents. In another embodiment, one or more substituent means 1, 2, or 3 substituents.

Any atom that is represented herein with an unsatisfied valence is assumed to have the sufficient number of hydrogen atoms to satisfy the atom's valence.

When any variable (e.g., alkyl or Ra) appears in more than one place in any formula or description provided herein, the definition of that variable on each occurrence is independent of its definition at every other occurrence.

Numerical ranges, as used herein, are intended to include sequential whole numbers. For example, a range expressed as "from 0 to 4" or "0-4" includes 0, 1, 2, 3 and 4.

When a multifunctional moiety is shown, the point of attachment to the remainder of the formula can be at any point on the multifunctional moiety. In some embodiments, the point of attachment is indicated by a line or hyphen. For example, aryloxy-refers to a moiety in which an oxygen atom is the point of attachment to the core molecule while aryl is attached to the oxygen atom.

Additional Definitions

As used herein, "proton nuclear magnetic resonance" or 1H NMR is the application of nuclear magnetic resonance in NMR spectroscopy with respect to hydrogen-1 nuclei within the molecules of a substance, in order to determine the structure of its molecules.

As used herein, the term "subject" encompasses mammals and non-mammals. Examples of mammals include, but are not limited to, any member of the Mammalian class: humans; non-human primates such as chimpanzees, and other apes and monkey species; farm animals such as cattle, horses, sheep, goats, swine; domestic animals such as rabbits, dogs, and cats; and laboratory animals including rodents, such as rats, mice and guinea pigs, and the like. Examples of non-mammals include, but are not limited to, birds, fish and the like. In one embodiment of the present invention, the mammal is a human.

"Patient" includes both human and animals.

The term "inhibitor" refers to a molecule such as a compound, a drug, an enzyme activator, or a hormone that blocks or otherwise interferes with a particular biologic activity.

The term "modulator" refers to a molecule, such as a compound of the present invention, that increases or decreases, or otherwise affects the activity of a given enzyme or protein.

The terms "effective amount" or "therapeutically effective amount" refer to a sufficient amount of the agent to provide the desired biological result. That result can be reduction and/or alleviation of the signs, symptoms, or causes of a disease or medical condition, or any other desired alteration of a biological system. For example, an "effective amount" for therapeutic use is the amount of a compound, or of a composition comprising the compound, that is required to provide a clinically relevant change in a disease state, symptom, or medical condition. An appropriate "effective" amount in any individual case may be determined by one of ordinary skill in the art using routine experimentation. Thus, the expression "effective amount" generally refers to the quantity for which the active substance has a therapeutically desired effect.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

Additional Chemical Descriptions

Any formula given herein is intended to represent compounds having structures depicted by the structural formula as well as certain variations or forms. For example, compounds of any formula given herein may have asymmetric or chiral centers and therefore exist in different stereoisomeric forms. All stereoisomers, including optical isomers, enantiomers, and diastereomers, of the compounds of the general formula, and mixtures thereof, are considered to fall within the scope of the formula. Furthermore, certain structures may exist as geometric isomers (i.e., cis and trans isomers), as tautomers, or as atropisomers. All such isomeric forms, and mixtures thereof, are contemplated herein as part of the present invention. Thus, any formula given herein is intended to represent a racemate, one or more enantiomeric forms, one or more diastereomeric forms, one or more tautomeric or atropisomeric forms, and mixtures thereof.

Diastereomeric mixtures may be separated into their individual diastereomers on the basis of their physical chemical differences by methods well known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride, or formation of a mixture of diastereomeric salts), separating the diastereomers and converting (e.g., hydrolyzing or de-salting) the individual diastereomers to the corresponding pure enantiomers. Enantiomers may also be separated by use of chiral HPLC column. The chiral centers of compounds of the present invention may be designated as "R" or "S" as defined by the IUPAC 1974 Recommendations.

The compounds of the invention can form pharmaceutically acceptable salts, which are also within the scope of this invention. A "pharmaceutically acceptable salt" refers to a salt of a free acid or base of a compound of Formula I, II, or III that is non-toxic, is physiologically tolerable, is compatible with the pharmaceutical composition in which it is formulated, and is otherwise suitable for formulation and/or administration to a subject. Reference to a compound herein is understood to include reference to a pharmaceutically acceptable salt of said compound unless otherwise indicated.

Compound salts include acidic salts formed with inorganic and/or organic acids, as well as basic salts formed with inorganic and/or organic bases. In addition, where a given compound contains both a basic moiety, such as, but not limited to, a pyridine or imidazole, and an acidic moiety, such as, but not limited to, a carboxylic acid, one of skill in the art will recognize that the compound may exist as a zwitterion ("inner salt"); such salts are included within the term "salt" as used herein. Salts of the compounds of the invention may be prepared, for example, by reacting a compound with an amount of a suitable acid or base, such as an equivalent amount, in a medium such as one in which the salt precipitates or in an aqueous medium followed by lyophilization.

Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate ("mesylate"), ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counter ion.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Additionally, acids and bases which are generally considered suitable for the formation of pharmaceutically useful salts from pharmaceutical compounds are discussed, for example, by P. Stahl et al., Camille G. (eds.) Handbook of Pharmaceutical Salts: Properties, Selection and Use. (2002) Zurich: Wiley-VCH; S. Berge et al., *J. Pharm. Sci.* (1977) 66(1) 1-19; P. Gould, *Int. J. Pharm.* (1986) 33 201-217; Anderson et al., The Practice of Medicinal Chemistry (1996), Academic Press, New York; and in The Orange Book (Food & Drug Administration, MD, available from FDA). These disclosures are incorporated herein by reference thereto.

Additionally, any compound described herein is intended to refer also to any unsolvated form, or a hydrate, solvate, or polymorph of such a compound, and mixtures thereof, even if such forms are not listed explicitly. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of a crystalline solid. "Solvate" encompasses both solution-phase and isolatable solvates. Suitable solvates include those formed with pharmaceutically acceptable solvents such as water, ethanol, and the like. In some embodiments, the solvent is water and the solvates are hydrates.

One or more compounds of the invention may optionally be converted to a solvate. Methods for the preparation of solvates are generally known. Thus, for example, M. Caira et al., *J Pharm. Sci.*, 93(3), 601-611 (2004), describes the preparation of the solvates of the antifungal fluconazole in ethyl acetate as well as from water. Similar preparations of solvates, hemisolvate, hydrates, and the like are described by E. C. van Tonder et al., AAPS PharmSciTech., 5(1), article 12 (2004); and A. L. Bingham et al., Chem. Commun., 603-604 (2001). A typical, non-limiting process involves dissolving the inventive compound in a suitable amounts of the solvent (organic solvent or water or a mixture thereof) at a higher than ambient temperature, and cooling the solution at a rate sufficient to form crystals which are then isolated by standard methods. Analytical techniques such as, for example, infrared spectroscopy, show the presence of the solvent (or water) in the crystals as a solvate (or hydrate).

The invention also relates to pharmaceutically acceptable prodrugs of the compounds of Formula I, II, or III, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula I, II, or III). A "pharmaceutically acceptable prodrug" is a prodrug that is non-toxic, biologically tolerable, and otherwise suitable for formulation and/or administration to the subject. Illustrative procedures for the selection and preparation of suitable prodrug derivatives are described, for example, in "Design of Prodrugs", ed. H. Bundgaard, Elsevier, 1985.

Examples of prodrugs include pharmaceutically acceptable esters of the compounds of the invention, which are also considered to be part of the invention. Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, $C_{1-4}$alkoxy, or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol. Additional discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press.

For example, if a compound of Formula I, II, or III contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N—$(C_1$-$C_2)$alkylamino$(C_2$-$C_3)$alkyl (such as β-dimethylaminoethyl), carbamoyl-$(C_1$-$C_2)$alkyl, N,N-di$(C_1$-$C_2)$alkylcarbamoyl-$(C_1$-$C_2)$alkyl and piperidino-, pyrrolidino- or morpholine $(C_2$-$C_3)$alkyl, and the like.

Similarly, if a compound of Formula I, II, or III contains an alcohol functional group, a prodrug can be formed by the replacement of the hydrogen atom of the alcohol group with a group such as, for example, $(C_1$-$C_6)$alkanoyloxymethyl, 1-($(C_1$-$C_6)$alkanoyloxy)ethyl, 1-methyl-1-($(C_1$-$C_6)$alkanoyloxy)ethyl, $(C_1$-$C_6)$alkoxycarbonyloxymethyl, N—$(C_1$-$C_6)$ alkoxycarbonylaminomethyl, succinoyl, $(C_1$-$C_6)$alkanoyl, α-amino$(C_1$-$C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1$-$C_6)$alkyl$)_2$ or glycosyl (the radical resulting from the removal of a hydroxyl group of the hemiacetal form of a carbohydrate), and the like.

If a compound of Formula I, II, or III incorporates an amine functional group, a prodrug can be formed by the replacement of a hydrogen atom in the amine group with a group such as, for example, R"-carbonyl, R"O-carbonyl, NR"R'-carbonyl where R" and R' are each independently $(C_1$-$C_{10})$alkyl, $(C_3$-$C_7)$ cycloalkyl, benzyl, or R"-carbonyl is a natural α-aminoacyl or natural α-aminoacyl, —C(OH)C(O)OY$^1$ wherein Y$^1$ is H, $(C_1$-$C_6)$alkyl or benzyl, —C(OY$^2$) Y$^3$ wherein Y$^2$ is $(C_1$-$C_4)$ alkyl and Y$^3$ is $(C_1$-$C_6)$alkyl, carboxy$(C_1$-$C_6)$alkyl, amino$(C_1$-$C_4)$alkyl or mono-N- or di-N,N-$(C_1$-$C_6)$alkylaminoalkyl, —C(Y$^4$)Y$^5$ wherein Y$^4$ is H or methyl and Y$^5$ is mono-N- or di-N,N-$(C_1$-$C_6)$alkylamino morpholino, piperidin-1-yl or pyrrolidin-1-yl, and the like.

The present invention also relates to pharmaceutically active metabolites of compounds of Formula I, II, or III, and uses of such metabolites in the methods of the invention. A "pharmaceutically active metabolite" means a pharmacologically active product of metabolism in the body of a compound of Formula I, II, or III or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively. Such isotopically labelled compounds are useful in metabolic studies (for example with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. In particular, an $^{18}$T or $^{11}$C labeled compound may be particularly suitable for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

The use of the terms "salt," "solvate," "polymorph," "prodrug," and the like, with respect to the compounds described herein is intended to apply equally to the salt, solvate, polymorph, and prodrug forms of enantiomers, stereoisomers, rotamers, tautomers, atropisomers, and racemates of the inventive compounds.

The invention can also be a compound selected from the group consisting of: 5-[(3-cyanophenyl)methyl]-2-fluoro-7-hexyl-5H,6H,7H,8H,9H,10H-cyclohepta[b]indole-4-carboxylic acid, 5-[(6-cyanopyridin-2-yl)methyl]-7-hexyl-5H, 6H,7H,8H,9H,10H-cyclohepta[b]indole-4-carboxylic acid, 5-[(6-carbamoylpyridin-2-yl)methyl]-7-hexyl-5H,6H,7H, 8H,9H,10H-cyclohepta[b]indole-4-carboxylic acid, 6-({4-carboxy-7-hexyl-5H,6H,7H,8H,9H,10H-cyclohepta[b]indol-5-yl}methyl)pyridine-2-carboxylic acid, 5-[(3-cyano-2-fluorophenyl)methyl]-7-hexyl-5H,6H,7H,8H,9H,10H-cyclohepta[b]indole-4-carboxylic acid, 5-[(1,3-benzoxazol-6-yl)methyl]-7-hexyl-5H,6H,7H,8H,9H,10H-cyclohepta[b]indole-4-carboxylic acid, 5-[(1,3-benzoxazol-5-yl)methyl]-7-hexyl-5H,6H,7H,8H,9H,10H-cyclohepta[b]indole-4-carboxylic acid, 5-[(6-fluoropyridin-2-yl)methyl]-7-hexyl-5H,6H,7H,8H,9H,10H-cyclohepta[b]indole-4-carboxylic acid, 5-[(2-fluoropyridin-4-yl)methyl]-7-hexyl-5H,6H,7H,8H,9H,10H-cyclohepta[b]indole-4-carboxylic acid, 7-hexyl-5-{[6-(trifluoromethyl)pyridin-2-yl]methyl}-5H,6H,7H,8H,9H,10H-cyclohepta[b]indole-4-carboxylic acid, 7-hexyl-5-{[2-(trifluoromethyl)pyridin-4-yl]methyl}-5H, 6H,7H,8H,9H,10H-cyclohepta[b]indole-4-carboxylic acid, 5-[(5-cyanopyridin-3-yl)methyl]-7-hexyl-5H,6H,7H,8H, 9H,10H-cyclohepta[b]indole-4-carboxylic acid, 5-[(5-cyanothiophen-2-yl)methyl]-7-hexyl-5H,6H,7H,8H,9H,10H-cyclohepta[b]indole-4-carboxylic acid, 5-[(4-cyanothiophen-2-yl)methyl]-7-hexyl-5H,6H,7H,8H,9H, 10H-cyclohepta[b]indole-4-carboxylic acid, 5-[(5-cyanofuran-2-yl)methyl]-7-hexyl-5H,6H,7H,8H,9H,10H-cyclohepta[b]indole-4-carboxylic acid, 5-[(3,5-dimethyl-1,2-oxazol-4-yl)methyl]-7-hexyl-5H,6H,7H,8H,9H,10H-cyclohepta[b]indole-4-carboxylic acid, 5-(3-cyanobenzoyl)-7-hexyl-5H,6H,7H,8H,9H,10H-cyclohepta[b]indole-4-carboxylic acid, 5-[(1,3-benzoxazol-7-yl)methyl]-7-hexyl-5H,6H,7H,8H,9H,10H-cyclohepta[b]indole-4-carboxylic acid, 5-[(5-cyanothiophen-3-yl)methyl]-7-hexyl-5H,6H,7H, 8H,9H,10H-cyclohepta[b]indole-4-carboxylic acid, 7-hexyl-5-[(1H-indol-4-yl)methyl]-5H,6H,7H,8H,9H,10H-cyclohepta[b]indole-4-carboxylic acid, 5-[(3-carbamoylphenyl)methyl]-7-propyl-5H,6H,7H,8H,9H,10H-cyclohepta[b]indole-4-carboxylic acid, 7-butyl-5-[(3-carbamoylphenyl)methyl]-5H,6H,7H,8H,9H,10H-cyclohepta[b]indole-4-carboxylic acid, 7-butyl-5-[(3-cyanophenyl)methyl]-5H,6H,7H,8H,9H,10H-cyclohepta[b]indole-4-carboxylic acid, 7-butyl-5-[(pyridin-3-yl)methyl]-5H,6H,7H,8H,9H,10H-cyclohepta[b]indole-4-carboxylic acid, 7-butyl-5-[(3-methylphenyl)methyl]-5H,6H,7H,8H,9H,10H-cyclohepta[b]indole-4-carboxylic acid, 7-butyl-5-[(3-methoxyphenyl)methyl]-5H,6H,7H,8H,9H,10H-cyclohepta[b]indole-4-carboxylic acid, 7-butyl-5-[(3-chlorophenyl)methyl]-5H,6H,7H,8H,9H,10H-cyclohepta[b]indole-4-carboxylic acid, 7-butyl-5-[(3-hydroxyphenyl)methyl]-5H,6H,7H,8H,9H,10H-cyclohepta[b]indole-4-carboxylic acid, 7-butyl-5-[(2-methoxypyridin-4-yl)methyl]-5H,6H,7H,8H,9H,10H-cyclohepta[b]indole-4-carboxylic acid, 7-butyl-5-[(4-carbamoylphenyl)methyl]-5H,6H,7H,8H,9H,10H-cyclohepta[b]indole-4-carboxylic acid, 7-butyl-5-[(2-carbamoylphenyl)methyl]-5H,6H,7H,8H,9H,10H-cyclohepta[b]indole-4-carboxylic acid, 7-butyl-5-[(4-methylphenyl)methyl]-5H,6H,7H,8H,9H,10H-cyclohepta[b]indole-4-carboxylic acid, 7-butyl-5-[(2-cyanophenyl)methyl]-5H,6H,7H,8H,9H,10H-cyclohepta[b]indole-4-carboxylic acid, 7-butyl-5-[(2-methylphenyl)methyl]-5H,6H,7H,8H,9H,10H-cyclohepta[b]indole-4-carboxylic acid, 7-butyl-5-[(2-fluorophenyl)methyl]-5H,6H,7H,8H,9H,10H-cyclohepta[b]indole-4-carboxylic acid, 5-[(3-carbamoylphenyl)methyl]-7-pentyl-5H,6H,7H,8H,9H,10H-cyclohepta[b]indole-4-carboxylic acid, 5-[(3-cyanophenyl)methyl]-7-pentyl-5H,6H,7H,8H,9H,10H-cyclohepta[b]indole-4-carboxylic acid, 5-[(3-carbamoylphenyl)methyl]-7-(2-phenylethyl)-5H,6H,7H,8H,9H,10H-cyclohepta[b]indole-4-carboxylic acid, 5-[(3-cyanophenyl)methyl]-7-(2-phenylethyl)-5H,6H,7H,8H,9H,10H-cyclohepta[b]indole-4-carboxylic acid, 5-[(3-carbamoylphenyl)methyl]-7-hexyl-5H,6H,7H,8H,9H,10H-cyclohepta[b]indole-4-carboxylic acid, 5-[(3-cyanophenyl)methyl]-7-hexyl-5H,6H,7H,8H,9H,10H-cyclohepta[b]indole-4-carboxylic acid, 5-[(3-carbamoylphenyl)methyl]-7-octyl-5H,6H,7H,8H,9H,10H-cyclohepta[b]indole-4-carboxylic acid, 5-[(3-cyanophenyl)methyl]-7-octyl-5H,6H,7H,8H,9H,10H-cyclohepta[b]indole-4-carboxylic acid, 5-[(3-fluorophenyl)methyl]-7-hexyl-5H,6H,7H,8H,9H,10H-cyclohepta[b]indole-4-carboxylic acid, 7-hexyl-5-[(pyridin-3-yl)methyl]-5H,6H,7H,8H,9H,10H-cyclohepta[b]indole-4-carboxylic acid, 7-hexyl-5-[(3-methylphenyl)methyl]-5H,6H,7H,8H,9H,10H-cyclohepta[b]indole-4-carboxylic acid, 7-hexyl-5-[(3-methoxyphenyl)methyl]-5H,6H,7H,8H,9H,10H-cyclohepta[b]indole-4-carboxylic acid, 5-[(3-chlorophenyl)methyl]-7-hexyl-5H,6H,7H,8H,9H,10H-cyclohepta[b]indole-4-carboxylic acid, 7-hexyl-5-[(2-methoxypyridin-4-yl)methyl]-5H,6H,7H,8H,9H,10H-cyclohepta[b]indole-4-carboxylic acid, 5-[(3-carboxyphenyl)methyl]-7-hexyl-5H,6H,7H,8H,9H,10H-cyclohepta[b]indole-4-carboxylic acid, 5-[(4-carbamoylphenyl)methyl]-7-hexyl-5H,6H,7H,8H,9H,10H-cyclohepta[b]indole-4-carboxylic acid, 5-[(2-carbamoylphenyl)methyl]-7-hexyl-5H,6H,7H,8H,9H,10H-cyclohepta[b]indole-4-carboxylic acid, 7-hexyl-5-[(4-methylphenyl)methyl]-5H,6H,7H,8H,9H,10H-cyclohepta[b]indole-4-carboxylic acid, 5-[(4-cyanophenyl)methyl]-7-hexyl-5H,6H,7H,8H,9H,10H-cyclohepta[b]indole-4-carboxylic acid, 5-[(2-cyanophenyl)methyl]-7-hexyl-5H,6H,7H,8H,9H,10H-cyclohepta[b]indole-4-carboxylic acid, 7-hexyl-5-[(2-methylphenyl)methyl]-5H,6H,7H,8H,9H,10H-cyclohepta[b]indole-4-carboxylic acid, 5-[(2-fluorophenyl)methyl]-7-hexyl-5H,6H,7H,8H,9H,10H-cyclohepta[b]indole-4-carboxylic acid, 5-[(4-fluorophenyl)methyl]-7-hexyl-5H,6H,7H,8H,9H,10H-cyclohepta[b]indole-4-carboxylic acid, 9-[(3-carbamoylphenyl)methyl]-2-hexyl-2,3,4,9-tetrahydro-1H-carbazole-8-carboxylic acid, 9-[(3-cyanophenyl)methyl]-2-hexyl-2,3,4,9-tetrahydro-1H-carbazole-8-carboxylic acid, 9-[(3-carboxyphenyl)methyl]-2-hexyl-2,3,4,9-tetrahydro-1H-carbazole-8-carboxylic acid, 9-[(3-fluorophenyl)methyl]-2-hexyl-2,3,4,9-tetrahydro-1H-carbazole-8-carboxylic acid, 2-hexyl-9-[(pyridin-3-yl)methyl]-2,3,4,9-tetrahydro-1H-carbazole-8-carboxylic acid, 2-hexyl-9-[(3-methylphenyl)methyl]-2,3,4,9-tetrahydro-1H-carbazole-8-carboxylic acid, 2-hexyl-9-[(3-methoxyphenyl)methyl]-2,3,4,9-tetrahydro-1H-carbazole-8-carboxylic acid, 9-[(3-chlorophenyl)methyl]-2-hexyl-2,3,4,9-tetrahydro-1H-carbazole-8-carboxylic acid, 2-hexyl-9-[(3-hydroxyphenyl)methyl]-2,3,4,9-tetrahydro-1H-carbazole-8-carboxylic acid, 2-hexyl-9-[(2-methoxypyridin-4-yl)methyl]-2,3,4,9-tetrahydro-1H-carbazole-8-carboxylic acid, 9-[(3-carboxyphenyl)methyl]-2-hexyl-2,3,4,9-tetrahydro-1H-carbazole-8-carboxylic acid, 9-[(4-carbamoylphenyl)methyl]-2-hexyl-2,3,4,9-tetrahydro-1H-carbazole-8-carboxylic acid, 9-[(2-carbamoylphenyl)methyl]-2-hexyl-2,3,4,9-tetrahydro-1H-carbazole-8-carboxylic acid, 2-hexyl-9-[(4-methylphenyl)methyl]-2,3,4,9-tetrahydro-1H-carbazole-8-carboxylic acid, 9-[(4-cyanophenyl)methyl]-2-hexyl-2,3,4,9-tetrahydro-1H-carbazole-8-carboxylic acid, 9-[(2-cyanophenyl)methyl]-2-hexyl-2,3,4,9-tetrahydro-1H-carbazole-8-carboxylic acid, 2-hexyl-9-[(2-methylphenyl)methyl]-2,3,4,9-tetrahydro-1H-carbazole-8-carboxylic acid, 9-[(2-fluorophenyl)methyl]-2-hexyl-2,3,4,9-tetrahydro-1H-carbazole-8-carboxylic acid, 9-[(3-carbamoylphenyl)methyl]-2-(2-phenylethyl)-2,3,4,9-tetrahydro-1H-carbazole-8-carboxylic acid, 9-[(3-cyanophenyl)methyl]-2-(2-phenylethyl)-2,3,4,9-tetrahydro-1H-carbazole-8-carboxylic acid, 9-[(3-carbamoylphenyl)methyl]-4-(2-phenylethyl)-2,3,4,9-tetrahydro-1H-carbazole-8-carboxylic acid, 9-[(3-cyanophenyl)methyl]-4-(2-phenylethyl)-2,3,4,9-tetrahydro-1H-carbazole-8-carboxylic acid, 9-[(3-carbamoylphenyl)methyl]-2-propyl-2,3,4,9-tetrahydro-1H-carbazole-8-carboxylic acid, 9-[(3-cyanophenyl)methyl]-2-propyl-2,3,4,9-tetrahydro-1H-carbazole-8-carboxylic acid, 2-butyl-9-[(3-carbamoylphenyl)methyl]-2,3,4,9-tetrahydro-1H-carbazole-8-carboxylic acid, 9-[(3-carbamoylphenyl)methyl]-2-pentyl-2,3,4,9-tetrahydro-1H-carbazole-8-carboxylic acid, 9-[(3-cyanophenyl)methyl]-2-pentyl-2,3,4,9-tetrahydro-1H-carbazole-8-carboxylic acid, 1-butyl-9-[(3-carbamoylphenyl)methyl]-2,3,4,9-tetrahydro-1H-carbazole-8-carboxylic acid, 9-[(3-carbamoylphenyl)methyl]-1-(pentyloxy)-2,3,4,9-tetrahydro-1H-carbazole-8-carboxylic acid, 9-[(3-cyanophenyl)methyl]-1-(pentyloxy)-2,3,4,9-tetrahydro-1H-carbazole-8-carboxylic acid, 1-butyl-9-[(3-cyanophenyl)methyl]-2,3,4,9-tetrahydro-1H-carbazole-8-carboxylic acid, 6-butyl-5-[(3-carbamoylphenyl)methyl]-5H,6H,7H,8H,9H,10H-cyclohepta[b]indole-4-carboxylic acid, 6-butyl-5-[(3-cyanophenyl)methyl]-5H,6H,7H,8H,9H,10H-cyclohepta[b]indole-4-carboxylic acid, 9-[(3-carbamoylphenyl)methyl]-1-ethyl-2,3,4,9-tetrahydro-1H-carbazole-8-carboxylic acid, 9-[(3-cyanophenyl)methyl]-1-ethyl-2,3,4,9-tetrahydro-1H-carbazole-8-carboxylic acid, 9-[(3-carboxyphenyl)methyl]-1-ethyl-2,3,4,9-tetrahydro-1H-carbazole-8-carboxylic acid, 9-[(3-carbamoylphenyl)methyl]-1-propoxy-2,3,4,9-tetrahydro-1H-carbazole-8-carboxylic acid, 9-[(3-carbamoylphenyl)methyl]-4-ethyl-2,3,4,9-tetrahydro-1H-carbazole-8-carboxylic acid, 4-[(3-carbamoylphenyl)methyl]-3- ethyl-1H,2H,3H,4H-cyclopenta[b]indole-5-carboxylic acid, 4-[(3-cyanophenyl)methyl]-3-ethyl-1H,2H,3H,4H-cyclopenta[b]indole-5-carboxylic acid, 3-butyl-4-[(3-carbamoylphenyl)methyl]-1H,2H,3H,4H-cyclopenta[b]indole-5-carboxylic acid, 3-butyl-4-[(3-cyanophenyl)methyl]-1H,2H,3H,4H-cyclopenta[b]indole-5-carboxylic acid, 2-butyl-4-[(3-carbamoylphenyl)methyl]-1H,2H,3H,4H-cyclopenta[b]indole-5-carboxylic acid, 2-butyl-4-[(3-cyanophenyl)methyl]-1H,2H,3H,4H-cyclopenta[b]indole-5-carboxylic acid, 5-[(3-carbamoylphenyl)methyl]-10-ethyl-5H,6H,7H,8H,9H,10H-cyclohepta[b]indole-4-carboxylic acid, 5-[(3-cyanophenyl)methyl]-10-ethyl-5H,6H,7H,8H,9H,10H-cyclohepta[b]indole-4-carboxylic acid, 5-[(3-carbamoylphenyl)methyl]-10-propyl-5H,6H,7H,8H,9H,10H-cyclohepta[b]indole-4-carboxylic acid, 5-[(3-cyanophenyl)methyl]-10-propyl-5H,6H,7H,8H,9H,10H-cyclohepta[b]indole-4-carboxylic acid, 9-[(3-carboxyphenyl)methyl]-4-ethyl-2,3,4,9-tetrahydro-1H-carbazole-8-carboxylic acid, 9-[(3-carbamoylphenyl)methyl]-3-ethyl-2,3,4,9-tetrahydro-1H-carbazole-8-carboxylic acid, 10-butyl-5-[(3-carbamoylphenyl)methyl]-5H,6H,7H,8H,9H,10H-cyclohepta[b]indole-4-carboxylic acid, 10-butyl-5-[(3-cyanophenyl)methyl]-5H,6H,7H,8H,9H,10H-cyclohepta[b]indole-4-carboxylic acid, 5-[(3-carbamoylphenyl)methyl]-10-pentyl-5H,6H,7H,8H,9H,10H-cyclohepta[b]indole-4-carboxylic acid, 5-[(3-cyanophenyl)methyl]-10-pentyl-5H,6H,7H,8H,9H,10H-cyclohepta[b]indole-4-carboxylic acid, 4-[(3-carbamoylphenyl)methyl]-2-pentyl-1H,2H,3H,4H-cyclopenta[b]indole-5-carboxylic acid, 4-[(3-cyanophenyl)methyl]-2-pentyl-1H,2H,3H,4H-cyclopenta[b]indole-5-carboxylic acid, 9-[(3-carbamoylphenyl)methyl]-2-ethyl-2,3,4,9-tetrahydro-1H-carbazole-8-carboxylic acid, 9-[(3-carboxyphenyl)methyl]-2-ethyl-2,3,4,9-tetrahydro-1H-carbazole-8-carboxylic acid, 5-[(3-carbamoylphenyl)methyl]-7-ethyl-5H,6H,7H,8H,9H,10H-cyclohepta[b]indole-4-carboxylic acid, 5-[(3-cyanophenyl)methyl]-7-ethyl-5H,6H,7H,8H,9H,10H-cyclohepta[b]indole-4-carboxylic acid, 9-[(3-cyanophenyl)methyl]-3-ethyl-2,3,4,9-tetrahydro-1H-carbazole-8-carboxylic acid, 9-[(3-carbamoylphenyl)methyl]-4-propyl-2,3,4,9-tetrahydro-1H-carbazole-8-carboxylic acid, 9-[(3-carbamoylphenyl)methyl]-3-propyl-2,3,4,9-tetrahydro-1H-carbazole-8-carboxylic acid, 9-[(3-cyanophenyl)methyl]-3-propyl-2,3,4,9-tetrahydro-1H-carbazole-8-carboxylic acid, 4-butyl-9-[(3-carbamoylphenyl)methyl]-2,3,4,9-tetrahydro-1H-carbazole-8-carboxylic acid, 4-butyl-9-[(3-cyanophenyl)methyl]-2,3,4,9-tetrahydro-1H-carbazole-8-carboxylic acid, 3-butyl-9-[(3-carbamoylphenyl)methyl]-2,3,4,9-tetrahydro-1H-carbazole-8-carboxylic acid, 3-butyl-9-[(3-cyanophenyl)methyl]-2,3,4,9-tetrahydro-1H-carbazole-8-carboxylic acid, 9-[(3-carbamoylphenyl)methyl]-4-pentyl-2,3,4,9-tetrahydro-1H-carbazole-8-carboxylic acid, 9-[(3-cyanophenyl)methyl]-4-pentyl-2,3,4,9-tetrahydro-1H-carbazole-8-carboxylic acid, 9-[(3-carbamoylphenyl)methyl]-3-pentyl-2,3,4,9-tetrahydro-1H-carbazole-8-carboxylic acid, 9-[(3-cyanophenyl)methyl]-3-pentyl-2,3,4,9-tetrahydro-1H-carbazole-8-carboxylic acid, 4-[(3-carbamoylphenyl)methyl]-3-propyl-1H,2H,3H,4H-cyclopenta[b]indole-5-carboxylic acid, 4-[(3-cyanophenyl)methyl]-3-propyl-1H,2H,3H,4H-cyclopenta[b]indole-5-carboxylic acid, 2-({7-butyl-5-[(3-carbamoylphenyl)methyl]-5H,6H,7H,8H,9H,10H-cyclohepta[b]indol-4-yl}formamido)acetic acid, 2-({7-butyl-5-[(3-cyanophenyl)methyl]-5H,6H,7H,8H,9H,10H-cyclohepta[b]indol-4-yl}formamido)acetic acid, 7-butyl-5-[(3-carbamoylphenyl)methyl]-N-(2-hydroxyethyl)-5H,6H,7H,8H,9H,10H-cyclohepta[b]indole-4-carboxamide, 7-butyl-5-[(3-cyanophenyl)methyl]-N-(2-hydroxyethyl)-5H,6H,7H,8H,9H,10H-cyclohepta[b]indole-4-carboxamide, 7-butyl-5-[(3-fluorophenyl)methyl]-5H,6H,7H,8H,9H,10H-cyclohepta[b]indole-4-carboxylic acid, and 7-butyl-5-[(3-carboxyphenyl)methyl]-5H,6H,7H,8H,9H,10H-cyclohepta[b]indole-4-carboxylic acid, or pharmaceutically acceptable salts or stereoisomers thereof.

Yet another embodiment is a method for administering a compound of the instant invention to a subject (e.g., a human) in need thereof by administering to the subject the pharmaceutical formulation of the present invention.

Yet another embodiment is a method of preparing a pharmaceutical formulation of the present invention by mixing at least one pharmaceutically acceptable compound of the present invention, and, optionally, one or more pharmaceutically acceptable additives or excipients.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

The compositions and formulations of the invention can be administered as sterile compositions and sterile formulations. Sterile pharmaceutical formulations are compounded or manufactured according to pharmaceutical-grade sterilization standards (e.g., United States Pharmacopeia Chapters 797, 1072, and 1211; California Business & Professions Code 4127.7; 16 California Code of Regulations 1751, 21 Code of Federal Regulations 21, or ex-U.S. counterparts to such regulations) known to those of skill in the art.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

The compound can be administered orally or intravenously.

The pharmaceutical preparation can be in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, for example from about 1 mg to about 500 mg, in particular from about 1 mg to about 250 mg, or from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Schemes and Examples

Exemplary, non-limiting, chemical entities and methods useful in preparing compounds of the invention will now be described by reference to illustrative synthetic schemes for their general preparation below and the specific examples that follow. Those skilled in the art will appreciate that other synthetic routes may be used to synthesize the compounds according to the invention. Although specific starting materials and reagents are depicted and discussed herein, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Each of the reactions depicted in the reaction schemes is preferably run at a temperature from about 0° C. to the reflux temperature of the solvent used. Unless otherwise specified, the variables shown in the schemes below are as defined above in reference to Formula (I).

Compounds according to the invention may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Sigma-Aldrich Chemicals (Milwaukee, WI) or are readily prepared using methods well known to those skilled in the art (e.g., prepared by methods generally described in Louis F. Fieser and Mary Fieser, Reagents for Organic Synthesis, v. 1-23, Wiley, N.Y. (1967-2006 ed.), or Beilsteins Handbuch der organischen Chemie, 4, Aufl. ed. Springer-Verlag, Berlin, including supplements (also available via the Beilstein online database).

Synthetic chemistry transformations and protecting group methodologies (protection and deprotection) useful in synthesizing compounds according to the invention and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, 3rd Ed., John Wiley and Sons (1999); and L. Paquette, ed., Encyclopedia of Reagents for Organic Synthesis, John Wiley and Sons (1995) and subsequent editions thereof. The need for such protection will vary depending on the nature of the remote functionality and the conditions of the preparation methods. Suitable aminoprotecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art.

Additional particularly useful reactions in preparing compounds of the present invention include alkylation, reductive amination, oxidation, reduction, and hydrolysis reactions. Such transformations are well within the ordinary skill in the art.

Compounds according to the invention may be prepared singly or as compound libraries comprising, for example, at least two, or 5 to 1,000 compounds, or 10 to 100 compounds. Libraries of compounds of Formula I, II, or III may be prepared by a combinatorial "split and mix" approach or by multiple parallel syntheses using either solution phase or solid phase chemistry, by procedures known to those skilled in the art. Thus, according to a further aspect of the invention there is provided a compound library comprising at least two compounds of Formula I, II, or III, or pharmaceutically acceptable salts thereof.

In the methods of preparing compounds according to the invention, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, a-methoxy-a-(trifluoromethyl)phenyl acetate of the racemic mixture and analyzing the 1H NMR spectrum for the presence of the two atropisomeric enantiomers or diastereomers (Jacob III. J. Org. Chem. (1982) 47:4165). Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

DETAILED DESCRIPTION OF EXPERIMENTS

Synthetic Method A:

Fisher indole synthesis using beta substituted cyclic ketone and 2-carboxylate-phenyl hydrazine followed by esterification gave indole intermediate. Alkylation of indole nitrogen with the required alkyl bromide followed by hydrolysis gave rise to the desired product after purification.

Representative Example: 7-butyl-5-[(3-carbamoylphenyl)methyl]-5H,6H,7H,8H,9H,10H-cyclohepta[b]indole-4-carboxylic Acid

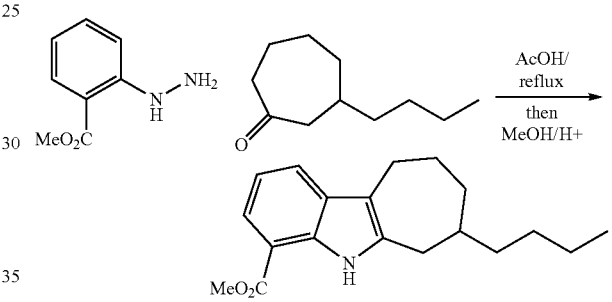

Step 1.1:

Hydrazine (1.12 g) and ketone (3 g) was mixed in AcOH and stirred at 130° C. which after 3 hr, AcOH was distilled off. Reaction was then neutralized with saturated sodium bicarbonate and extracted with EtOAc (300 mL×3) which was dried and concentrated by rotary evaporation. Purification by column chromatography (30% EtOAc:Pet Ether) gave 1 g of desired indole product.

Step 1.2:

1 g of indole was dissolved in 15 mL of MeOH. 1 mL of $H_2SO_4$ was added and heated at 80° C. After 16 hrs, MeOH was distilled off from the reaction mixture, neutralized with saturated sodium bicarbonate and extracted with EtOAc (300 mL×3) which was dried and concentrated by rotary evaporation. Purification by column chromatography (20% EtOAc:Pet Ether) gave 900 mg of desired indole ester product

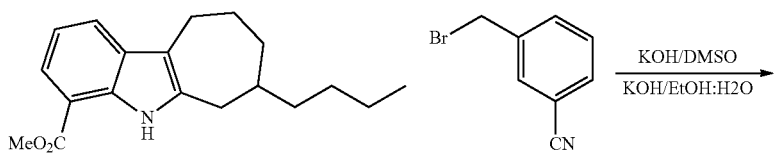

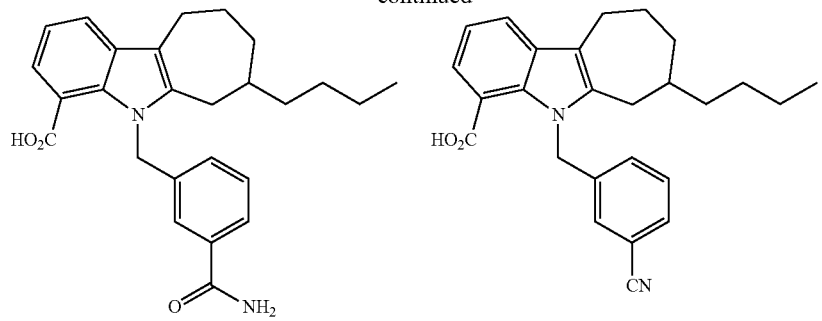

Step 2.1:

The indole ester (900 mg) and the 3-Cyano-benzyl bromide (1.18 g) was dissolved in DMSO (10 mL) and then KOH (842 mg) was added at room temperature and stirred. After 2 hr, reaction was diluted with water and extracted with EtOAc (300 mL×3) which was dried and concentrated by rotary evaporation. Purification by column chromatography (15% EtOAc:Pet Ether) gave 700 mg of desired indole ester product Step 2.2:

Benzyl indole was dissolved in EtOH:$H_2O$ (30:6 mL) and then KOH (473 mg) was added at room temperature and heated to 70° C. After 15 min, reaction was cooled to r.t., neutralized with 1N HCl solution and extracted with EtOAc (300 mL×3). Collected organic extract was then dried and concentrated by rotary evaporation. Purification by MS directed purification gave 110 mg of 7-butyl-5-[(3-cyanophenyl)methyl]-5H,6H,7H,8H,9H,10H-cyclohepta[b]indole-4-carboxylic acid and 105 mg of 7-butyl-5-[(3-carbamoylphenyl)methyl]-5H,6H,7H,8H,9H,10H-cyclohepta[b]indole-4-carboxylic acid.

Synthetic Method B:

Fisher indole synthesis using an unsubstituted cyclic ketone and 2-carboxylate-phenyl hydrazine followed by esterification gave indole intermediate. TFAA-DMSO alkylation protocol (Masanori Tayu et al., *Org. Biomol. Chem.* (2013) 1_496) with the required nucleophile followed by ester hydrolysis gave rise to the desired product after purification.

Representative Example: 9-[(3-carbamoylphenyl)methyl]-2-pentyl-2,3,4,9-tetrahydro-1H-carbazole-8-carboxylic Acid

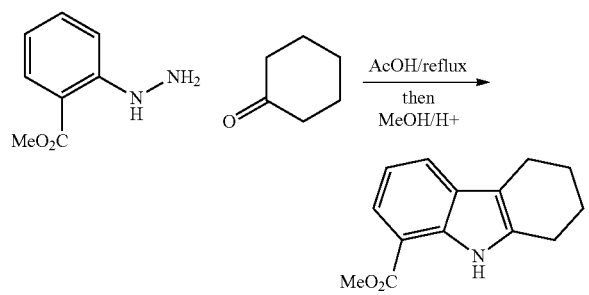

Step 1.1:

Hydrazine (6.0 g) and ketone (6.2 g) was mixed in AcOH (100 mL) and stirred at 130° C. which after 3 hr, AcOH was distilled off. Reaction was then neutralized with saturated sodium bicarbonate and extracted with EtOAc (300 mL×3) which was dried and concentrated by rotary evaporation. Purification by column chromatography (30% EtOAc:Pet Ether) gave 5 g of desired indole product.

Step 1.2:

5 g of indole was dissolved in 100 mL of MeOH. 7 mL of concentrated $H_2SO_4$ was added and heated at 80° C. After 16 hours, MeOH was distilled off from the reaction mixture, neutralized with saturated sodium bicarbonate and extracted with EtOAc (300 mL×3) which was dried and concentrated by rotary evaporation. Purification by column chromatography (20% EtOAc:Pet Ether) gave 4.2 g of desired indole ester product.

Step 2:

The indole ester (3 g) was dissolved in DMSO (50 mL) and then KOH (3.675 g) was added at room temperature. 3-Cyano-benzyl bromide (5.13 g) was then added in portions and stirred. After 2 hr, reaction slowly poured into 1N HCl in flask with ice bath and then the organics were extracted with EtOAc (300 mL×3) which was dried and concentrated by rotary evaporation. Purification by column chromatography (20% EtOAc:Pet Ether) gave 3.5 g of desired indole ester product

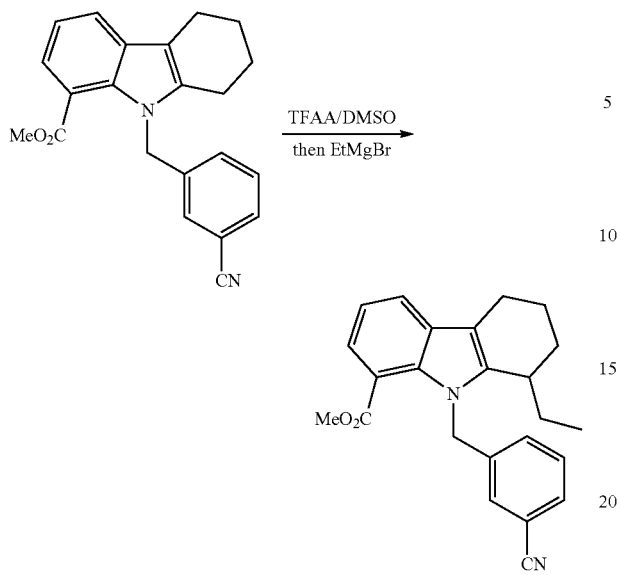

Step 3:
To the solution of indole ester (500 mg) in dichloromethane (7 mL) at −40° C., was added DMSO (0.315 mL). to this mixture, Trifluoro-acetic anhydride (0.617 mL) was added dropwise and stirred at −40° C. After 1 hr, ethyl magnesium bromide (17.647 mL, 1M) was added dropwise to this mixture. After 2 hrs, the reaction was slowly poured into a solution of 10 mL of saturated NaHCO3+20 mL H2O+30 mL of EtOAc. Organic layer was separated and dried and concentrated in vacuo. Purification by column chromatography (20% EtOAc:Pet Ether) gave 300 mg of desired product Step 4:
Benzyl indole (150 mg) was dissolved in EtOH:H2O (5:2 mL) and then KOH (156 mg) was added at room temperature and stirred. After 16 hrs, reaction neutralized with 1N HCl solution and solid was filtered as 9-[(3-carbamoylphenyl)methyl]-2-pentyl-2,3,4,9-tetrahydro-1H-carbazole-8-carboxylic acid (30 mg).

Technical outcomes of the above are reflected in Table 1 below:

TABLE 1

| IUPAC Name | 1H NMR | Exact Mass (g) | Observed [M + H]/Z | Synthetic Method |
|---|---|---|---|---|
| 5-[(3-cyanophenyl)methyl]-2-fluoro-7-hexyl-5H,6H,7H,8H,9H,10H-cyclohepta[b]-indole-4-carboxylic acid | 1H-NMR (400 MHz, DMSO-d6): _ 13.1 (brs, 1H), 7.68-7.66 (m, 1H), 7.52-7.49 (m, 1H), 7.45 (t, J = 7.6 Hz, 1H), 7.30 (s, 1H), 7.18-7.15 (m, 1H), 6.97 (d, J = 8.0 Hz, 1H), 5.79-5.74 (m, 1H), 5.61-5.56 (m, 1H), 2.90-2.80 (m, 2H), 2.51-2.50 (m, 2H), 1.91-1.84 (m, 2H), 1.54-1.49 (m, 2H), 1.36 (brs, 1H), 1.23-0.91 (m, 10H), 0.83 (t, J = 7.2 Hz, 3H), | 446.24 | MS (ESI) m/z: 446 [M + H]+ | Compound was synthesized by method A using 3-hexyl-1-cycloheptanone and 2-cyano-1-benzyl bromide as appropriate building blocks |
| 5-[(6-cyanopyridin-2-yl)methyl]-7-hexyl-5H,6H,7H,8H,9H,10H-cyclohepta[b]-indole-4-carboxylic acid | 1H-NMR (400 MHz, DMSO-d6): _ 12.8 (S, 1H), 7.94-7.88 (m, 2H), 7.69 (d, J = 8.00 Hz, 1H), 7.43 (d, J = 3.27 Hz, 1H), 7.07 (t, J = 7.60 Hz, 1H), 6.81-6.79 (m, 1H), 5.85 (d, J = 18.00 Hz, 1H), 5.63 (d, J = 18.40 Hz, 1H), 2.94-2.89 (m, 1H), 2.87-2.67 (m, 2H), 1.93-1.87 (m, 2H), 1.53-1.50 (m, 2H), 1.41-1.24 (m, 1H), 1.19-1.09 (m, 9H), 1.01-0.99 (m, 2H), 0.831 (t, J = 7.2 Hz, 3H), | 429.24 | MS (ESI) m/z: 430 (M + H) + | Compound was synthesized by method A using 3-hexyl-1-cycloheptanone and 2-(bromomethyl)-6-isocyanopyridine as appropriate building blocks |
| 5-[(6-carbamoylpyridin-2-yl)methyl]-7-hexyl-5H,6H,7H,8H,9H,10H-cyclohepta[b]-indole-4-carboxylic acid | 1H-NMR (400 MHz, DMSO-d6): _ 12.5 (s, 1H), 7.83 (d, J = 4.40 Hz, 2H), 7.69-7.62 (m, 3H), 7.43 (d, J = 0.80 Hz, 1H), 7.06 (t, J = 7.60 Hz, 1H), 6.84 (t, J = 4.40 Hz, 1H), 5.90 (d, J = 17.60 Hz, 1H), 5.68 (d, J = 17.60 Hz, 1H), 2.92-2.86 (m, 2H), 2.71-2.65 (m, 1H), 1.92-1.84 (m, 2H), 1.55-1.49 (m, 2H), 1.24-0.94 (m, 12H), 0.81 (t, J = 7.20 Hz, 3H) | 447.25 | MS (ESI) m/z: 448 (M + H) +. | Compound was synthesized by method A using 3-hexyl-1-cycloheptanone and 2-cyano-1-benzyl bromide as appropriate building blocks |

TABLE 1-continued

| IUPAC Name | 1H NMR | Exact Mass (g) | Observed [M + H]/Z | Synthetic Method |
|---|---|---|---|---|
| 6-({4-carboxy-7-hexyl-5H,6H,7H,8H,9H,10H-cyclohepta[b]-indol-5-yl}methyl)-pyridine-2-carboxylic acid | 1H-NMR (400 MHz, DMSO-d6):_ 7.67-7.27 (m, 2H), 7.41 (d, J = 7.60 Hz, 1H), 7.15 (d, J = 7.20 Hz, 1H), 6.93 (t, J = 7.60 Hz, 2H), 5.81 (d, J = 16.00 Hz, 1H), 5.64 (d, J = 16.40 Hz, 1H), 2.89 (d, J = 42.40 Hz, 1H), 2.82-2.67 (m, 1H), 2.65-2.56 (m, 2H), 1.91 (t, J = 4.40 Hz, 1H), 1.81 (d, J = 8.80 Hz, 1H), 1.52 (t, J = 7.60 Hz, 3H), 1.23-1.15 (m, 10H), 0.84 (t, J = 6.80 Hz, 3H), | 448.24 | MS (ESI) m/z: 447 (M − H)−. | Compound was synthesized by method A using 3-hexyl-1-cycloheptanone and 2-cyano-1-benzyl bromide as appropriate building blocks |
| 5-[(3-cyano-2-fluorophenyl)-methyl]-7-hexyl-5H,6H,7H,8H,9H,10H-cyclohepta[b]-indole-4-carboxylic acid | 1H-NMR (400 MHz, DMSO-d6): _ 12.86 (s, 1H), 7.79-7.76 (m, 1H), 7.69 (d, J = 7.60 Hz, 1H), 7.41 (d, J = 7.20 Hz, 1H), 7.23-7.19 (m, 1H), 7.08-7.04 (m, 1H), 6.53-6.50 (m, 1H), 5.86-5.65 (m, 2H), 2.94-2.89 (m, 1H), 2.81-2.72 (m, 1H), 2.72-2.67 (m, 1H), 1.93-1.87 (m, 2H), 1.55-1.43 (m, 4H), 1.15-1.00 (m, 10H), 0.82 (t, J = 7.20 Hz, 3H), | 446.24 | MS (ESI) m/z: 447 [M + H]+. | Compound was synthesized by method A using 3-hexyl-1-cycloheptanone and 1-cyano-2-fluoro--3-benzyl bromide as appropriate building blocks |
| 5-[(1,3-benzoxazol-6-yl)methyl]-7-hexyl-5H,6H,7H,8H,9H,10H-cyclohepta[b]-indole-4-carboxylic acid | 1H-NMR (400 MHz, DMSO-d6): _ 12.90 (s, 1H), 8.66 (s, 1H), 7.64-7.70 (m, 2H), 7.38-7.40 (m, 1H), 7.04-7.08 (m, 2H), 6.79-6.82 (m, 1H), 5.90 (d, J = 18.00 Hz, 1H), 5.71 (d, J = 17.60 Hz, 1H), 2.84-2.93 (m, 2H), 2.67-2.73 (m, 1H), 1.85-1.91 (m, 2H), 1.37-1.56 (m, 3H), 1.06-1.10 (m, 5H), 0.75-0.96 (m, 9H), | 444.24 | MS (ESI) m/z: 444.9 [M + H]+. | Compound was synthesized by method A using 3-hexyl-1-cycloheptanone and 6-(bromomethyl)-benzo[d]oxazole as appropriate building blocks |
| 5-[(1,3-benzoxazol-5-yl)methyl]-7-hexyl-5H,6H,7H,8H,9H,10H-cyclohepta[b]-indole-4-carboxylic acid | 1H-NMR (400 MHz, DMSO-d6): _ 12.90 (s, 1H), 8.68 (s, 1H), 7.60-7.69 (m, 2H), 7.38 (d, J = 6.80 Hz, 1H), 7.01-7.07 (m, 2H), 6.87-6.89 (m, 1H), 5.89 (d, J = 17.20 Hz, 1H), 5.70 (d, J = 17.60 Hz, 1H), 2.85-2.89 (m, 2H), 2.67-2.68 (m, 1H), 1.88-1.91 (m, 2H), 1.49-1.54 (m, 2H), 1.24-1.45 (m, 2H), 0.95-1.10 (m, 13H), 0.77 (t, J = 7.60 Hz, 3H); | 444.24 | MS (ESI) m/z: 445 [M + H]+. | Compound was synthesized by method A using 3-hexyl-1-cycloheptanone and 5-(bromomethyl)-benzo[d]oxazole as appropriate building blocks |
| 5-[(6-fluoropyridin-2-yl)methyl]-7-hexyl-5H,6H,7H,8H,9H,10H-cyclohepta[b]-indole-4-carboxylic acid | 1H-NMR (400 MHz, DMSO-d6): _ 12.86 (s, 1H), 7.85-7.78 (m, 1H), 7.68 (d, J = 7.2 Hz, 1H), 7.41 (d, J = 7.20 Hz, 1H), 7.08-7.04 (m, 1H), 6.98 (d, J = 7.60 Hz, 1H), 6.35 (d, J = 6.80 Hz, 1H), 5.81-5.76 (m, 1H), 5.58-5.53 (m, 1H), 2.94-2.89 (m, 1H), 2.82-2.78 (m, 1H), 2.72-2.66 (m, 2H), 1.93-1.87 (m, 2H), 1.57-1.45 (m, 3H), 1.19-0.98 (m, 11H), 0.82 (t, J = 6.80 Hz, 3H) | 422.24 | m/z: 423 [M + H]+. | Compound was synthesized by method A using 3-hexyl-1-cycloheptanone and 6-fluoro-pyridine-2-benzyl bromide as appropriate building blocks |
| 5-[(2-fluoropyridin-4-yl)methyl]-7-hexyl-5H,6H,7H,8H,9H,10H-cyclohepta[b]-indole-4-carboxylic acid | 1H-NMR (400 MHz, DMSO-d6): _ 12.8 (s, 1H), 7.83 (d, J = 4.40 Hz, 1H), 8.09 (d, J = 5.20 Hz, 1H), 7.44 (d, J = 6.40 Hz, 1H), 7.08 (t, J = 7.60 Hz, 1H), 7.08 (d, J = 7.60 Hz, 1H), 6.52 (s, 1H), 5.83 (d, J = 18.80 Hz, 1H), 5.65 (d, J = 18.40 Hz, 1H), 2.90-2.88 (m, 1H), 2.76-2.66 (m, 2H), 1.93-1.86 (m, 2H), 1.57-1.178 (m, 3H), 1.20-1.03 (m, 11H), 0.83(t, J = 7.2 Hz, 3H); | 422.24 | MS (ESI) m/z: 421 [M − H]−. | Compound was synthesized by method A using 3-hexyl-1-cycloheptanone and 6-fluoro-pyridine-4-benzyl bromide as appropriate building blocks |
| 7-hexyl-5-{[6-(trifluoromethyl)-pyridin-2-yl]methyl}-5H,6H,7H,8H,9H,10H-cyclohepta[b]-indole-4-carboxylic acid | 1H-NMR (400 MHz, DMSO-d6): _ 12.92 (brs, 1H), 7.94 (t, J = 8.0 Hz, 1H), 7.75-7.69 (m, 2H), 7.45 (dd, J = 1.2, 7.2 Hz, 1H), 7.08 (t, J = 7.6 Hz, 1H), 6.72 (d, J = 8.0 Hz, 1H), 5.89-5.85 (m, 1H), 5.67-5.62 (m, 1H), 2.96-2.91 (m, 1H), 2.76-2.64 (m, 1H), 2.50-2.49 (m, 1H), 1.92-1.89 (m, 2H), 1.55-1.48 (m, 2H), 1.38 ( brs, 1H), 1.16-1.00 (m, 9H), 0.93-0.89 (m, 2H), 0.80 (t, J = 7.2 Hz, 3H), | 472.23 | MS (ESI) m/z: 473 [M + H]+. | Compound was synthesized by method A using 3-hexyl-1-cycloheptanone and 2-(bromomethyl)-6-(trifluoromethyl)-pyridine as appropriate building blocks |
| 7-hexyl-5-{2-(trifluoromethyl)-pyridin-4-yl]ethyl}-5H,6H,7H,8H,9H,10H-cyclohepta[b]- | 1H-NMR (400 MHz, DMSO-d6): _12.89 (brs, 1H), 8.62 (d, J = 4.8 Hz, 1H), 7.72 (d, J = 8.0 Hz, 1H), 7.47-7.43 (m, 2H), 7.09 (t, J = 7.6 Hz, 1H), 6.99-6.98 (m, 1H), 5.89-5.84 (m, 1H), 5.69-5.65 (m, 1H), 2.95-2.90 (m, 1H), | 472.23 | MS (ESI) m/z: 472.9 [M + H]+. | Compound was synthesized by method A using 3-hexyl-1-cycloheptanone and 2-trifluoromethyl- |

TABLE 1-continued

| IUPAC Name | 1H NMR | Exact Mass (g) | Observed [M + H]/Z | Synthetic Method |
|---|---|---|---|---|
| cyclohepta[b]-indole-4-carboxylic acid | 2.72-2.68 (m, 2H), 1.93-1.87 (m, 2H), 1.55-1.50 (m, 2H), 1.36 (brs, 1H), 1.16-1.11 (m, 2H), 1.09-0.89 (m, 7H), 0.80 (t, J = 7.2 Hz, 3H), | | | pyridine-4-benzyl bromide as appropriate building blocks |
| 5-[(5-cyanopyridin-3-yl)methyl]-7-hexyl-5H,6H,7H,8H,9H,10H-cyclohepta[b]-indole-4-carboxylic acid | 1H-NMR (400 MHz, DMSO-d6): _ 12.90 (s, 1H), 8.88 (d, J = 1.60 Hz, 1H), 8.23 (d, J = 2.00 Hz, 1H), 7.70-7.74 (m, 2H), 7.44 (d, J = 6.80 Hz, 1H), 7.08 (m, 1H), 5.77 (d, J = 18.40 Hz, 1H), 5.62 (d, J = 18.00 Hz, 1H), 2.67-2.93 (m, 3H), 1.85-1.93 (m, 2H), 1.41-1.57 (m, 3H), 0.83-1.24 (m, 14H), | 429.24 | MS (ESI) m/z: 430 [M + H]+. | Compound was synthesized by method A using 3-hexyl-1-cycloheptanone and 5-(bromomethyl)-nicotinonitrile as appropriate building blocks |
| 5-[(5-cyanothiophen-2-yl)methyl]-7-hexyl-5H,6H,7H,8H,9H,10H-cyclohepta[b]-indole-4-carboxylic acid | 1H-NMR (400 MHz, DMSO-d6): _ 13.04 (s, 1H), 7.75 (d, J = 3.60 Hz, 1H), 7.69 (d, J = 7.20 Hz, 1H), 7.50 (d, J = 7.20 Hz, 1H), 7.08 (t, J = 7.60 Hz, 1H), 6.78 (d, J = 4.00 Hz, 1H), 6.01 (d, J = 18.00 Hz, 1H), 5.86 (d, J = 18.00 Hz, 1H), 2.85-2.94 (m, 2H), 2.51-2.70 (m, 3H), 1.84-1.97 (m, 2H), 1.52-1.54 (m, 3H), 1.16-1.23 (m, 9H), 0.85 (t, J = 7.20 Hz, 3H), | 434.20 | MS (ESI) m/z: 433.3 [M − H]−. | Compound was synthesized by method A using 3-hexyl-1-cycloheptanone and 5-(bromomethyl)-thiophene-2-carbonitrile as appropriate building blocks |
| 5-[(4-cyanothiophen-2-yl)methyl]-7-hexyl-5H,6H,7H,8H 9H,10H-cyclohepta[b]-indole-4-carboxylic acid | 1H-NMR (400 MHz, DMSO-d6): _ 13.0(s, 1H), 8.31 (s, J = 1.2 Hz, 1H), 7.66 (d, J = 6.8 Hz, 1H), 7.49-7.47 (m, 1H), 7.08-7.04 (m, 2H), 5.94 (d, J = 18, 1H), 5.80 (d, J = 17.2 Hz, 1H), 2.96 (d, J = 15.6 Hz, 1H), 2.89-2.84 (m, 1H), 2.62-2.58 (m, 2H), 1.96-1.84 (m, 2H), 1.55-1.50 (m, 3H), 1.23-1.18 (m, 10H), 0.85 (t, J = 6.4, 3H); | 434.20 | MS (ESI) m/z: 433 [M − H]−. | Compound was synthesized by method A using 3-hexyl-1-cycloheptanone and 5-(bromomethyl)-thiophene-3-carbonitrile as appropriate building blocks |
| 5-[(5-cyanofuran-2-yl)methyl]-7-hexyl-5H,6H,7H,8H,9H,10H-cyclohepta[b]-indole-4-carboxylic acid | 1H-NMR (400 MHz, DMSO-d6): _ 13.10 (s, 1H), 7.66 (d, J = 7.20 Hz, 1H), 7.46 (t, J = 3.60 Hz, 2H), 7.06 (t, J = 7.60 Hz, 1H), 6.12 (d, J = 3.60 Hz, 1H), 5.87 (d, J = 18.00 Hz, 1H), 5.71 (d, J = 18.00 Hz, 1H), 2.84-3.03 (m, 2H), 2.60-2.70 (m, 1H), 1.85-1.97 (m, 2H), 1.55-1.57 (m, 3H), 1.23-1.27 (m, 11H), 0.85 (t, J = 6.80 Hz, 3H); | 418.23 | MS (ESI) m/z: 417 [M − H]−. | Compound was synthesized by method A using 3-hexyl-1-cycloheptanone and 5-(bromomethyl)-furan-2-carbonitrile as appropriate building blocks |
| 5-[(3,5-dimethyl-1,2-oxazol-4-yl)methyl]-7-hexyl-5H,6H,7H,8H,9H,10H-cyclohepta[b]-indole-4-carboxylic acid | 1H-NMR (400 MHz, DMSO-d6): _ 12.79 (s, 1H), 7.66-7.68 (m, 1H), 7.38-7.40 (m, 1H), 7.04 (t, J = 7.60 Hz, 1H), 5.38 (d, J = 17.20 Hz, 1H), 5.30 (d, J = 17.20 Hz, 1H), 2.86-2.90 (m, 2H), 2.67-2.68 (m, 1H), 1.85-1.97 (m, 2H), 1.77 (s, 3H), 1.63 (s, 3H), 1.51-1.53 (m, 3H), 1.22-1.30 (m, 11H), 0.85 (t, J = 7.20 Hz, 3H), | 422.26 | MS (ESI) m/z: 423 [M + H]+. | Compound was synthesized by method A using 3-hexyl-1-cycloheptanone and 4-(bromomethyl)-3,5-dimethylisoxazole as appropriate building blocks |
| 5-(3-cyanobenzoyl)-7-hexyl-5H,6H,7H,8H,9H,10H-cyclohepta[b]-indole-4-carboxylic acid | 1H-NMR (400 MHz, DMSO-d6): _ 12.90 (s, 1H), 8.10-8.12 (m, 1H), 7.92 (s, 1H), 7.82-7.84 (m, 1H), 7.67 (t, J = 7.60 Hz, 1H), 7.53-7.57 (m, 2H), 7.26 (t, J = 7.60 Hz, 1H), 2.57-2.88 (m, 4H), 1.84-1.93 (m, 2H), 1.57-1.63 (m, 3H), 1.24-1.25 (m, 1H), 0.80-1.15 (m, 12H), | 442.23 | MS (ESI) m/z: 441 [M − H]−. | Compound was synthesized by method A using 3-hexyl-1-cycloheptanone and 2-cyano-1-benzyl bromide as appropriate building blocks |
| 5-[(1,3-benzoxazol-7-yl)methyl]-7-hexyl-5H,6H,7H,8H,9H,10H-cyclohepta[b]-indole-4-carboxylic acid | 1H-NMR (400 MHz, DMSO-d6): _ 12.90 (s, 1H), 8.78 (s, 1H), 7.70 (d, J = 7.60 Hz, 1H), 7.61 (d, J = 7.60 Hz, 1H), 7.40 (d, J = 7.60 Hz, 1H), 7.17 (t, J = 8.00 Hz, 1H), 7.06 (t, J = 7.60 Hz, 1H), 6.27 (d, J = 7.60 Hz, 1H), 6.09 (d, J = 18.40 Hz, 1H), 5.90 (d, J = 18.40 Hz, 1H), 2.83-2.95 (m, 2H), 2.67-2.73 (m, 1H), 1.89-1.91 (m, 2H), 1.40-1.57 (m, 3H), 1.24-1.26 (m, 1H), 1.08-1.13 (m, 4H), 0.86-1.01 (m, 6H), 0.79 (t, J = 7.20 Hz, 3H). | 444.24 | MS (ESI) m/z: 445 [M +H]+30. | Compound was synthesized by method A using 3-hexyl-1-cycloheptanone and 7-(bromomethyl)-benzo[d]oxazole as appropriate building blocks |
| 5-[(5-cyanothiophen-3-yl)methyl]-7- | 1H-NMR (400 MHz, DMSO-d6): _ 12.95 (s, 1H), 7.69-7.61 (m, 1H), 7.51 (s, 1H), 7.42-7.40 (m, 1H), 7.18 (s, | 434.20 | MS (ESI) m/z: 435.0 [M + H]+ | Compound was synthesized by method A using 3- |

TABLE 1-continued

| IUPAC Name | 1H NMR | Exact Mass (g) | Observed [M + H]/Z | Synthetic Method |
|---|---|---|---|---|
| hexyl-5H,6H,7H,8H,9H,10H-cyclohepta[b]-indole-4-carboxylic acid | 1H), 7.07-7.03 (m, 1H), 5.73-5.69 (m, 1H), 5.57-5.53 (m, 1H), 2.90-2.83 (m, 1H), 2.73-2.65 (m, 2H), 2.57-2.54 (m, 1H), 1.93-1.84 (m, 2H), 1.54-1.45 (m, 3H), 1.24-1.14 (m, 10H), 0.85 (t, J = 7.20 Hz, 3H). | | | hexyl-1-cycloheptanone and methyl 5-((5-cyanothiophen-3-yl) methyl) bromide as appropriate building blocks |
| 7-hexyl-5-[(1H-indol-4-yl)methyl]-5H,6H,7H,8H,9H,10H-cyclohepta[b]-indole-4-carboxylic acid | 1H-NMR (400 MHz, DMSO-d6): _ 12.75 (bs, 1H), 11.11 (bs, 1H), 7.68 (d, J = 7.20 Hz, 1H), 7.37 (d, J = 6.80 Hz, 1H), 7.30 (t, J = 2.80 Hz, 1H), 7.19 (d, J = 8.00 Hz, 1H), 7.04 (t, J = 7.60 Hz, 1H), 6.80 (t, J = 8.00 Hz, 1H), 6.35 (s, 1H), 6.02 (d, J = 18.00 Hz, 1H), 5.85 (s, 1H), 5.81 (d, J = 6.80 Hz, 1H), 2.93-2.89 (m, 1H), 2.81-2.77 (m, 1H), 2.71-2.67 (m, 1H), 2.42-2.36 (m, 1H), 1.88-1.86 (m, 2H), 1.54-1.44 (m, 2H), 1.31-1.20 (m, 2H), 1.15-1.09 (m, 1H), 1.02-0.92 (m, 6H), 0.89-0.78 (m, 5H). | 442.26 | MS (ESI) m/z: 443.3 [M + H]+. | Compound was synthesized by method A using 3-hexyl-1-cycloheptanone and methyl 5-((1-(tert-butoxy carbonyl)-1H-indol-4-yl) bromide as appropriate building blocks |
| 5-[(3-carbamoylphenyl)-methyl]-7-propyl-5H,6H,7H,8H,9H,10H-cyclohepta[b]-indole-4-carboxylic acid | 400 MHz-DMSO d6: 12.84(br s, 1H), 7.87 (br s, 1H), 7.67 (d, J = 8 Hz, 2H), 7.52 ( s, 1H), 7.38 (d, J = 7.2 Hz, 1H), 7.29(br s, 1H), 7.26 ( t, J = 8 Hz, 1H), 7.04 ( t, J = 8 Hz, 1H), 6.72(d, J = 8 Hz, 1H), 5.79 ( d, J = 18 Hz, 1H), 5.60( d, J = 18 Hz, 1H), 2.93-2.81 ( m, 2H), 2.72-2.66(m, 1H), 2.46 (m, 1H), 1.92-1.85 (m, 2H), 1.55-1.47(m, 3H), 1.11-1.02(m, 4H), 0.71-0.70 (m, 3H) | 404.21 | 405.1 | Compound was synthesized by method A using 3-propyl-1-cycloheptanone and 3-cyano-1-benzyl bromide as appropriate building blocks |
| 7-butyl-5-[(3-carbamoylphenyl)-methyl]-5H,6H,7H,8H,9H,10H-cyclohepta[b]-indole-4-carboxylic acid | 400 MHz-DMSO d6: 12.85(br s, 1H), 7.88 (br s, 1H), 7.68 (d, J = 8 Hz, 2H), 7.53 ( s, 1H), 7.38 (d, J = 7.2 Hz, 1H), 7.31 (br s, 1H), 7.26 ( t, J = 8 Hz, 1H), 7.05 ( t, J = 8 Hz, 1H), 6.71(d, J = 8 Hz, 1H), 5.80 ( d, J = 17 Hz, 1H), 5.60( d, J = 17 Hz, 1H), 2.93-2.88 (m, 1H), 2.82(d, J = 16 Hz, 1H), 2.72-2.66 (m, 1H), 2.46 (m, 1H), 1.92-1.85 (m, 2H), 1.55-1.47(m, 2H), 1.45-1.36(m, 1H), 1.11-0.95(m, 6H), 0.74 (t, J = 7 Hz, 3H) | 418.23 | 419.1 | Compound was synthesized by method A using 3-butyl-1-cycloheptanone and 3-cyano-1-benzyl bromide as appropriate building blocks |
| 7-butyl-5-[(3-cyanophenyl)-methyl]-5H,6H,7H,8H,9H,10H-cyclohepta[b]-indole-4-carboxylic acid | 400 MHz-DMSO d6: 12.87(br s, 1H), 7.69 (t, J = 8 Hz, 2H), 7.45 ( t, J = 8 Hz, 1H), 7.41(d, J = 8 Hz, 1), 7.29 (br s, 1H), 7.07 ( t, J = 8 Hz, 1H), 6.99 (d, J = 8 Hz, 1H), 5.78 ( d, J = 18 Hz, 1H), 5.60( d, J = 18 Hz, 1H), 2.93-2.88 (m, 1H), 2.78(d, J = 16 Hz, 1H), 2.72-2.67(m, 1H), 2.46 (m, 1H), 1.92-1.86 (m, 2H), 1.55-1.37(m, 2H), 1.4-1.30(m, 1H), 1.11-0.95(m, 6H), 0.76 (t, J = 7 Hz, 3H) | 400.22 | 401.1 | Compound was synthesized by method A using 3-propyl-1-cycloheptanone and 3-cyano-1-benzyl bromide as appropriate building blocks |
| 7-butyl-5-[(pyridin-3-yl)methyl]-5H,6H,7H,8H,9H,10H-cyclohepta[b]-indole-4-carboxylic acid | 400 MHz-DMSO d6: 12.84(br s, 1H), 8.38(s, 1H), 8.07(s, 1H), 7.69 (dd, J = 8.0, 0.8 Hz, 1H), 7.41 (dd, J = 8.0, 0.8 Hz, 1H), 7.26-7.23 (m, 1H), 7.08-7.04 (m, 2H), 5.76 ( d, J = 17.6 Hz, 1H), 5.62( d, J = 17.6 Hz, 1H), 2.93-2.84 (m, 2H), 2.73-2.66(m, 1H), 2.57-2.53 (m, 1H), 1.94-1.84 (m, 2H), 1.58-1.44(m, 3H), 1.25-1.02 (m, 6H), 0.77 (t, J = 6.8 Hz, 3H) | 376.22 | 377.23 | Compound was synthesized by method A using 3-butyl-1-cycloheptanone and 3-benzyl bromo-pyridine as appropriate building blocks |
| 7-butyl-5-[(3-methylphenyl)methyl]-5H,6H,7H,8H,9H,10H-cyclohepta[b]-indole-4-carboxylic acid | 400 MHz-DMSO d6: 12.85(br s, 1H), 7.66(d, J = 8 Hz, 1H), 7.37 (d, J = 8 Hz, 1H), 7.05 (m, 2H), 6.96 (d, J = 8 Hz, 1H), 6.70 (s, 1H), 6.44(d, J = 7.2 Hz, 1H), 5.72 (d, J = 17.6 Hz, 1H), 5.52 ( d, J = 17.6 Hz, 1H), 2.93-2.85 (m, 2H), 2.71-2.65 (m, 1H), 2.50 (m, 1H), 2.185 (s, 3H), 1.94-1.84 (m, 2H), 1.58-1.47 (m, 2H), 1.45-1.36 (m, 1H), 1.18-0.95(m, 6H), 0.77 (t, J = 6.8 Hz, 3H) | 389.24 | 390.1 | Compound was synthesized by method A using 3-butyl-1-cycloheptanone and 3-methyl-1-benzyl bromide as appropriate building blocks |
| 7-butyl-5-[(3-methoxyphenyl)-methyl]-5H,6H,7H,8H, | 400 MHz-DMSO d6: 12.85(br s, 1H), 7.66(d, J = 8 Hz, 1H), 7.37 (d, J = 8 Hz, 1H), 7.11 (t, J = 8 Hz, 1H), 7.04 (t, J = 8 Hz, 1H), 6.71 (m, 1H), 6.31-6.26 | 405.23 | 406.1 | Compound was synthesized by method A using 3-butyl-1- |

TABLE 1-continued

| IUPAC Name | 1H NMR | Exact Mass (g) | Observed [M + H]/Z | Synthetic Method |
|---|---|---|---|---|
| 9H,10H-cyclohepta[b]-indole-4-carboxylic acid | (m, 2H), 5.73 (d, J = 17.6 Hz, 1H), 5.54 (d, J = 17.6 Hz, 1H), 3.62 (s, 3H), 2.93-2.85 (m, 2H), 2.71-2.65 (m, 1H), 2.50 (m, 1H), 1.94-1.84 (m, 2H), 1.58-1.47 (m, 2H), 1.45-1.36 (m, 1H), 1.18-0.95(m, 6H), 0.77 (t, J = 6.8 Hz, 3H) | | | cycloheptanone and 3-methoxy-1-benzyl bromide as appropriate building blocks |
| 7-butyl-5-[(3-chlorophenyl)methyl]-5H,6H,7H,8H,9H,10H-cyclohepta[b]-indole-4-carboxylic acid | 400 MHz-DMSO d6: 12.86(br s, 1H), 7.68 (d, J = 7.2 Hz, 1H), 7.40 (d, J = 7.2 Hz, 1H), 7.27-7.21 (m, 2H), 7.04(t, J = 8 Hz, 1H), 6.84 (s, 1H), 6.67 (d, J = 6.4 Hz, 1H), 5.77 (d, J = 17.6 Hz, 1H), 5.57( d, J = 17.6 Hz, 1H), 2.93-2.87 (m, 1H), 2.83 (d, J = 16 Hz, 1H), 2.68-2.66(m, 1H), 2.47 (m, 1H), 1.93-1.87 (m, 2H), 1.58-1.48(m, 2H), 1.44-1.33(m, 1H), 1.21-0.95(m, 6H), 0.77 (t, J = 6.8 Hz, 3H) | 409.18 | 410.1 | Compound was synthesized by method A using 3-butyl-1-cycloheptanone and 3-chloro-1-benzyl bromide as appropriate building blocks |
| 7-butyl-5-[(3-hydroxyphenyl)-methyl]-5H,6H,7H,8H,9H,10H-cyclohepta[b]-indole-4-carboxylic acid | 400 MHz-DMSO d6: 12.85(br s, 1H), 9.19(s, 1H), 7.65(d, J = 7.6 Hz, 1H), 7.37 (d, J = 7.6 Hz, 1H), 7.05-6.97(m, 2H), 6.52 (d, J = 6.4 Hz, 1H), 6.22 (d, J = 7.6 Hz, 1H), 6.10(s, 1H), 5.68 (d, J = 17.6 Hz, 1H), 5.50 ( d, J = 17.6 Hz, 1H), 2.97-2.83 (m, 3H), 2.71-2.65 (m, 1H), 1.94-1.84 (m, 2H), 1.58-1.47 (m, 3H), 1.25-1.20 (m, 2H), 1.18-1.00(m, 6H), 0.78 (t, J = 6.8 Hz, 3H) | 391.21 | 392.46 | Compound was synthesized by method A using 3-butyl-1-cycloheptanone and 3-hydroxyl-1-benzyl bromide as appropriate building blocks |
| 7-butyl-5-[(2-methoxypyridin-4-yl)methyl]-5H,6H,7H,8H,9H,10H-cyclohepta[b]-indole-4-carboxylic acid | 400 MHz-DMSO d6: 12.85(br s, 1H), 8.00(d, J = 5.2 Hz, 1H), 7.69 (d, J = 7.2 Hz, 1H), 7.42 (d, J = 6.8 Hz, 1H), 7.06 (t, J = 7.2 Hz, 1H), 6.41 (d, J = 4.4 Hz, 1H), 6.00 (s, 1H), 5.75 (d, J = 17.6 Hz, 1H), 5.57 ( d, J = 17.6 Hz, 1H), 3.74 (s, 3H), 2.93-2.86 (m, 1H), 2.79-2.65 (m, 2H), 2.50 (m, 1H), 1.94-1.84 (m, 2H), 1.58-1.47 (m, 3H), 1.18-0.99(m, 6H), 0.75 (t, J = 6.8 Hz, 3H) | 406.23 | 407 | Compound was synthesized by method A using 3-butyl-1-cycloheptanone and 2-methoxy-4-benzyl bromide-pyridine as appropriate building blocks |
| 7-butyl-5-[(4-carbamoylphenyl)-methyl]-5H,6H,7H,8H,9H,10H-cyclohepta[b]-indole-4-carboxylic acid | 400 MHz-DMSO d6: 12.85 (br s, 1H), 7.83 (s, 1H), 7.72-7.67(m, 3H), 7.39 (d, J = 10.8 Hz, 1H), 7.26 (s, 1H), 7.05 (t, J = 8 Hz, 1H), 6.79 (d, J = 7.6 Hz, 2H), 5.80 (d, J = 18.4 Hz, 1H), 5.62( d, J = 18.4 Hz, 1H), 2.90 (dd, J = 16, 7.2 Hz, 1H), 2.82( d, J = 15.6 Hz, 1H), 2.69 (dd, J = 16, 7.2 Hz, 1H), 2.47 (m, 1H), 1.93-1.87 (m, 2H), 1.56-1.48 (m, 2H), 1.42-1.35 (m, 1H), 1.15-0.98(m, 6H), 0.74 (t, J = 6.8 Hz, 3H) | 418.23 | 419.1 | Compound was synthesized by method A using 3-butyl-1-cycloheptanone and 4-amide-1-benzyl bromide as appropriate building blocks |
| 7-butyl-5-[(2-carbamoylphenyl)-methyl]-5H,6H,7H,8H,9H,10H-cyclohepta[b]-indole-4-carboxylic acid | 400 MHz-DMSO d6: 12.85 (br s, 1H), 7.86 (s, 1H), 7.68 (d, J = 7.6 Hz, 1H), 7.54 (dd, J = 8.0, 1.6 Hz, 1H), 7.47 (s, 1H), 7.37 (d, J = 7.6 Hz, 1H), 7.24-7.05 (m, 2H), 7.05(t, J = 7.6 Hz, 1H), 6.79 (d, J = 7.6 Hz, 2H), 5.94-5.88( m, 3H), 2.90 (dd, J = 16, 7.2 Hz, 1H), 2.74-2.66(m, 2H), 2.42-2.33 (m, 1H), 1.93-1.85 (m, 2H), 1.56-1.48 (m, 2H), 1.42-1.35 (m, 1H), 1.15-0.95(m, 6H), 0.74 (t, J = 6.8 Hz, 3H) | 418.23 | 419.1 | Compound was synthesized by method A using 3-butyl-1-cycloheptanone and 2-amide-1-benzyl bromide as appropriate building blocks |
| 7-butyl-5-[(4-methylphenyl)methyl]-5H,6H,7H,8H,9H,10H-cyclohepta[b]-indole-4-carboxylic acid | 400 MHz-DMSO d6: 12.85(br s, 1H), 7.65(d, J = 7.2 Hz, 1H), 7.36 (d, J = 6.8 Hz, 1H), 7.04-6.99 (m, 3H), 6.64 (d, J = 7.6 Hz, 2H), 5.70( d, J = 17.6 Hz, 1H), 5.53 (d, J = 17.6 Hz, 1H), 2.91-2.84 (m, 2H), 2.71-2.65 (m, 1H), 2.47 (m, 1H), 2.20(s, 3H), 1.93-1.84 (m, 2H), 1.58-1.42(m, 3H), 1.15-1.02(m, 6H), 0.77 (t, J = 6.8 Hz, 3H) | 389.24 | 390.1 | Compound was synthesized by method A using 3-butyl-1-cycloheptanone and 4-methyl-1-benzyl bromide as appropriate building blocks |
| 7-butyl-5-[(2-cyanophenyl)methyl]-5H,6H,7H,8H, | 400 MHz-DMSO d6: 12.85(br s, 1H), 7.85(d, J = 8 Hz, 1H), 7.71 (d, J = 8 Hz, 1H), 7.49-7.37 (m, 3H), 7.05 (t, J = 7.6 Hz, 1H), 6.96 (d, J+ 32 7.6 Hz, 1H), | 400.22 | 401.2 | Compound was synthesized by method A using 3-butyl-1- |

TABLE 1-continued

| IUPAC Name | 1H NMR | Exact Mass (g) | Observed [M + H]/Z | Synthetic Method |
|---|---|---|---|---|
| 9H,10H-cyclohepta[b]-indole-4-carboxylic acid | 6.18 (d, J = 17.6 Hz, 1H), 6.01 (d, J = 10.8 Hz, 1H), 5.79( d, J = 17.6 Hz, 1H), 2.92 (dd, J = 14.8, 6 Hz, 1H), 2.78-2.69 (m, 2H), 2.47 (m, 1H), 1.97-1.86 (m, 2H), 1.58-1.42(m, 2H), 1.20-0.94(m, 6H), 0.74 (t, J = 6.8 Hz, 3H) | | | cycloheptanone and 2-cyano-1-benzyl bromide as appropriate building blocks |
| 7-butyl-5-[(2-methylphenyl)methyl]-5H,6H,7H,8H,9H,10H-cyclohepta[b]-indole-4-carboxylic acid | 400 MHz-DMSO d6: 12.85(br s, 1H), 7.68(d, J = 7.2 Hz, 1H), 7.35 (d, J = 26.8 Hz, 1H), 7.14(d, J = 8 Hz, 1H), 7.04 (t, J = 8 Hz, 2H), 6.88 (d, J = 7.2 Hz, 1H), 5.76-5.72(m, 2H), 5.55( d, J = 9.6 Hz, 1H), 2.91 (dd, J = 14.8, 6 Hz, 1H), 2.78-2.69 (m, 2H), 2.47 (m, 1H), 2.34 )(s, 3H), 1.93-1.86 (m, 2H), 1.62-1.43(m, 2H), 1.16-0.94(m, 6H), 0.73 (t, J = 6.8 Hz, 3H) | 389.24 | 390.1 | Compound was synthesized by method A using 3-butyl-1-cycloheptanone and 2-methyl-1-benzyl bromide as appropriate building blocks |
| 7-butyl-5-[(2-fluorophenyl)-methyl]-5H,6H,7H,8H,9H,10H-cyclohepta[b]-indole-4-carboxylic acid | 400 MHz-DMSO d6: 12.85(br s, 1H), 7.68 (d, J = 7.6 Hz, 1H), 7.40 (d, J = 6.8 Hz, 1H), 7.26-7.14 (m, 2H), 7.05(t, J = 8.0 Hz, 1H), 6.96(t, J = 8.0 Hxz, 1H), 6.15 (t, J = 7.2 Hz, 1H), 5.82 ( d, J = 18.4 Hz, 1H), 5.64 (d, J = 18.4 Hz, 1H), 2.91 (dd, J = 16.0, 6.8 Hz, 1H), 2.81(d, J = 16.0 Hz, 1H), 2.73-2.67(m, 1H), 2.47 (m, 1H), 2.20(s, 3H), 1.93-1.87 (m, 2H), 1.58-1.42(m, 3H), 1.18-1.02(m, 6H), 0.75 (t, J = 6.8 Hz, 3H) | 393.21 | 394 | Compound was synthesized by method A using 3-butyl-1-cycloheptanone and 2-fluoro-1-benzyl bromide as appropriate building blocks |
| 5-[(3-carbamoylphenyl)-methyl]-7-pentyl-5H,6H,7H,8H,9H,10H-cyclohepta[b]-indole-4-carboxylic acid | 400 MHz-DMSO d6: 12.80(br s, 1H), 7.86 (br s, 1H), 7.67 (d, J = 8 Hz, 2H), 7.52 ( s, 1H), 7.38 (d, J = 7.2 Hz, 1H), 7.28 (br s, 1H), 7.26 ( t, J = 8 Hz, 1H), 7.05 ( t, J = 8 Hz, 1H), 6.71(d, J = 8 Hz, 1H), 5.80 ( d, J = 17 Hz, 1H), 5.64( d, J = 17 Hz, 1H) 2.93-2.88 (m, 1H), 2.82(d, J = 16 Hz, 1H), 2.72-2.66(m, 1H), 2.46 (m, 1H), 1.92-1.85 (m, 2H), 1.56-1.41(m, 3H), 1.11-0.95(m, 8H), 0.78 (t, J = 7 Hz, 3H) | 432.24 | 433.1 | Compound was synthesized by method A using 3-pentyl-1-cycloheptanone and 3-cyano-1-benzyl bromide as appropriate building blocks |
| 5-[(3-cyanophenyl)-methyl]-7-pentyl-5H,6H,7H,8H,9H,10H-cyclohepta[b]-indole-4-carboxylic acid | 400 MHz-DMSO d6: 12.83(br s, 1H), 7.67 (d, J = 8 Hz, 1H), 7.50 ( d, J = 8 Hz, 1H), 7.43(t, J = 8 Hz, 1H), 7.40 (dd, J = 7.2, 1.2 Hz, 1H), 7.26 (br s, 1H), 7.05 ( t, J = 8 Hz, 1H), 6.80 (d, J = 8 Hz, 1H), 5.77 (d, J = 18 Hz, 1H), 5.58( d, J = 18 Hz, 1H), 2.80 (dd, J = 12.0, 8.0 Hz, 1H), 2.77( d, J = 15.6 Hz, 1H), 2.72-2.67(m, 1H), 2.48 (m, 1H), 1.91-1.84 (m, 2H), 1.53-1.46(m, 2H), 1.40-1.30 (m, 1H), 1.16-0.94(m, 8H), 0.77 (t, J = 8 Hz, 3H) | 414.23 | 415.1 | Compound was synthesized by method A using 3-propyl-1-cycloheptanone and 3-cyano-1-benzyl bromide as appropriate building blocks |
| 5-[(3-carbamoylphenyl)-methyl]-7-(2-phenylethyl)-5H,6H,7H,8H,9H,10H-cyclohepta[b]-indole-4-carboxylic acid | 400 MHz-DMSO d6: 12.80(br s, 1H), 7.89 (br s, 1H), 7.66 (d, J = 8 Hz, 2H), 7.56 ( s, 1H), 7.37 (d, J = 7.2 Hz, 1H), 7.30 (br s, 1H), 7.27-7.19 ( m, 3H), 7.12 ( t, J = 8 Hz, 1H), 7.06-7.02(m, 3H), 6.74(d, J = 8 Hz, 1H), 5.82 ( d, J = 17 Hz, 1H), 5.64( d, J = 17 Hz, 1H), 2.94-2.86 (m, 2H), 2.74-2.68(m, 1H), 2.58-2.54(m, 1H) 2.45-2.33 (m, 2H), 2.00-1.96 (m, 1H), 1.90-1.85 (m, 1H), 1.60-1.41(m, 5H) | 466.23 | 467.1 | Compound was synthesized by method A using 3-(phenethyl)-1-cycloheptanone and 3-cyano-1-benzyl bromide as appropriate building blocks |
| 5-[(3-cyanophenyl)-methyl[-7-(2-phenylethyl)-5H,6H,7H,8H,9H,10H-cyclohepta[b]-indole-4-carboxylic acid | 400 MHz-DMSO d6: 12.83(br s, 1H), 7.67 (t, J = 8 Hz, 2H), 7.44-7.38 (m, 2H), 7.24 (br s, 1H), 7.22 ( t, J = 7.2 Hz, 2H), 7.13 ( t, J = 7.2 Hz, 2H), 7.06-7.04(m, 4H), 7.00(d, J = 8 Hz, 1H), 5.81 (d, J = 17.6 Hz, 1H), 5.66 ( d, J = 17.6 Hz, 1H), 2.88 (d, J = 15.6 Hz, 2H), 2.75-2.67(m, 1H), 2.62-2.55(m, 1H), 2.44-2.33 (m, 2H), 2.01-1.97 (m, 1H), 1.94-1.86 (m, 1H), 1.53-1.46(m, 2H), 1.62-1.40 (m, 5H) | 448.22 | 449.1 | Compound was synthesized by method A using 3-(phenethyl)-1-cycloheptanone and 3-cyano-1-benzyl bromide as appropriate building blocks |
| 5-[(3-carbamoylphenyl)-methyl]-7- | 400 MHz-DMSO d6: 12.80(br s, 1H), 7.86 (br s, 1H), 7.67 (d, J = 8 Hz, 2H), 7.52 ( s, 1H), 7.38 (d, J = 7.2 Hz, 1H), | 446.26 | 447.1 | Compound was synthesized by method A using 3- |

TABLE 1-continued

| IUPAC Name | 1H NMR | Exact Mass (g) | Observed [M + H]/Z | Synthetic Method |
| --- | --- | --- | --- | --- |
| hexyl-5H,6H,7H,8H,9H,10H-cyclohepta[b]-indole-4-carboxylic acid | 7.28 (br s, 1H), 7.25 ( t, J = 8 Hz, 1H), 7.04 ( t, J = 8 Hz, 1H), 6.71(d, J = 8 Hz, 1H), 5.80 ( d, J = 17 Hz, 1H), 5.60( d, J = 17 Hz, 1H) 2.93-2.88 (m, 1H), 2.82(d, J = 16 Hz, 1H), 2.72-2.66(m, 1H), 2.46 (m, 1H), 1.92-1.85 (m, 2H), 1.56-1.41(m, 3H), 1.23-0.97(m, 10H), 0.82 (t, J = 7 Hz, 3H) | | | hexyl-1-cycloheptanone and 3-cyano-1-benzyl bromide as appropriate building blocks |
| 5-[(3-cyanophenyl)-methyl]-7-hexyl-5H,6H,7H,8H,9H,10H-cyclohepta[b]-indole-4-carboxylic acid | 400 MHz-DMSO d6: 12.9(br s, 1H), 7.68 (d, J = 8 Hz, 1H), 7.66 ( d, J = 8 Hz, 1H), 7.44(t, J = 8 Hz, 1H), 7.40 (dd, J = 7.2, 1.2 Hz, 1H), 7.29 (br s, 1H), 7.06 ( t, J = 8 Hz, 1H), 6.98 (d, J = 8 Hz, 1H), 5.79( d, J = 18 Hz, 1H), 5.60( d, J = 18 Hz, 1H), 2.90 (dd, J = 12.0, 8.0 Hz, 1H), 2.78( d, J = 15.6 Hz, 1H), 2.69(m, dd, J = 12.0, 8.0 Hz, 1H), 2.48 (m, 1H), 1.92-1.85 (m, 2H), 1.55-1.50 (m, 2H), 1.40-1.30 (m, 1H), 1.23-0.95(m, 10H), 0.77 (t, J = 7.2 Hz, 3H) | 428.25 | 429.1 | Compound was synthesized by method A using 3-hexyl-1-cycloheptanone and 3-cyano-1-benzyl bromide as appropriate building blocks |
| 5-[(3-carbamoylphenyl)-methyl]-7-octyl-5H,6H,7H,8H,9H,10H-cyclohepta[b]-indole-4-carboxylic acid | 400 MHz-DMSO d6: 12.9(br s, 1H), 7.92(s, 1H), 7.74(s, 1H), 7.69 (d, J = 6.8 Hz, 1H), 7.59 ( d, J = 7.2 Hz, 1H), 7.52(dd, J = 6.0, 1.2 Hz, 1H), 7.27-7.23 (m, 1H), 7.29 (br s, 1H), 7.09 ( t, J = 7.6 Hz, 1H), 6.71 (d, J = 8.0 Hz, 1H), 6.46(s, 1H), 5.67 (d, J = 18 Hz, 1H), 5.59( d, J = 18 Hz, 1H), 2.98-2.92 (m, 2H), 2.84-2.80 (m, 1H), 2.67( dd, J = 15.6, 10 Hz, 1H), 2.48 (m, 1H), 2.07-1.96 (m, 3H), 1.87-1.60 (m, 5H), 1.40- 1.23(m, 20H), 0.87 (t, J = 7.2 Hz, 3H) | 474.29 | 475.1 | Compound was synthesized by method A using 3-octyll-1-cycloheptanone and 3-cyano-1-benzyl bromide as appropriate building blocks |
| 5-[(3-cyanophenyl)-methyl]-7-octyl-5H,6H,7H,8H,9H,10H-cyclohepta[b]-indole-4-carboxylic acid | 400 MHz-DMSO d6: 12.9(br s, 1H), 7.74 (t, J = 8 Hz, 2H), 7.47( d, J = 8.0 Hz, 1H), 7.32(t, J = 8.0 Hz, 1H), 7.15-7.00 (m, 3H), 5.75( d, J = 18 Hz, 1H), 5.57(d, J = 18 Hz, 1H), 2.98-2.92 (m, 1H), 2.78-2.72 (m, 2H), 2.50-2.44( m, 1H), 2.48 (m, 1H), 2.01-1.93 (m, 3H), 1.87-1.60 (m, 4H), 1.40- 1.23(m, 17H), 0.87 (t, J = 7.2 Hz, 3H) | 456.28 | 457.1 | Compound was synthesized by method A using 3-octyll-1-cycloheptanone and 3-cyano-1-benzyl bromide as appropriate building blocks |
| 5-[(3-fluorophenyl)-methyl]-7-hexyl-5H,6H,7H,8H,9H,10H-cyclohepta[b]-indole-4-carboxylic acid | 400 MHz-DMSO d6: 12.90 (br s, 1H), 7.65 (d, J = 6 Hz, 1H), 7.37 (d, J = 6 Hz, 1H), 7.25 (dd, J = 14.4, 8 Hz, 1H), 7.06-6.96 (m, 2H), 6.57-6.64 (m, 2H), 5.81 (d, J = 18 Hz, 1H), 5.60( d, J = 18 Hz, 1H) 2.93-2.80 (m, 2H), 2.71-2.66( m, 1H), 2.62-2.46(m, 1H), 1.92-1.85 (m, 2H), 1.56-1.41(m, 2H), 1.45-1.35(m, 1H), 1.23-0.97(m, 10H), 0.83 (t, J = 6.8 Hz, 3H) | 421.24 | 422.1 | Compound was synthesized by method A using 3-hexyl-1-cycloheptanone and 3-fluoro-1-benzyl bromide as appropriate building blocks |
| 7-hexyl-5-[(pyridin-3-yl)methyl]-5H,6H,7H,8H,9H,10H-cyclohepta[b]-indole-4-carboxylic acid | 400 MHz-DMSO d6: 12.6 (br s, 1H), 8.37(d, J = 3.2 Hz, 1H), 8.06(d, J = 1.6 Hz, 1H), 7.68(dd, J = 8.0, 1.2 Hz, 1H), 7.40 (dd, J = 7.2, 0.8 Hz, 1H), 7.25-7.22 (m, 1H), 7.06-7.01 (m, 2H), 5.76 ( d, J = 17.6 Hz, 1H), 5.61( d, J = 17.6 Hz, 1H) 2.93-2.84 (m, 2H), 2.72-2.66( m, 1H), 2.56-2.52(m, 1H), 1.93-1.85 (m, 2H), 1.56-1.43(m, 3H), 1.23-1.10(m, 10H), 0.83 (t, J = 7.2 Hz, 3H) | 404.25 | 405.1 | Compound was synthesized by method A using 3-hexyl-1-cycloheptanone and pyridyl-3-benzyl bromide as appropriate building blocks |
| 7-hexyl-5-[(3-methylphenyl)methyl]-5H,6H,7H,8H,9H,10H-cyclohepta[b]-indole-4-carboxylic acid | 400 MHz-DMSO d6: 12.82 (br s, 1H), 7.66 (d, J = 6.8 Hz, 1H), 7.37 (d, J = 6.8 Hz, 1H), 7.06-7.01 (m, 2H), 6.96 (d, J = 7.6 Hz, 1H), 6.70 (s, 1H), 6.43 (d, J = 6 Hz, 1H), 5.72 ( d, J = 17.6 Hz, 1H), 5.52( d, J = 17.6 Hz, 1H) 2.93-2.80 (m, 2H), 2.71-2.66( m, 1H), 2.62-2.46(m, 1H), 2.22(s, 3H), 1.96-1.82 (m, 2H), 1.56-1.45(m, 2H), 1.43-1.35(m, 1H), 1.23-0.97(m, 10H), 0.83 (t, J = 7.2 Hz, 3H) | 417.27 | 416.5 | Compound was synthesized by method A using 3-hexyl-1-cycloheptanone and 3-methyl-1-benzyl bromide as appropriate building blocks |
| 7-hexyl-5-[(3-methoxyphenyl)-methyl]- | 400 MHz-DMSO d6: 12.90 (br s, 1H), 7.66 (d, J = 7.2 Hz, 1H), 7.38 (d, J = 7.2 Hz, 1H), 7.11 (t, J = 7.6 Hz, 1H), | 433.26 | 434.1 | Compound was synthesized by method A using 3- |

TABLE 1-continued

| IUPAC Name | 1H NMR | Exact Mass (g) | Observed [M + H]/Z | Synthetic Method |
|---|---|---|---|---|
| 5H,6H,7H,8H, 9H,10H-cyclohepta[b]-indole-4-carboxylic acid | 7.04(t, J = 7.6 Hz, 1H), 6.71 (d, J = 6.8 Hz, 1H), 6.31 (s, 1H), 6.27 (d, J = 6.8 Hz, 1H), 5.74( d, J = 17.6 Hz, 1H), 5.54 (d, J = 17.6 Hz, 1H), 3.62(s, 3H), 2.91-2.82 (m, 2H), 2.71-2.66(m, 1H), 2.62-2.46(m, 1H), 1.96-1.82 (m, 2H), 1.56-1.45(m, 2H), 1.43-1.35(m, 1H), 1.23-0.97(m, 10H), 0.83 (t, J = 7.2 Hz, 3H) | | | hexyl-1-cycloheptanone and 3-methoxy-1-benzyl bromide as appropriate building blocks |
| 5-[(3-chlorophenyl) methyl]-7-hexyl-5H,6H,7H,8H, 9H,10H-cyclohepta[b]-indole-4-carboxylic acid | 400 MHz-DMSO d6: 12.90 (br s, 1H), 7.65(d, J = 7.6 Hz, 1H), 7.38 (d, J = 7.6 Hz, 1H), 7.27-7.20(m, 2H), 7.04(t, J = 7.2 Hz, 1H), 6.84 (s, 1H), 6.67 (d, J = 7.2 Hz, 1H), 5.74 (d, J = 17.6 Hz, 1H), 5.54 (d, J = 17.6 Hz, 1H), 2.88 (dd, J = 15.6, 7.2 Hz, 1H), 2.81(d, J = 15.6, 1H), 2.71-2.66(m, 1H), 2.62-2.46(m, 1H), 1.96-1.82 (m, 2H), 1.56-1.45(m, 2H), 1.43-1.35(m, 1H), 1.23-0.97(m, 10H), 0.83 (t, J = 7.2 Hz, 3H) | 437.21 | 438.1 | Compound was synthesized by method A using 3-hexyl-1-cycloheptanone and 3-chloro-1-benzyl bromide as appropriate building blocks |
| 7-hexyl-5-[(2-methoxypyridin-4-yl)methyl]-5H,6H,7H,8H, 9H,10H-cyclohepta[b]-indole-4-carboxylic acid | 500 MHz-DMSO d6: 12.8 (br s, 1H), 8.00 (d, J = 5.0 Hz, 1H), 7.70 (d, J = 8.0 Hz, 1H), 7.41 (d, J = 7.5 Hz, 1H), 7.07 (t, J = 7.5 Hz, 1H), 6.41 (d, J = 5.0 Hz, 1H), 6.00 (s, 1H), 5.76 (d, J = 17.5 Hz, 1H), 5.56 (d, J = 17.5 Hz, 1H), 3.74(s, 3H), 2.91-2.88 (m, 1H), 2.79-2.72 (m, 2H), 2.71-2.64(m, 1H), 1.93-1.85 (m, 2H), 1.56-1.43(m, 3H), 1.24-1.08(m, 12H), 0.82 (t, J = 7.2 Hz, 3H) | 434.26 | 433.35 | Compound was synthesized by method A using 3-hexyl-1-cycloheptanone and pyridyl-2-methoxy-3-benzyl bromide as appropriate building blocks |
| 5-[(3-carboxyphenyl) methyl]-7-hexyl-5H,6H,7H,8H, 9H,10H-cyclohepta[b]-indole-4-carboxylic acid | 500 MHz-DMSO d6: 12.8 (br s, 1H), 7.74 (d, J = 7.5 Hz, 1H), 7.68 (d, J = 7.5 Hz, 1H), 7.46(s, 1H), 7.39 (d, J = 9.0 Hz, 1H), 7.35 (t, J = 7.5 Hz, 1H), 7.05 (t, J = 7.5 Hz, 1H), 6.96 (d, J = 7.0 Hz, 1H), 6.00 (s, 1H), 5.81 (d, J = 17.5 Hz, 1H), 5.61 (d, J = 17.5 Hz, 1H), 3.74(s, 3H), 2.91-2.89 (m, 1H), 2.81 (d, J = 15 Hz, 1H), 2.71-2.64(m, 1H), 1.92-1.87 (m, 2H), 1.56-1.43(m, 3H), 1.24-1.08(m, 12H), 0.82 (t, J = 7.2 Hz, 3H) | 447.24 | 446.48 | Compound was synthesized by method A using 3-hexyl-1-cycloheptanone and 3-carboxyl-1-benzyl bromide as appropriate building blocks |
| 5-[(4-carbamoylphenyl)-methyl]-7-hexyl-5H,6H,7H,8H, 9H,10H-cyclohepta[b]-indole-4-carboxylic acid | 400 MHz-DMSO d6: 12.8 (br s, 1H), 7.83(s, 1H), 7.71 (d, J = 7.6 Hz, 2H), 7.67 (d, J = 7.6 Hz, 2H), 7.39 (d, J = 7.5 Hz, 1H), 7.26 (s, 1H), 7.04 (t, J = 8.0 Hz, 1H), 6.79(d, J = 8.0 Hz, 2H), 6.00 (s, 1H), 5.81 (d, J = 17.6 Hz, 1H), 5.63 (d, J = 17.6 Hz, 1H), 2.93-2.81 (m, 2H), 2.72-2.67(m, 1H), 2.60-2.50(m, 2H), 1.93-1.85 (m, 2H), 1.56-1.43(m, 3H), 1.24-1.06(m, 10H), 0.81 (t, J = 7.2 Hz, 3H) | 446.26 | 447.1 | Compound was synthesized by method A using 3-hexyl-1-cycloheptanone and 1-carboxylamide-3-benzyl bromide as appropriate building blocks |
| 5-[(2-carbamoylphenyl)-methyl]-7-hexyl-5H,6H,7H,8H, 9H,10H-cyclohepta[b]-indole-4-carboxylic acid | 400 MHz-DMSO d6: 12.8 (br s, 1H), 7.85(s, 1H), 7.69 (d, J = 7.2 Hz, 1H), 7.54 (d, J = 6.4 Hz, 2H), 7.47 (s, 1H), 7.38 (d, J = 6.4 Hz, 2H), 7.23-7.14 (m, 2H), 7.05 (t, J = 8.0 Hz, 2H), 5.92-5.88(m, 3H), 2.93-2.88 (m, 1H), 2.74-2.65 (m, 2H), 2.45-2.33(m, 1H), 1.93-1.85 (m, 2H), 1.56-1.43(m, 2H), 1.43-1.40(m, 1H), 1.24-1.06(m, 10H), 0.82 (t, J = 7.2 Hz, 3H) | 446.26 | 447.1 | Compound was synthesized by method A using 3-hexyl-1-cycloheptanone and 1-carboxylamide-2-benzyl bromide as appropriate building blocks |
| 7-hexyl-5-[(4-methylphenyl) methyl]-5H,6H,7H,8H, 9H,10H-cyclohepta[b]-indole-4-carboxylic acid (m, 1H), | 400 MHz-DMSO d6: 12.82 (br s, 1H), 7.65(d, J = 7.6 Hz, 1H), 7.36 (d, J = 7.6 Hz, 1H), 7.05-6.99(m, 3H), 6.63 (d, J = 8 Hz, 1H), 5.70 (d, J = 17.6 Hz, 1H), 5.52 (d, J = 17.6 Hz, 1H), 2.92-2.83 (m 2H), 2.71-2.65 (m, 1H), 2.52-2.46(m, 1H), 2.20 (s, 3H), 1.96-1.82 (m, 2H), 1.56-1.45(m, 2H), 1.43-1.35 1.23-0.98(m, 10H), 0.83 (t, J = 7.2 Hz, 3H) | 417.27 | 416.57 [M − H]− | Compound was synthesized by method A using 3-hexyl-1-cycloheptanone and 4-methyl-1-benzyl bromide as appropriate building blocks |
| 5-[(4-cyanophenyl)-methyl]-7-hexyl-5H,6H,7H,8H, | 400 MHz-DMSO d6: 12.82 (br s, 1H), 7.70 (m, 3H), 7.41 (d, J = 7.6 Hz, 1H), 7.06(t, J = 7.2 Hz, 1H), 6.93 (d, J = 8.4 Hz, 2H), 5.85 (d, J = 17.6 Hz, 1H), 5.65 (d, | 428.25 | 429.24 | Compound was synthesized by method A using 3-hexyl-1- |

TABLE 1-continued

| IUPAC Name | 1H NMR | Exact Mass (g) | Observed [M + H]/Z | Synthetic Method |
|---|---|---|---|---|
| 9H,10H-cyclohepta[b]-indole-4-carboxylic acid | J = 17.6 Hz, 1H), 2.93-2.86 (m, 1H), 2.76-2.65 (m, 2H), 2.48-2.44(m, 1H), 1.94-1.84 (m, 2H), 1.56-1.45(m, 2H), 1.43-1.35 (m, 1H), 1.23-0.98(m, 10H), 0.85 (t, J = 7.2 Hz, 3H) | | | cycloheptanone and 4-cyano-1-benzyl bromide as appropriate building blocks |
| 5-[(2-cyanophenyl)-methyl]-7-hexyl-5H,6H,7H,8H,9H,10H-cyclohepta[b]-indole-4-carboxylic acid | 400 MHz-DMSO d6: 12.8 (br s, 1H), 7.85 (d, J = 6.4 Hz, 1H), 7.71 (d, J = 7.2 Hz, 1H), 7.48-7.38 (m, 3H), 7.07 (t, J = 8.0 Hz, 1H), 6.17 (d, J = 8.0 Hz, 1H), 6.00 (d, J = 17.5 Hz, 1H), 5.80 (d, J = 17.5 Hz, 1H), 2.96-2.89 (m, 1H), 2.77-2.65 (m, 2H), 2.55-2.49 (m, 1H) 1.92-1.87 (m, 2H), 1.58-1.43(m, 3H), 1.24-1.08(m, 10H), 0.82 (t, J = 7.2 Hz, 3H) | 428.25 | 429.17 | Compound was synthesized by method A using 3-hexyl-1-cycloheptanone and 1-cyano-2-benzyl bromide as appropriate building blocks |
| 7-hexyl-5-[(2-methylphenyl) methyl]-5H,6H,7H,8H,9H,10H-cyclohepta[b]-indole-4-carboxylic acid | 400 MHz-DMSO d6: 12.8 (br s, 1H), 7.68(d, J = 7.2 Hz, 1H), 7.35 (d, J = 7.2 Hz, 1H), 7.14 (d, J = 7.6 Hz, 1H), 7.04 (t, J = 8 Hz, 1H), 6.88 (t, J = 8 Hz, 1H), 5.77-5.73 (m, 2H), 5.54 (d, J = 18.4 Hz, 1H), 2.93 (dd, J = 14.8 Hz, 6 Hz, 1H), 2.77-2.67 (m, 2H), 2.50-2.44(m, 1H), 2.34 (s, 3H), 1.94-1.82 (m, 2H), 1.59-1.43(m, 3H), 1.26-0.98(m, 10H), 0.82 (t, J = 7.2 Hz, 3H) | 417.27 | 418.1 | Compound was synthesized by method A using 3-hexyl-1-cycloheptanone and 2-methyl-1-benzyl bromide as appropriate building blocks |
| 5-[(2-fluorophenyl)-methyl]-7-hexyl-5H,6H,7H,8H,9H,10H-cyclohepta[b]-indole-4-carboxylic acid | 400 MHz-DMSO d6: 12.8 (br s, 1H), 7.69(d, J = 7.2 Hz, 1H), 7.41 (d, J = 7.2 Hz, 1H), 7.23-7.14 (m, 2H), 7.06 (t, J = 8 Hz, 1H), 6.96 (t, J = 8 Hz, 1H), 6.14 (t, J = 8 Hz, 1H), 5.81 (d, J = 18.0 Hz, 1H), 5.64 (d, J = 18.0 Hz, 1H), 2.91 (dd, J = 14.8 Hz, 6 Hz, 1H), 2.81 (d, J = 16.0 Hz, 1H), 2.72-2.67(m, 1H), 2.50-2.44(m, 1H), 1.94-1.86 (m, 2H), 1.57-1.43(m, 3H), 1.23-1.02(m, 10H), 0.82 (t, J = 7.2 Hz, 3H) | 421.24 | 422.29 | Compound was synthesized by method A using 3-hexyl-1-cycloheptanone and 2-Flouro-1-benzyl bromide as appropriate building blocks |
| 5-[(4-fluorophenyl)-methyl]-7-hexyl-5H,6H,7H,8H,9H,10H-cyclohepta[b]-indole-4-carboxylic acid | 400 MHz-DMSO d6: 12.8 (br s, 1H), 7.68(d, J = 7.2 Hz, 1H), 7.35 (d, J = 7.2 Hz, 1H), 7.14 (d, J = 7.6 Hz, 1H), 7.04 (t, J = 8 Hz, 1H), 6.88 (t, J = 8 Hz, 1H), 5.77-5.73 (m, 2H), 5.54 (d, J = 18.4 Hz, 1H), 2.93-2.81 (m, 2H), 2.71-2.65 (m, 1H), 2.50-2.44(m, 1H), 2.34 (s, 3H), 1.94-1.82 (m, 2H), 1.59-1.43(m, 3H), 1.24-0.96(m, 10H), 0.83 (t, J = 7.2 Hz, 3H) | 421.24 | 420.46 | Compound was synthesized by method A using 3-hexyl-1-cycloheptanone and 4-fluoro- 1-benzyl bromide as appropriate building blocks |
| 9-[(3-carbamoylphenyl)-methyl]-2-hexyl-2,3,4,9-tetrahydro-1H-carbazole-8-carboxylic acid | 400 MHz-DMSO d6: 12.80(br s, 1H), 7.87 (br s, 1H), 7.65 (d, J = 8 Hz, 1H), 7.51 (d, J = 8 Hz, 1H), 7.49 ( s, 1H), 7.39 (d, J = 7.2 Hz, 1H), 7.30 (br s, 1H), 7.24 ( t, J = 8 Hz, 1H), 7.04 ( t, J = 8 Hz, 1H), 6.64 (d, J = 8 Hz, 1H), 5.68 ( d, J = 17 Hz, 1H), 5.62( d, J = 17 Hz, 1H) 2.84-2.77 (m, 2H), 2.67-2.63 (m, 1H), 2.27-2.21 (m, 1H), 1.98-1.94 (m, 1H), 1.83 (br s, 1H), 1.46-1.24(m, 11H), 0.85 (t, J = 7 Hz, 3H) | 432.24 | 433.1 | Compound was synthesized by method A using 3-hexyl-1-cyclohexanone and 3-cyano-1-benzyl bromide as appropriate building blocks |
| 9-[(3-cyanophenyl)-methyl]-2-hexyl-2,3,4,9-tetrahydro-1H-carbazole-8-carboxylic acid | 400 MHz-DMSO d6: 12.81(br s, 1H), 7.64 (t, J = 8 Hz, 2H), 7.42 (t, J = 8 Hz, 2H), 7.23 (br s, 1H), 7.06 ( t, J = 8 Hz, 1H), 6.93 (d, J = 8 Hz, 1H), 5.68( d, J = 18 Hz, 1H), 5.60 (d, J = 18 Hz, 1H), 2.83-2.77 (m, 2H), 2.66-2.60 (m, 1H), 2.23 ( dd, J = 16.8, 8.8 Hz, 1H), 1.98-1.90 (m, 1H), 1.90-1.80 (m, 1H), 1.48-1.25(m, 11H), 0.85 (t, J = 6.4 Hz, 3H) | 414.23 | 415.1 | Compound was synthesized by method A using 3-hexyl-1-cyclohexanone and 3-cyano-1-benzyl bromide as appropriate building blocks |
| 9-[(3-carboxyphenyl) methyl]-2-hexyl-2,3,4,9-tetrahydro-1H-carbazole-8-carboxylic acid | 400 MHz-DMSO d6: 12.80(br s, 1H), 8.30 (br s, 1H), 7.70 (d, J = 7.6 Hz, 1H), 7.52-7.49 (m, 2H), 7.31 (d, J = 7.2 Hz, 1H), 7.27 ( t, J = 8 Hz, 1H), 6.98 ( t, J = 8 Hz, 1H), 6.86 (d, J = 7.2 Hz, 1H), 5.76 ( d, J = 17.2 Hz, 1H), 5.66( d, J = 17.2 Hz, 1H) 2.81-2.74 (m, 2H), 2.67-2.63 (m, 1H), 2.23-2.17 (m, 1H), 1.98-1.93 (m, 1H), 1.81 (br s, 1H), 1.46-1.23(m, 11H), 0.84 (t, J = 6.4 Hz, 3H) | 433.23 | 434.1 | Compound was synthesized by method A using 3-hexyl-1-cyclohexanone and 3-cyano-1-benzyl bromide as appropriate building blocks |

TABLE 1-continued

| IUPAC Name | 1H NMR | Exact Mass (g) | Observed [M + H]/Z | Synthetic Method |
|---|---|---|---|---|
| 9-[(3-fluorophenyl)-methyl]-2-hexyl-2,3,4,9-tetrahydro-1H-carbazole-8-carboxylic acid | 1H-NMR (400 MHz-DMSO d6): 12.80(br s, 1H), 7.62 (d, J = 7.6 Hz, 1H), 7.41 (d, J = 7.6 Hz, 1H), 7.25-7.22 (m, 1H), 7.27-6.96 ( m, 2H), 6.52-6.49(m, 2H), 5.65 ( d, J = 17.2 Hz, 1H), 5.58 ( d, J = 17.2 Hz, 1H) 2.84-2.76 (m, 2H), 2.67-2.60 (m, 1H), 2.27-2.21 (m, 1H), 1.98-1.95 (m, 1H), 1.84 (br s, 1H), 1.46-1.23(m, 11H), 0.85 (t, J = 6.4 Hz, 3H) | 407.23 | 408.1 | Compound was synthesized by method A using 3-hexyl-1-cyclohexanone and 3-fluoro-1-benzyl bromide as appropriate building blocks |
| 2-hexyl-9-[(pyridin-3-yl)methyl]-2,3,4,9-tetrahydro-1H-carbazole-8-carboxylic acid | 1H-NMR (400 MHz-DMSO d6) : 8.35-8.33 (m, 1H), 8.12(s, 1H), 7.62 (d, J = 7.6 Hz, 1H), 7.41 (d, J = 7.6 Hz, 1H), 7.25-7.22 (m, 1H), 7.27-6.96 ( m, 2H), 6.52-6.49(m, 2H), 5.65 ( d, J = 17.2 Hz, 1H), 5.58 ( d, J = 17.2 Hz, 1H) 2.84-2.76 (m, 2H), 2.67-2.60 (m, 1H), 2.27-2.21 (m, 1H), 1.98-1.95 (m, 1H), 1.84 (br s, 1H), 1.46-1.23(m, 11H), 0.85 (t, J = 6.4 Hz, 3H) | 390.23 | 391.25 | Compound was synthesized by method A using 3-hexyl-1-cyclohexanone and pyridyl-3-benzyl bromide as appropriate building blocks |
| 2-hexyl-9-[(3-methylphenyl)methyl]-2,3,4,9-tetrahydro-1H-carbazole-8-carboxylic acid | 1H-NMR (400 MHz-DMSO d6): 12.80(br s, 1H), 7.60 (d, J = 6.8 Hz, 1H), 7.40 (d, J = 6.8 Hz, 1H), 7.07-7.00 (m, 2H), 6.96-6.95 (m, 1H), 6.70(s, 1H), 6.38(d, J = 6.8 Hz, 1H), 5.59 ( d, J = 17.2 Hz, 1H), 5.52 ( d, J = 17.2 Hz, 1H) 2.86-2.76 (m, 2H), 2.67-2.63 (m, 1H), 2.29-2.22 (m, 1H), 2.18(s, 3H), 1.98-1.95 (m, 1H), 1.83 (br s, 1H), 1.46-1.25(m, 11H), 0.85 (t, J = 6.4 Hz, 3H) | 403.25 | 404.1 | Compound was synthesized by method A using 3-hexyl-1-cyclohexanone and 3-methyl-1-benzyl bromide as appropriate building blocks |
| 2-hexyl-9-[(3-methoxyphenyl)-methyl]-2,3,4,9-tetrahydro-1H-carbazole-8-carboxylic acid | 1H-NMR (400 MHz-DMSO d6): 12.80(br s, 1H), 7.62 (dd, J = 7.6, 0.8 Hz, 1H), 7.41 (dd, J = 7.6, 0.8 Hz, 1H), 7.10(t, J = 6.0 Hz, 1H), 7.03(t, J = 6.0 Hz, 1H), 6.72-6.70(m, 2H), 6.26(s, 1H), 6.25( d, J = 7, 6 Hz, 1h), 5.60 ( d, J = 17.2 Hz, 1H), 5.54 ( d, J = 17.2 Hz, 1H), 3.62(s, 3H), 2.85-2.76 (m, 2H), 2.64-2.60 (m, 1H), 2.28-2.22 (m, 1H), 1.98-1.95 (m, 1H), 1.83 (br s, 1H), 1.45-1.25(m, 11H), 0.87 (t, J = 6.4 Hz, 3H) | 419.25 | 420.1 | Compound was synthesized by method A using 3-hexyl-1-cyclohexanone and 3-methoxy-1-benzyl bromide as appropriate building blocks |
| 9-[(3-chlorophenyl)methyl]-2-hexyl-2,3,4,9-tetrahydro-1H-carbazole-8-carboxylic acid | 1H-NMR (400 MHz, DMSO-d6): 12.90 (s, 1H), 7.72-7.69 (m, 2H), 7.14-7.065 (m, 3H), 6.86 (s, 1H), 6.57 (d, J = 7.20 Hz, 1H), 5.63 (d, J = 17.2 Hz, 1H), 2.87-2.84 (m, 1H), 2.78-2.71 (m, 2H), 2.28-2.21 (m, 1H), 2.06-2.01 (m, 1H), 1.89 (br s, 1H), 1.58-1.26 (m, 1H), 1.08-1.13 (m, 11H), 0.88 (t, J = 7.20 Hz, 3H). | 423.20 | 424.1 | Compound was synthesized by method A using 3-hexyl-1-cyclohexanone and 3-chloro-1-benzyl bromide as appropriate building blocks |
| 2-hexyl-9-[(3-hydroxyphenyl)-methyl]-2,3,4,9-tetrahydro-1H-carbazole-8-carboxylic acid | | 405.23 | | Compound was synthesized by method A using 3-hexyl-1-cyclohexanone and 3-hydroxy-1-benzyl bromide as appropriate building blocks |
| 2-hexyl-9-[(2-methoxypyridin-4-yl)methyl]-2,3,4,9-tetrahydro-1H-carbazole-8-carboxylic acid | 400 MHz-DMSO d6: 12.8 (br s, 1H), 7.96(d, J = 4.8 Hz, 1H), 7.41 (d, J = 8.0 Hz, 1H), 7.27 (d, J = 8.0 Hz, 1H), 6.95 (t, J = 8 Hz, 1H), 6.44 (d, J = 4.4 Hz, 1H), 5.95 (s, 1H), 5.84 (d, J = 17.6 Hz, 1H), 5.70 (d, J = 17.6 Hz, 1H), 3.73 (s, 3H), 2.76-2.64 (m, 3H), 2.17-2.10 (m, 1H), 1.96-1.92 (m, 1H), 1.78 (br s, 1H), 1.44-1.24(m, 11H), 0.85 (t, J = 7.2 Hz, 3H) | 420.24 | 421.1 | Compound was synthesized by method A using 3-hexyl-1-cyclohexanone and 2-methoxy-4-benzyl pyridine as appropriate building blocks |
| 9-[(3-carboxyphenyl)methyl]-2-hexyl-2,3,4,9-tetrahydro-1H-carbazole- | 400 MHz-DMSO d6: 12.8 (br s, 1H), 7.73(d, J = 7.2 Hz, 1H), 7.62 (d, J = 7.2 Hz, 1H), 7.44 (s, 1H), 7.40 (d, J = 7.2 Hz, 1H), 7.33 (t, J = 8.0 Hz, 1H), 7.04 (t, J = 8 Hz, 1H), 6.88 (d, J = | 433.23 | 434 | Compound was synthesized by method A using 3-hexyl-1-cyclohexanone and |

TABLE 1-continued

| IUPAC Name | 1H NMR | Exact Mass (g) | Observed [M + H]/Z | Synthetic Method |
|---|---|---|---|---|
| carbazole-8-carboxylic acid | 7.2 Hz, 1H), 5.70 (d, J = 17.6 Hz, 1H), 5.63 (d, J = 17.6 Hz, 1H), 2.83-2.77 (m, 2H), 2.68-2.64 (m, 1H), 2.26-2.22(m, 1H), 1.98-1.95 (m, 1H), 1.90-1.85 (m, 1H), 1.49-1.33(m, 5H), 1.30-1.20(m, 6H), 0.84 (t, J = 7.2 Hz, 3H) | | | 3-carboxy-1-benzyl bromide as appropriate building blocks |
| 9-[(4-carbamoylphenyl)-methyl]-2-hexyl-2,3,4,9-tetrahydro-1H-carbazole-8-carboxylic acid | 400 MHz-DMSO d6: 12.81(br s, 1H), 7.83 (s, 1H), 7.68 (t, J = 8 Hz, 2H), 7.62 (t, J = 8 Hz, 1H), 7.42 (d, J = 6.0 Hz, 2H), 7.26 (br s, 1H), 7.04 ( t, J = 8 Hz, 1H), 6.93 (d, J = 8 Hz, 1H), 5.68( d, J = 18 Hz, 1H), 5.60 (d, J = 18 Hz, 1H), 2.84-2.78 (m, 2H), 2.67-2.62 (m, 1H), 2.23 ( dd, J = 16.0, 8.8 Hz, 1H), 1.98-1.94 (m, 1H), 1.83 (br s, 1H), 1.47-1.25(m, 11H), 0.85 (t, J = 6.4 Hz, 3H) | 432.24 | 433.1 | Compound was synthesized by method A using 3-hexyl-1-cyclohexanone and 4-carboxamide-1-benzyl bromide as appropriate building blocks |
| 9-[(2-carbamoylphenyl)-methyl]-2-hexyl-2,3,4,9-tetrahydro-1H-carbazole-8-carboxylic acid | 400 MHz-DMSO d6: 12.7(br s, 1H), 7.84 (s, 1H), 7.63(d, J = 7.2 Hz, 1H), 7.52 (d, J = 7.2 Hz, 1H), 7.46 (s, 1H), , 7.41 (d, J = 7.2 Hz, 2H), 7.20 (t, J = 7.2 Hz, 1H), 7.12 ( t, J = 6.8 Hz, 1H), 7.05 ( t, J = 6.8 Hz, 1H), 5.88-5.77 (m, 2H), 2.81-2.75 (m, 1H), 2.68-2.62 (m, 2H), 2.14-2.08 (m, 1H), 1.98-1.94 (m, 1H), 1.78 (br s, 1H), 1.50-1.22(m, 11H), 0.84 (t, J = 6.4 Hz, 3H) | 432.24 | 433.1 | Compound was synthesized by method A using 3-hexyl-1-cyclohexanone and 2-carboxylamide-1-benzyl bromide as appropriate building blocks |
| 2-hexyl-9-[(4-methylphenyl)methyl]-2,3,4,9-tetrahydro-1H-carbazole-8-carboxylic acid | 400 MHz-DMSO d6: 12.8 (br s, 1H), 7.60 (d, J = 8.0 Hz, 1H), 7.39 (d, J = 8.0 Hz, 1H), 7.04-6.98 (m, 3H), 6.60 (d, J = 8.0 Hz, 1H), 5.58 (d, J = 17.6 Hz, 1H), 5.51 (d, J = 17.6 Hz, 1H), 2.83-2.77 (m, 2H), 2.68-2.64 (m, 1H), 2.28-2.19(m, 4H), 1.98-1.95 (m, 1H), 1.81 (br s, 1H), 1.46-1.25(m, 11H), 0.85 (t, J = 7.2 Hz, 3H) | 403.25 | 404.1 | Compound was synthesized by method A using 3-hexyl-1-cyclohexanone and 4-methyl-1-benzyl bromide as appropriate building blocks |
| 9-[(4-cyanophenyl)-methyl]-2-hexyl-2,3,4,9-tetrahydro-1H-carbazole-8-carboxylic acid | 400 MHz-CDCl3: 12.8 (br s, 1H), 7.73 (dd, J = 8.0, 1.2 Hz, 1H), 7.39 (d, J = 8.0 Hz, 1H), 7.13 (t, J = 8.0 Hz, 1H), 6.86 (d, J = 8.0 Hz, 1H), 5.72 (d, J = 18.4 Hz, 1H), 5.64 (d, J = 18.4 Hz, 1H), 2.88-2.80 (m, 1H), 2.74-2.67 (m, 2H), 2.24-2.18(m, 1H), 2.06-2.03(m, 1H), 1.89 (br s, 1H), 1.46-1.25(m, 11H), 0.88 (t, J = 7.2 Hz, 3H) | 414.23 | 415.1 | Compound was synthesized by method A using 3-hexyl-1-cyclohexanone and 4-cyano-1-benzyl bromide as appropriate building blocks |
| 9-[(2-cyanophenyl)-methyl]-2-hexyl-2,3,4,9-tetrahydro-1H-carbazole-8-carboxylic acid | 400 MHz-CDCl3: 12.8 (br s, 1H), 7.74 (t, J = 7.6 Hz, 2H), 7.66-7.64 (m, 1H), 7.34-7.26(m, 2H), 7.13 (t, J = 8.0 Hz, 1H), 6.36 (d, J = 8.0 Hz, 1H), 5.88 (d, J = 17.6 Hz, 1H), 5.82 (d, J = 17.6 Hz, 1H), 2.88-2.82 (m, 1H), 2.74-2.67 (m, 2H), 2.22-2.16(m, 1H), 2.06-2.00(m, 1H), 1.89 (br s, 1H), 1.46-1.27 (m, 11H), 0.88 (t, J = 7.2 Hz, 3H) | 414.23 | 415.1 | Compound was synthesized by method A using 3-hexyl-1-cyclohexanone and 2-cyano-1-benzyl bromide as appropriate building blocks |
| 2-hexyl-9-[(2-methylphenyl)methyl]-2,3,4,9-tetrahydro-1H-carbazole-8-carboxylic acid | 400 MHz-CDCl3: 12.8 (br s, 1H), 7.73 (d, J = 8.0 Hz, 1H), 7.65 (d, J = 8.0 Hz, 1H), 7.13-7.04 (m, 3H), 6.88 (t, J = 8.0 Hz, 1H), 5.89 (d, J = 8.0 Hz, 1H), 5.58-5.55 (m, 2H), 2.89-2.83 (m, 1H), 2.75-2.67 (m, 2H), 2.36(s, 3H), 2.25-2.19(m, 1H), 2.06-2.00(m, 1H), 1.88 (br s, 1H), 1.54-1.27(m, 11H), 0.88 (t, J = 7.2 Hz, 3H) | 403.25 | 404.1 | Compound was synthesized by method A using 3-hexyl-1-cyclohexanone and 2-methyl-1-benzyl bromide as appropriate building blocks |
| 9-[(2-fluorophenyl)-methyl]-2-hexyl-2,3,4,9-tetrahydro-1H-carbazole-8-carboxylic acid | 400 MHz-CDCl3: 12.8 (br s, 1H), 7.71 (dd, J = 8.0, 2.4 Hz, 2H), 7.16-7.08 (m, 2H), 7.00(t, J = 8.8 Hz, 1H), 6.86 (t, J = 8.8 Hz, 1H), 6.25 (t, J = 8.0 Hz, 1H), 5.71 (d, J = 17.6 Hz, 1H), 5.65 (d, J = 17.6 Hz, 1H), 2.88-2.67 (m, 3H), 2.27-2.19(m, 1H), 2.05-2.00(m, 1H), 1.88 (br s, 1H), 1.54-1.27 (m, 11H), 0.88 (t, J = 7.2 Hz, 3H) | 407.23 | 408.1 | Compound was synthesized by method A using 3-hexyl-1-cyclohexanone and 2-fluoro-1-benzyl bromide as appropriate building blocks |
| 9-[(3-carbamoylphenyl)-methyl]-2-(2-phenylethyl)-2,3,4,9- | 400 MHz-DMSO d6: 12.80(br s, 1H), 7.88 (br s, 1H), 7.66 (d, J = 8 Hz, 1H), 7.61 (d, J = 8 Hz, 1H), 7.52 (br s, 1H), 7.41 (d, J = 7.2 Hz, 1H), 7.31 (br s, 1H), 7.27-7.22 (m, 3H), 7.18-7.14 | 452.21 | 453.1 | Compound was synthesized by method A using 3-ethyl-1-cyclohexanone and |

TABLE 1-continued

| IUPAC Name | 1H NMR | Exact Mass (g) | Observed [M + H]/Z | Synthetic Method |
|---|---|---|---|---|
| tetrahydro-1H-carbazole-8-carboxylic acid | (m, 3H), 7.04 ( t, J = 8 Hz, 1H), 6.66 (d, J = 8 Hz, 1H), 5.66( s, 2H), 2.91-2.86(m, 1H), 2.82-2.72 (m, 1H), 2.66-2.63(m, 3H) 2.35-2.30 (m, 1H), 1.82 (br s, 1H), 1.76-1.63 (m, 2H), 1.55-1.48(m, 1H) | | | 3-cyano-1-benzyl bromide as appropriate building blocks |
| 9-[(3-cyanophenyl)-methyl]-2-(2-phenylethyl)-2,3,4,9-tetrahydro-1H-carbazole-8-carboxylic acid | 400 MHz-DMSO d6: 12.87(br s, 1H), 7.67 (d, J = 7.6 Hz, 1H), 7.62 (d, J = 7.6 Hz, 1H), 7.45-7.40 (m, 2H), 7.27-7.23 ( m, 3H), 7.18-7.13 (m, 3H), 7.05 ( t, J = 8 Hz, 1H), 6.94 (d, J = 8 Hz, 1H), 5.66( s, 2H), 2.90-2.78 (m, 2H), 2.72-2.62 (m, 3H), 2.35-2.30 (m, 1H), 2.03-2.00 (m, 1H), 1.83(br s, 1H), 1.78-1.64 (m, 2H), 1.56-1.48 (m, 1H) | 434.20 | 435.1 | Compound was synthesized by method A using 3-ethyl-1-cyclohexanone and 3-cyano-1-benzyl bromide as appropriate building blocks |
| 9-[(3-carbamoylphenyl)-methyl]-4-(2-phenylethyl)-2,3,4,9-tetrahydro-1H-carbazole-8-carboxylic acid | 400 MHz-DMSO d6: 12.80(br s, 1H), 7.88 (br s, 1H), 7.63 (d, J = 8 Hz, 2H), 7.55 (d, J = 7.2 Hz, 1H), 7.50 (br s, 1H), 7.34-7.16 (m, 8H), 7.00 ( t, J = 8 Hz, 1H), 6.67 (d, J = 8 Hz, 1H), 5.67 (d, J = 17 Hz, 1H), 5.57( d, J = 17 Hz, 1H), 3.04-3.00(m, 1H), 2.78-2.67(m, 3H), 2.59-2.5-[(m, 1H) 2.15-2.02 (m, 1H), 1.90-1.85 (m, 4H) | 452.21 | 453.1 | Compound was synthesized by method A using 3-ethyl-1-cyclohexanone and 3-cyano-1-benzyl bromide as appropriate building blocks |
| 9-[(3-cyanophenyl)-methyl]-4-(2-phenylethyl)-2,3,4,9-tetrahydro-1H-carbazole-8-carboxylic acid | 400 MHz-DMSO d6: 12.81(br s, 1H), 7.64 (d, J = 8 Hz, 1H), 7.55 (d, J = 8 Hz, 1H), 7.41 (t, J = 8 Hz, 1H), 7.36-7.24 ( m, 6H), 7.18 ( m, 1H), 7.01 ( t, J = 8 Hz, 1H), 6.94 (d, J = 8 Hz, 1H), 5.68( d, J = 18 Hz, 1H), 5.60 (d, J = 18 Hz, 1H), 3.03-2.90 (m, 1H), 2.81-2.74 ( m, 1H), 2.72-2.63 (m, 2H), 2.57-2.55 (m, 1H), 2.13-2.05 (m, 1H), 1.93-1.80 (m, 5H) | 434.20 | 435.1 | Compound was synthesized by method A using 3-ethyl-1-cyclohexanone and 3-cyano-1-benzyl bromide as appropriate building blocks |
| 9-[(3-carbamoylphenyl)-methyl]-2-propyl-2,3,4,9-tetrahydro-1H-carbazole-8-carboxylic acid | 400 MHz-DMSO d6: 12.80(br s, 1H), 7.87 (br s, 1H), 7.64 (d, J = 8 Hz, 1H), 7.62 (d, J = 8 Hz, 1H), 7.49 ( s, 1H), 7.39 (d, J = 7.2 Hz, 1H), 7.30 (br s, 1H), 7.24 ( t, J = 8 Hz, 1H), 7.03 ( t, J = 8 Hz, 1H), 6.65 (d, J = 8 Hz, 1H), 5.68 ( d, J = 17 Hz, 1H), 5.62( d, J = 17 Hz, 1H) 2.84-2.77 (m, 2H), 2.70-2.60(m, 1H), 2.27-2.21 (m, 1H), 1.98-1.94 (m, 1H), 1.83 (br s, 1H), 1.46-1.24(m, 5H), 0.85 (m, 3H) | 390.19 | 391.1 | Compound was synthesized by method A using 3-propyl-1-cyclohexanone and 3-cyano-1-benzyl bromide as appropriate building blocks |
| 9-[(3-cyanophenyl)-methyl]-2-propyl-2,3,4,9-tetrahydro-1H-carbazole-8-carboxylic acid | 400 MHz-DMSO d6: 12.81(br s, 1H), 7.65 (t, J = 8 Hz, 2H), 7.42 (t, J = 8 Hz, 2H), 7.23 (br s, 1H), 7.06 ( t, J = 8 Hz, 1H), 6.92 (d, J = 8 Hz, 1H), 5.67( d, J = 13 Hz, 1H), 5.60 (d, J = 13 Hz, 1H), 2.83-2.77 (m, 2H), 2.66-2.60 (m, 1H), 2.27-2.21 ( m, 1H), 1.98-1.95 (m, 1H), 1.90-1.80 (m, 1H), 1.48-1.34(m, 5H), 0.85 (m, 3H) | 372.18 | 373.1 | Compound was synthesized by method A using 3-propyl-1-cyclohexanone and 3-cyano-1-benzyl bromide as appropriate building blocks |
| 2-butyl-9-[(3-carbamoylphenyl)-methyl]-2,3,4,9-tetrahydro-1H-carbazole-8-carboxylic acid | 400 MHz-DMSO d6: 12.80(br s, 1H), 7.87 (br s, 1H), 7.64 (d, J = 8 Hz, 1H), 7.62 (d, J = 8 Hz, 1H), 7.49 ( s, 1H), 7.39 (d, J = 7.2 Hz, 1H), 7.30 (br s, 1H), 7.25 ( t, J = 8 Hz, 1H), 7.04 ( t, J = 8 Hz, 1H), 6.64 (d, J = 8 Hz, 1H), 5.68 ( d, J = 17 Hz, 1H), 5.62( d, J = 17 Hz, 1H) 2.84-2.77 (m, 2H), 2.70-2.60(m, 1H), 2.27-2.21 (m, 1H), 1.98-1.94 (m, 1H), 1.83 (br s, 1H), 1.46-1.24(m, 7H), 0.85 (t, J = 7.2 Hz, 3H) | 404.21 | 405.1 | Compound was synthesized by method A using 3-butyl-1-cyclohexanone and 3-cyano-1-benzyl bromide as appropriate building blocks |
| 9-[(3-carbamoylphenyl)-methyl]-2-pentyl-2,3,4,9-tetrahydro-1H-carbazole-8-carboxylic acid | 400 MHz-DMSO d6: 12.80(br s, 1H), 7.87 (br s, 1H), 7.66-7.61 (m, 2H), 7.48 ( s, 1H), 7.40 (d, J = 7.2 Hz, 1H), 7.30 (br s, 1H), 7.24 ( t, J = 8 Hz, 1H), 7.04 ( t, J = 8 Hz, 1H), 6.64 (d, J = 8 Hz, 1H), 5.68 ( d, J = 17 Hz, 1H), 5.62( d, J = 17 Hz, 1H) 2.84-2.77 (m, 2H), 2.70-2.60(m, 1H), 2.27-2.21 (m, 1H), 2.00-1.90 (m, 1H), 1.84 (br s, 1H), 1.42-1.20(m, 9H), 0.85 (t, J = 7.2 Hz, 3H) | 418.23 | 419.1 | Compound was synthesized by method A using 3-pentyl-1-cyclohexanone and 3-cyano-1-benzyl bromide as appropriate building blocks |

TABLE 1-continued

| IUPAC Name | 1H NMR | Exact Mass (g) | Observed [M + H]/Z | Synthetic Method |
|---|---|---|---|---|
| 9-[(3-cyanophenyl)-methyl]-2-pentyl-2,3,4,9-tetrahydro-1H-carbazole-8-carboxylic acid | 400 MHz-DMSO d6: 12.81(br s, 1H), 7.65 (t, J = 8 Hz, 2H), 7.42 (t, J = 8 Hz, 2H), 7.23 (br s, 1H), 7.06 ( t, J = 8 Hz, 1H), 6.93 (d, J = 8 Hz, 1H), 5.67( d, J = 16 Hz, 1H), 5.60 (d, J = 16 Hz, 1H), 2.83-2.73 (m, 2H), 2.66-2.60 (m, 1H), 2.27-2.21 (m, 1H), 2.05-1.95 (m, 1H), 1.90-1.80 (m, 1H), 1.48-1.34(m, 9H), 0.85 (t, J = 6.8 Hz, 3H) | 400.22 | 401.1 | Compound was synthesized by method A using 3-pentyl-1-cyclohexanone and 3-cyano-1-benzyl bromide as appropriate building blocks |
| 1-butyl-9-[(3-carbamoylphenyl)-methyl]-2,3,4,9-tetrahydro-1H-carbazole-8-carboxylic acid | 400 MHz-DMSO d6: 12.80(br s, 1H), 7.84 (br s, 1H), 7.66-7.61 (m, 2H), 7.44 (s, 1H), 7.38 (d, J = 7.2 Hz, 1H), 7.29 (br s, 1H), 7.20 ( t, J = 8 Hz, 1H), 7.03 ( t, J = 8 Hz, 1H), 6.51 (d, J = 8 Hz, 1H), 5.78 ( d, J = 16 Hz, 1H), 5.47( d, J = 16 Hz, 1H) 2.84-2.77 (m, 2H), 2.65-2.55 (m, 1H), 2.00-1.90 (m, 1H), 1.90-1.70 (m, 3H), 1.55-1.15(m, 6H), 0.81 (t, J = 7.2 Hz, 3H) | 404.21 | 405.1 | Compound was synthesized by method B using butyl-magnesium bromide as appropriate building blocks and 3-cyano-1-benzyl bromide as appropriate building blocks |
| 9-[(3-carbamoylphenyl)-methyl]-1-(pentyloxy)-2,3,4,9-tetrahydro-1H-carbazole-8-carboxylic acid | 400 MHz-DMSO d6: 12.80(br s, 1H), 7.91 (br s, 1H), 7.66-7.55 (m, 3H), 7.40-7.35 (m, 1H), 7.26 (br s, 1H), 7.20 ( t, J = 8 Hz, 1H), 7.02 ( t, J = 8 Hz, 1H), 6.70 (m, 1H), 5.81( m, 1H), 5.59(d, J = 16 Hz, 1H), 4.5 ( br s, 1H), 3.62-3.55 ( m, 1H), 3.41-3.35(m, 1H), 2.84-2.77 (m, 1H), 2.65-2.55 (m, 1H), 2.25-2.15 (m, 1H), 1.90-1.81.(m, 2H), 1.80-1.65 (m, 1H), 1.40-1.30(m, 2H), 1.35-1.10(m, 4H), 0.78 (t, J = 6.4 Hz, 3H) | 434.22 | 433.2 [M − H]− | Compound was synthesized by method B using 1-hexanol and 3-cyano-1-benzyl bromide as appropriate building blocks |
| 9-[(3-cyanophenyl)-methyl]-1-(pentyloxy)-2,3,4,9-tetrahydro-1H-carbazole-8-carboxylic acid | 400 MHz-DMSO d6: 12.80(br s, 1H), 7.72 (d, J = 8 Hz, 1H), 7.62 (d, J = 8 Hz, 1H), 7.49 ( s, 1H), 7.43 (d, J = 7.2 Hz, 1H), 7.39 ( t, J = 8 Hz, 1H), 7.24 (br s, 1H), 7.07 ( t, J = 8 Hz, 1H), 6.98 (d, J = 8 Hz, 1H), 5.71 ( d, J = 17 Hz, 1H), 5.60( d, J = 17 Hz, 1H) 4.5 ( br s, 1H), 3.62-3.55 (m, 1H), 3.41-3.35(m, 1H), 2.87-2.80 (m, 1H), 2.62-2.55 (m, 1H), 2.25-2.20 (m, 1H), 1.90-1.81.(m, 2H), 1.80-1.70 (m, 1H), 1.26-1.20(m, 2H), 1.18-1.00(m, 4H), 0.74 (t, J = 6.4 Hz, 3H) | 416.21 | 415.1 [M − H]− | Compound was synthesized by method B using 1-hexanol and 3-cyano-1-benzyl bromide as appropriate building blocks |
| 1-butyl-9[(3-cyanophenyl)-methyl]-2,3,4,9-tetrahydro-1H-carbazole-8-carboxylic acid | 400 MHz-DMSO d6: 12.81(br s, 1H), 7.64 (d, J = 8 Hz, 2H), 7.40-7.36 (m, 2H), 7.19 (br s, 1H), 7.05 ( t, J = 8 Hz, 1H), 6.78 (d, J = 8 Hz, 1H), 5.74 (d, J = 16 Hz, 1H), 5.50 (d, J = 16 Hz, 1H), 2.84-2.77 (m, 2H), 2.65-2.55 (m, 1H), 2.00-1.90 (m, 1H), 1.90-1.70 (m, 3H), 1.55-1.15(m, 6H), 0.81 (t, J = 7.2 Hz, 3H) | 386.20 | 387.1 | Compound was synthesized by method B using butyl-magnesium bromide and 3-cyano-1-benzyl bromide as appropriate building blocks |
| 6-butyl-5-[(3-carbamoylphenyl)-methyl]-5H,6H,7H,8H,9H,10H-cyclohepta[b]-indole-4-carboxylic acid | 400 MHz-DMSO d6: 12.81(br s, 1H), 7.84 (br s, 1H), 7.66 (t, J = 8 Hz, 2H), 7.50 ( s, 1H), 7.35 (d, J = 7.2 Hz, 1H), 7.27 (br s, 1H), 7.23 ( t, J = 8 Hz, 1H), 7.02 ( t, J = 8 Hz, 1H), 6.67 (d, J = 8 Hz, 1H), 5.81 ( d, J = 18 Hz, 1H), 5.55( d, J = 18 Hz, 1H), 3.05-2.95 ( m, 2H), 2.62-2.55(m, 1H), 1.92-1.65 (m, 4H), 1.62-1.55(m, 1H), 1.50-1.40(m, 1H), 1.40-1.20 (m, 3H), 1.17-1.08(m, 2H), 1.08-0.98 (m, 1H), 0.74 (t, J = 7.2 hz, 3H) | 418.23 | 419.1 | Compound was synthesized by method B using 5-[(3-carbamoylphenyl)methyl]-5H,6H,7H,8H, 9H, 10H-cyclohepta[b]-indole-4-carboxylic acid and butyl-magnesium bromide as appropriate building blocks |
| 6-butyl-5-[(3-cyanophenyl)-methyl]-5H,6H,7H,8H, | 400 MHz-CDCl3: 12.81(br s, 1H), 7.76 (d, J = 7.6 Hz, 1H), 7.71 (d, J = 7.6 Hz, 1H), 7.47 ( d, J = 8.0 Hz, 1H), 7.30 (t, J = 8.0 Hz, 1H), 7.15-7.10 (m, | 400.22 | 401.1 | Compound was synthesized by method B using 5-[(3-cyanophenyl) |

TABLE 1-continued

| IUPAC Name | 1H NMR | Exact Mass (g) | Observed [M + H]/Z | Synthetic Method |
|---|---|---|---|---|
| 9H,10H-cyclohepta[b]-indole-4-carboxylic acid | 2H), 7.02 ( d, J = 8 Hz, 1H), 5.90 ( d, J = 17.6 Hz, 1H), 5.48( d, J = 17.6 Hz, 1H), 3.09-3.05 ( m, 1H), 2.95-2.85(m, 1H), 2.73-2.65 (m, 1H), 2.05-1.86 (m, 4H), 1.77-1.46(m, 5H), , 1.40--1.08(m, 4H), 0.82 (t, J = 7.2 hz, 3H) | | | methyl]-5H,6H,7H,8H, 9H, 10H-cyclohepta[b]-indole-4-carboxylic acid and butyl-magnesium bromide as appropriate building blocks |
| 9-[(3-carbamoylphenyl)-methyl]-1-ethyl-2,3,4,9-tetrahydro-1H-carbazole-8-carboxylic acid | 400 MHz-DMSO d6: 12.68(br s, 1H), 7.83 (br s, 1H), 7.60 (d, J = 8 Hz, 1H), 7.41 (s, 1H), 7.35 (d, J = 6.8 Hz, 1H), 7.27 (br s, 1H), 7.18 ( t, J = 8 Hz, 1H), 7.02 (t, J = 8 Hz, 1H), 6.47 (d, J = 8 Hz, 1H), 5.77 ( d, J = 17.2 Hz, 1H), 5.43( d, J = 17.2 Hz, 1H), 2.79-2.70 ( m, 2H), 2.65-2.53(m, 1H), 1.98 (br d, J = 16 Hz, 1H), 1.82-1.69(m, 3H), 1.63-1.57(m, 1H), 1.50-1.42 (m, 1H), 0.94 (t, J = 7.2 hz, 3H) | 376.18 | 377.1 | Compound was synthesized by method B using 9-[(3-carbamoylphenyl)methyl]-2,3,4,9-tetrahydro-1H-carbazole-8-carboxylic acid and ethyl-magnesium bromide as appropriate building blocks |
| 9-[(3-cyanophenyl)-methyl]-1-ethyl-2,3,4,9-tetrahydro-1H-carbazole-8-carboxylic acid | 400 MHz-DMSO d6: 12.80(br s, 1H), 7.69 (d, J = 8.0 Hz, 1H), 7.60 (dd, J = 8.0, 1.2 Hz, 1H), 7.36-7.30(m, 2H), 7.26(t, J = 8.0 Hz, 1H), 7.01(t, J = 8.0 Hz, 1H), 6.71 (d, J = 8 Hz, 1H), 5.78 ( d, J = 17.2 Hz, 1H), 5.46( d, J = 17.2 Hz, 1H) 2.80-2.70 (m, 2H), 2.65-2.56 (m, 1H), 2.00-1.96 (m, 1H), 1.78-1.61(m, 3H), 1.59-1.50(m, 1H), 1.46-1.24(m, 1H), 0.94 (t, J = 7.2 Hz, 3H) | 358.17 | | Compound was synthesized by method B using 9-[(3-cyanophenyl)methyl]-2,3,4,9-tetrahydro-1H-carbazole-8-carboxylic acid and ethyl-magnesium bromide as appropriate building blocks |
| 9-[(3-carboxyphenyl)methyl]-1-ethyl-2,3,4,9-tetrahydro-1H-carbazole-8-carboxylic acid | 400 MHz-DMSO d6: 12.75(br s, 2H), 7.68 (d, J = 8.0 Hz, 1H), 7.60 (dd, J = 8.0, 1.2 Hz, 1H), 7.36-7.32(m, 2H), 7.26(t, J = 8.0 Hz, 1H), 7.01(t, J = 8.0 Hz, 1H), 6.71 (d, J = 8 Hz, 1H), 5.78 ( d, J = 17.2 Hz, 1H), 5.46( d, J = 17.2 Hz, 1H) 2.80-2.70 (m, 2H), 2.65-2.56 (m, 1H), 2.05-1.96 (m, 1H), 1.82-1.61(m, 3H), 1.62-1.52 (m, 1H), 1.50-1.42(m, 1H), 0.94 (t, J = 7.2 Hz, 3H) | 377.16 | 378.1 | Compound was synthesized by method B using 9-[(3-carboxylphenyl)-methyl]-2,3,4,9-tetrahydro-1H-carbazole-8-carboxylic acid and ethyl-magnesium bromide as appropriate building blocks |
| 9-[(3-carbamoylphenyl)-methyl]-1-propoxy-2,3,4,9-tetrahydro-1H-carbazole-8-carboxylic acid | 400 MHz-DMSO d6: 12.8(br s, 1H), 7.98 (br s, 1H), 7.63-7.59(m, 3H), 7.65 (d, J = 8.1 Hz, 1H), 7.33 (br s, 1H), 7.25 (br s, 1H), 7.19 ( t, J = 8 Hz, 1H), 6.99(br s, 1H), 6.78(br s, 1H), 5.89 (m, 1H), 5.56( d, J = 16.0 Hz, 1H), 4.53(s, 1H), 3.59-3.53(m, 1H), 3.41-3.39(m, 1H), 2.80(d, J = 16.0 Hz, 1H), 2.60-2.55(m, 2H), 2.21(d, J = 15.2 Hz, 1H), 1.90-1.65(m, 3H), 1.41(q, J = 6.4 Hz, 1H), 0.80 (t, J = 7.2 hz, 3H) | 406.19 | 405.1 [M − H]− | Compound was synthesized by method B using cyclohexanone and 1-propanol |
| 9-[(3-carbamoylphenyl)-methyl]-4-ethyl-2,3,4,9-tetrahydro-1H-carbazole-8-carboxylic acid | 300 MHz-DMSO d6: 12.8(br s, 1H), 7.90 (br s, 1H), 7.70 (d, J = 6.9 Hz, 1H), 7.65 (d, J = 8.1 Hz, 1H), 7.48 (s, 1H), 7.37 (d, J = 6.8 Hz, 1H), 7.33 (br s, 1H), 7.24 ( t, J = 8 Hz, 1H), 7.03 (t, J = 8 Hz, 1H), 6.65 (d, J = 7.8 Hz, 1H), 5.69 ( d, J = 17.1 Hz, 1H), 5.56( d, J = 17.1 Hz, 1H), 2.95-2.85 (m, aH), 2.75-2.65(m, 2H), 1.88-1.69(m, 4H), 1.60-1.48(m, 1H), 0.98 (t, J = 7.2 hz, 3H) | 376.18 | 377.1 | Compound was synthesized by method A using 3-ethyl-1-cyclohexanone and 3-cyano-1-benzyl bromide as appropriate building blocks |
| 4-[(3-carbamoylphenyl)-methyl]-3-ethyl- | 500 MHz-DMSO d6: 12.76 (br s, 1H), 7.87 (br s, 1H), 7.65 (d, J = 7.5 Hz, 2H), 7.57 (d, J = 7.5 Hz, 1H), 7.48 (s, 1H), 7.35 (d, J = 7.2 Hz, 1H), 7.31 (br s, | 362.16 | 363.1 | Compound was synthesized by method B using cyclopentantone |

TABLE 1-continued

| IUPAC Name | 1H NMR | Exact Mass (g) | Observed [M + H]/Z | Synthetic Method |
|---|---|---|---|---|
| 1H,2H,3H,4H-cyclopenta[b]-indole-5-carboxylic acid | 1H), 7.24 (t, J = 8 Hz, 1H), 7.03 (t, J = 8 Hz, 1H), 6.69 (d, J = 8 Hz, 1H), 5.73 (d, J = 17 Hz, 1H), 5.50 (d, J = 17 Hz, 1H) 2.84-2.77 (m, 2H), 2.67-2.64 (m, 1H), 2.22-2.18 (m, 1H), 1.69-1.66 (m, 1H), 1.47-1.42 (m, 1H), 0.84 (t, J = 7.2 Hz, 3H) | | | and ethyl-magnesium bromide as appropriate building blocks |
| 4-[(3-cyanophenyl)-methyl]-3-ethyl-1H,2H,3H,4H-cyclopenta[b]-indole-5-carboxylic acid | 400 MHz-DMSO d6: 12.80(br s, 1H), 7.66 (d, J = 8 Hz, 1H), 7.59 (d, J = 8 Hz, 1H), 7.41 (t, J = 8 Hz, 1H), 7.36 (d, J = 8 Hz, 1H), 7.25(s, 1H), 7.05 (t, J = 8 Hz, 1H), 6.92 (d, J = 8 Hz, 1H), 5.72(d, J = 16 Hz, 1H), 5.52 (d, J = 16 Hz, 1H), 3.25-3.15 (m, 1H), 2.86-2.65 (m, 3H), 2.23-2.15 (m, 1H), 2.00-1.90 (m, 1H), 1.90-1.70 (m, 3H), 1.55-1.15(m, 6H), 0.84 (t, J = 7.2 Hz, 3H) | 344.15 | 345.1 | Compound was synthesized by method B using cyclopentantone and ethyl-magnesium bromide as appropriate building blocks |
| 3-butyl-4-[(3-carbamoylphenyl)-methyl]-1H,2H,3H,4H-cyclopenta[b]-in dole-5-carboxylic acid | 500 MHz-DMSO d6: 12.76 (br s, 1H), 7.86 (br s, 1H), 7.65 (d, J = 7.5 Hz, 2H), 7.57 (d, J = 7.5 Hz, 1H), 7.49 (s, 1H), 7.36 (d, J = 7.2 Hz, 1H), 7.33 (br s, 1H), 7.24 (t, J = 8 Hz, 1H), 7.04 (t, J = 7.5 Hz, 1H), 6.71 (d, J = 8 Hz, 1H), 5.71 (d, J = 17.0 Hz, 1H), 5.52 (d, J = 17.0 Hz, 1H) 3.21(br s, 1H), 2.83-2.80 (m, 1H), 2.79-2.75 (m, 1H), 2.67-2.63 (m, 1H), 2.22-2.18 (m, 1H), 1.69-1.66 (m, 1H), 1.39-1.32 (m, 1H), 1.25-1.12 (m, 1H), 0.77 (t, J = 7.2 Hz, 3H) | 390.19 | 391.1 | Compound was synthesized by method B using cyclopentantone and butyl-magnesium bromide as appropriate building blocks |
| 3-butyl-4-[(3-cyanophenyl)-methyl]-1H,2H,3H,4H-cyclopenta[b]-indole-5-carboxylic acid | 400 MHz-DMSO d6: 12.80(br s, 1H), 7.88(br s, 1H), 7.68-7.63(m, 2H), 7.49 (br s, 1H), 7.41( t, J = 8 Hz, 1H), 7.36 (d, J = 8 Hz, 1H), 7.31(s, 1H), 7.24 ( t, J = 8 Hz, 1H), 7.03 ( t, J = 8 Hz, 1H), 6.67 (d, J = 8 Hz, 1H), 5.68 (d, J = 17.0 Hz, 1H), 5.56 (d, J = 17.0 Hz, 1H), 3.05-2.95 (m, 1H), 1.90-1.85 (m, 1H), 1.82-1.70 (m, 4H), 1.55-1.40(m, 3H), 0.84 (t, J = 7.2 Hz, 3H) | 372.18 | 373.1 | Compound was synthesized by method B using cyclopentantone and butyl-magnesium bromide as appropriate building blocks |
| 2-butyl-4-[(3-carbamoylphenyl)-methyl]-1H,2H,3H,4H-cyclopenta[b]-indole-5-carboxylic acid | 400 MHz-DMSO d6: 12.81 (br s, 1H), 7.88 (br s, 1H), 7.66 (d, J = 8.0 Hz, 2H), 7.55-7.52 (m, 2H), 7.37-7.24 (m, 3H), 7.02 ( t, J = 7.5 Hz, 1H), 6.80 (d, J = 7.2 Hz, 1H), , 5.58( s, 2H) 3.05-2.88 (m, 4H), 1.58-1.52 (m, 2H), 1.34-1.31 (m, 4H), 0.89 (t, J = 7.2 Hz, 3H) | 390.19 | 391.1 | Compound was synthesized by method A using 3-butyl-1-cyclopentanone and 3-cyano-1-benzyl bromide as appropriate building blocks |
| 2-butyl-4-[(3-cyanophenyl)-methyl]-1H, 2H, 3H, 4H-cyclopenta[b]-indole-5-carboxylic acid | 400 MHz-DMSO d6: 12.80(br s, 1H), 7.67 (d, J = 8 Hz, 1H), 7.57 (d, J = 8 Hz, 1H), 7.44( t, J = 8 Hz, 1H), 7.36 (d, J = 8 Hz, 1H), 7.30 (s, 1H), 7.04 (t, J = 8 Hz, 1H), 6.92 (d, J = 8 Hz, 1H), 5.58( s, 2H), 3.05-2.91 (m, 3H), 2.51-2.46 (m, 1H), 1.60-1.52(m, 2H), 1.36-1.28 (m, 4H), 0.89 (t, J = 7.2 Hz, 3H) | 372.18 | 373.1 | Compound was synthesized by method A using 3-butyl-1-cyclopentanone and 3-cyano-1-benzyl bromide as appropriate building blocks |
| 5-[(3-carbamoylphenyl)-methyl]-10-ethyl-5H,6H,7H,8H,9H,10H-cyclohepta[b]-indole-4-carboxylic acid | 400 MHz-DMSO d6 : 12.85(br s, 1H), 7.88 (br s, 1H), 7.66-7.63 (m, 2H), 2H), 7.47 (s, 1H), 7.34(d, J = 7.6 Hz, 1H), 7.28 (br s, 1H), 7.24 (t, J = 7.6 Hz, 1H), 7.02(t, J = 7.2 Hz, 1H), 6.70 ( d, J = 8.0 Hz, 1H), 5.74(d, J = 18.0 Hz, 1H), 5.65 (d, J = 18.0 Hz, 1H), 3.13(m, 1H) 2.93-2.88 (m, 1H), 2.69-2.61 (m, 1H), 2.05-2.00 (m, 1H), 1.88-1.80 (m, 3H), 1.67-1.55 (m, 3H), 1.33-1.24(m, 1H), 0.84 (t, J = 7.2 Hz, 3H) | 390.19 | 391.1 | Compound was synthesized by method A using 3-ethyl-1-cycloheptanone and 3-cyano-1-benzyl bromide as appropriate building blocks |
| 5-[(3-cyanophenyl)-methyl]-10-ethyl-5H,6H,7H,8H, | 400 MHz-DMSO d6: 12.90(br s, 1H), 7.70 (d, J = 8.0 Hz, 1H), 7.65 (d, J = 8.0 Hz, 1H), 7.44 (t, J = 8.0 Hz, 1H), 7.39(d, J = 6.8 Hz, 1H), 7.13 (br s, 1H), | 372.18 | 373.1 | Compound was synthesized by method A using 3-ethyl-1- |

TABLE 1-continued

| IUPAC Name | 1H NMR | Exact Mass (g) | Observed [M + H]/Z | Synthetic Method |
|---|---|---|---|---|
| 9H,10H-cyclohepta[b]-indole-4-carboxylic acid | 7.06 (t, J = 7.2 Hz, 1H), 6.97 ( d, J = 8.0 Hz, 1H), 5.68 (m, 2H), 3.16-3.13(m, 1H) 2.89-2.84 (m, 1H), 2.69-2.61 (m, 1H), 2.09-2.03 (m, 1H), 1.84-1.80 (m, 3H), 1.67-1.57 (m, 3H), 1.28-1.24(m, 1H), 0.84 (t, J = 7.2 Hz, 3H) | | | cycloheptanone and 3-cyano-1-benzyl bromide as appropriate building blocks |
| 5-[(3-carbamoylphenyl)-methyl]-10-propyl-5H,6H,7H,8H,9H,10H-cyclohepta[b]-indole-4-carboxylic acid | 500MHz-DMSO d6: 12.85(br s, 1H), 7.86 (br s, 1H), 7.68-7.64 (m, 2H), 7.45 (s, 1H), 7.37(d, J = 7.5 Hz, 1H), 7.29 (br s, 1H), 7.24 (t, J = 7.5 Hz, 1H), 7.04 (t, J = 7.2 Hz, 1H), 6.65 ( d, J = 8.0 Hz, 1H), 5.72 (d, J = 17.5 Hz, 1H), 5.63 (d, J = 17.5 Hz, 1H), 3.24(m, 1H) 2.93-2.88 (m, 1H), 2.65-2.63 (m, 1H), 2.05-2.00 (m, 1H), 1.88-1.82 (m, 3H), 1.62-1.55 (m, 3H), 1.33-1.24(m, 3H), 0.87 (t, J = 7.0 Hz, 3H) | 404.21 | 405.1 | Compound was synthesized by method A using 3-propyl-1-cycloheptanone and 3-cyano-1-benzyl bromide as appropriate building blocks |
| 5-[(3-cyanophenyl)-methyl]-10-propyl-5H,6H,7H,8H,9H,10H-cyclohepta[b]-indole-4-carboxylic acid | 400 MHz-DMSO d6: 12.90(br s, 1H), 7.63(d, J = 7.2 Hz, 1H), 7.58 (d, J = 7.2 Hz, 1H), 7.43 (t, J = 8.0 Hz, 1H), 7.29(d, J = 6.8 Hz, 1H), 7.03-6.99 (m, 2H), 5.74 (m, 2H), 3.16-3.13(m, 1H) 2.89-2.84 (m, 1H), 2.69-2.61 (m, 1H), 2.09-1.95 (m, 1H), 1.87-1.80 (m, 3H), 1.65-1.53 (m, 3H), 1.35-1.11(m, 3H), 0.86 (t, J = 7.2 Hz, 3H) | 386.20 | 387.1 | Compound was synthesized by method A using 3-propyl-1-cycloheptanone and 3-cyano-1-benzyl bromide as appropriate building blocks |
| 9-[(3-carboxyphenyl)methyl]-4-ethyl-2,3,4,9-tetrahydro-1H-carbazole-8-carboxylic acid | 300 MHz-DMSO d6: 12.85(br s, 1H), 7.72 (t, J = 7.2 Hz, 1H), 7.43(s, 1H), 7.38(d, J = 6.6 Hz, 1H), 7.33(t, J = 7.5 Hz, 1H), 7.04(t, J = 7.8 Hz, 1H), 6.88 ( d, J = 7.0 Hz, 1H), 5.67-5.59 (m, 2H) 2.90-2.86 (m, 1H), 2.76-2.73 (m, 1H), 2.64-2.58 (m, 2H), 2.30-2.25 (m, 1H), 2.07-2.00 (m, 1H), 1.66 (br s, 1H), 1.52-1.42(m, 3H), 0.98 (t, J = 6.0 Hz, 3H) | 377.16 | 378 | Compound was synthesized by method A using 3-ethyl-1-cyclohexanone and 3-cyano-1-benzyl bromide as appropriate building blocks |
| 9-[(3-carbamoylphenyl)-methyl]-3-ethyl-2,3,4,9-tetrahydro-1H-carbazole-8-carboxylic acid | 500 MHz-DMSO d6: 12.8(br s, 1H), 7.88 (br s, 1H), 7.65-7.63(m, 2H), 7.48(s, 1H), 7.41(dd, J = 7.0, 1.0 Hz, 1H), 7.31(s, 1H), 7.24(t, J = 7.0 Hz, 1H), 7.04(t, J = 7.0 Hz, 1H), 6.67 ( d, J = 7.0 Hz, 1H), 5.67-5.59 (m, 2H) 2.90-2.86 (m, 1H), 2.76-2.73 (m, 1H), 2.64-2.58 (m, 2H), 2.30-2.25 (m, 1H), 2.07-2.00 (m, 1H), 1.66 (br s, 1H), 1.52-1.42(m, 3H), 0.98 (t, J = 6.0 Hz, 3H) | 376.18 | 377.1 | Compound was synthesized by method A using 4-ethyl-1-cyclohexanone and 3-cyano-1-benzyl bromide as appropriate building blocks |
| 10-butyl-5-[(3-carbamoylphenyl)-methyl]-5H,6H,7H,8H,9H,10H-cyclohepta[b]-indole-4-carboxylic acid | 400 MHz-DMSO d6: 12.85(br s, 1H), 7.85 (br s, 1H), 7.65 (t, J = 7.6 Hz, 2H), 2H), 7.46(s, 1H), 7.37(d, J = 6.8 Hz, 1H), 7.28 (s, 1H), 7.24(t, J = 6.8 Hz, 1H), 7.04(t, J = 7.2 Hz, 1H), 6.64 ( d, J = 6.8 Hz, 1H), 5.72(d, J = 17.6 Hz, 1H), 5.65 (d, J = 17.6 Hz, 1H), 3.26-3.22(m, 1H) 2.93-2.88 (m, 1H), 2.69-2.61 (m, 1H), 2.02-1.95 (m, 1H), 1.88-1.82 (m, 3H), 1.66-1.53 (m, 3H), 1.33-1.24(m, 5H), 1.16-1.10 (m, 1H), 0.82 (t, J = 7.2 Hz, 3H) | 418.23 | 419.1 | Compound was synthesized by method A using 3-butyl-1-cycloheptanone and 3-cyano-1-benzyl bromide as appropriate building blocks |
| 10-butyl-5-[(3-cyanophenyl)-methyl]-5H,6H,7H,8H,9H,10H-cyclohepta[b]-indole-4-carboxylic acid | 400 MHz-DMSO d6: 12.89(br s, 1H), 7.69 (d, J = 7.2 Hz, 1H), 7.65 (d, J = 7.2 Hz, 1H), 7.44 (t, J = 7.6 Hz, 2H), 7.39 (d, J = 7.2 Hz, 1H), 7.10-7.05(m, 2H), 6.97 ( d, J = 7.6 Hz, 1H), 5.68 (s, 2H), 3.26-3.22(m, 1H) 3.26-3.23 (m, 1H), 2.90-2.86 (m, 1H), 2.67-2.60(m, 1H), 2.03-1.98 (m, 1H), 1.88-1.83 (m, 3H), 1.66-1.53 (m, 3H), 1.36-1.24(m, 4H), 1.12-1.07 (m, 1H), 0.82 (t, J = 6.8 Hz, 3H) | 400.22 | 401.1 | Compound was synthesized by method A using 3-butyl-1-cycloheptanone and 3-cyano-1-benzyl bromide as appropriate building blocks |
| 5-[(3-carbamoylphenyl)-methyl]-10-pentyl-5H,6H,7H,8H, 9H,10H- | 400 MHz-DMSO d6: 12.85(br s, 1H), 7.85 (br s, 1H), 7.65 (t, J = 7.2 Hz, 2H), 2H), 7.38 (s, 1H), 7.36(d, J = 7.6 Hz, 1H), 7.28 (s, 1H), 7.23(t, J = 8.0 Hz, 1H), 7.04(t, J = 7.6 Hz, 1H), 6.63 ( d, J = 7.6 Hz, 1H), 5.72(d, J = 18.0 Hz, | 432.24 | 433.1 | Compound was synthesized by method A using 3-pentyl-1-cycloheptanone and 3-cyano-1-benzyl |

TABLE 1-continued

| IUPAC Name | 1H NMR | Exact Mass (g) | Observed [M + H]/Z | Synthetic Method |
|---|---|---|---|---|
| cyclohepta[b]-indole-4-carboxylic acid | 1H), 5.64 (d, J = 18.0 Hz, 1H), 3.31-3.20(m, 1H) 2.92-2.87 (m, 1H), 2.69-2.61 (m, 1H), 2.02-1.95 (m, 1H), 1.88-1.82 (m, 3H), 1.66-1.53 (m, 3H), 1.33-1.14(m, 7H), 0.81 (t, J = 7.2 Hz, 3H) | | | bromide as appropriate building blocks |
| 5-[(3-cyanophenyl)-methyl]-10-pentyl-5H,6H,7H,8H,9H,10H-cyclohepta[b]-indole-4-carboxylic acid | 400 MHz-DMSO d6: 12.89(br s, 1H), 7.69 (d, J = 7.2 Hz, 1H), 7.65 (d, J = 7.2 Hz, 1H), 7.43 (t, J = 7.6 Hz, 1H), 7.39 (d, J = 7.2 Hz, 1H), 7.11-7.05(m, 2H), 6.98 ( d, J = 7.6 Hz, 1H), 5.68 (s, 2H), 3.26-3.22(m, 1H) 2.90-2.86 (m, 1H), 2.67-2.60(m, 1H), 2.03-1.98 (m, 1H), 1.88-1.83 (m, 3H), 1.66-1.53 (m, 3H), 1.36-1.07 (m, 7H), 0.81 (t, J = 6.8 Hz, 3H) | 414.23 | 415.1 | Compound was synthesized by method A using 3-pentyl-1-cycloheptanone and 3-cyano-1-benzyl bromide as appropriate building blocks |
| 4-[(3-carbamoylphenyl)-methyl]-2-pentyl-1H,2H,3H,4H-cyclopenta[b]-dole-5-carboxylic acid | 500 MHz-DMSO d6: 12.81 (br s, 1H), 7.87 (br s, 1H), 7.66 (d, J = 7.2 Hz, 2H), 7.55 (d, J = 7.2 Hz, 1H), 7.51 (s, 1H), 7.37 (d, J = 7.2 Hz, 1H), 7.31 (br s, 1H), 7.26 ( t, J = 8 Hz, 1H), 7.03 ( t, J = 8 Hz, 1H), 6.69 (d, J = 8 Hz, 1H), 5.60 ( s, 2H), 3.05-2.77 (m, 4H), 2.67-2.64 (m, 1H), 1.60-1.50 (m, 1H), 1.37-1.20 (m, 7H), 0.87 (t, J = 7.2 Hz, 3H) | 404.21 | 405.1 | Compound was synthesized by method A using 3-pentyl-1-cyclopentanone and 3-cyano-1-benzyl bromide as appropriate building blocks |
| 4-[(3-cyanophenyl) methyl]-2-pentyl-1H,2H,3H,4H-cyclopenta[b]-indole-5-carboxylic acid | 500 MHz-DMSO d6: 12.81 (br s, 1H), 7.57 (dd, J = 7.5, 1.0 Hz, 1H), 7.52 (d, J = 7.5 Hz, 1H), 7.46 (d, J = 7.5 Hz, 1H), 7.36 (t, J = 8.0 Hz, 1H), 7.19 (s, 1H), 7.06-7.03 (m, 2H), 5.61 ( s, 2H), 3.10-2.98 (m, 3H), 2.55-2.48 (m, 2H), 1.64-1.62 (m, 2H), 1.44-1.42 (m, 2H), 1.37-1.30 (m, 4H), 0.92 (t, J = 7.5 Hz, 3H) | 386.20 | 387.1 | Compound was synthesized by method A using 3-pentyl-1-cyclopentanone and 3-cyano-1-benzyl bromide as appropriate building blocks |
| 9-[(3-carbamoylphenyl)-methyl]-2-ethyl-2,3,4,9-tetrahydro-1H-carbazole-8-carboxylic acid | 300 MHz-DMSO d6: 8.14(br s, 1H), 7.90 (br s, 1H), 7.64(t, J = 6.9 Hz, 1H), 7.48(s, 1H), 7.40 (d, J = 7.2 Hz, 1H), 7.33 (s, 1H), 7.24 (t, J = 7.5 Hz, 1H), 7.04(t, J = 7.2 Hz, 1H), 6.64 ( d, J = 7.8 Hz, 1H), 5.65( q, J = 1 Hz, 1H) 2.80-2.70 (m, 2H), 2.65-2.55 (m, 1H), 2.25-2.15 (m, 1H), 1.98-1.94 (m, 1H), 1.67 (br s, 1H), 1.50-1.24(m, 8H), 0.89 (t, J = 6.4 Hz, 3H) | 376.18 | 377.1 | Compound was synthesized by method A using 3-ethyl-1-cyclohexanone and 3-cyano-1-benzyl bromide as appropriate building blocks |
| 9-[(3-carboxyphenyl) methyl]-2-ethyl-2,3,4,9-tetrahydro-1H-carbazole-8-carboxylic acid | 300 MHz-DMSO d6: 12.85(br s, 2H), 7.73(d, J = 7.8 Hz, 1H), 7.64(d, J = 7.8 Hz, 1H), 7.45(s, 1H), 7.41 (d, J = 7.2 Hz, 1H), 7.33 (t, J = 7.5 Hz, 1H), 7.04(t, J = 7.2 Hz, 1H), 6.87 ( d, J = 7.8 Hz, 1H), 5.66( m, 2H) 2.87-2.73 (m, 2H), 2.68-2.57 (m, 1H), 2.28-2.20 (m, 1H), 2.04-1.98 (m, 1H), 1.76(br s, 1H), 1.50-1.34(m, 3H), 0.93 (t, J = 6.4 Hz, 3H) | 377.16 | 378.1 | Compound was synthesized by method A using 3-ethyl-1-cyclohexanone and 3-cyano-1-benzyl bromide as appropriate building blocks |
| 5-[(3-carbamoylphenyl)-methyl]-7-ethyl-5H,6H,7H,8H,9H,10H-cyclohepta[b]-indole-4-carboxylic acid | 400 MHz-DMSO d6: 12.85(br s, 1H), 7.87(br s, 1H), 7.67(t, J = 7.2 Hz, 1H), 7.50(s, 1H), 7.38 (d, J = 7.2 Hz, 1H), 7.29 (s, 1H), 7.26 (t, J = 7.2 Hz, 1H), 7.04(t, J = 7.2 Hz, 1H), 6.73 ( d, J = 7.8 Hz, 1H), 5.78( d, J = 17.6 Hz, 1H), 5.61( d, J = 17.6 Hz, 1H) 2.93-2.82 (m, 2H), 2.72-2.66 (m, 1H), 1.94-1.85 (m, 1H), 1.57-1.46 (m, 2H), 1.36(br s, 1H), 1.22-1.14(m, 2H), 0.68 (t, J = 7.6 Hz, 3H) | 390.19 | 391.1 | Compound was synthesized by method A using 3-ethyl-1-cycloheptanone and 3-cyano-1-benzyl bromide as appropriate building blocks |
| 5-[(3-cyanophenyl)-methyl]-7-ethyl-5H,6H,7H,8H,9H,10H-cyclohepta[b]-indole-4-carboxylic acid | 400 MHz-DMSO d6: 12.87(br s, 1H), 7.68 (t, J = 8 Hz, 2H), 7.44 ( t, J = 8 Hz, 1H), 7.41(d, J = 8 Hz, 1), 7.27 (br s, 1H), 7.06 ( t, J = 8 Hz, 1H), 6.99 (d, J = 8 Hz, 1H), 5.78 ( d, J = 18 Hz, 1H), 5.62( J = 18 Hz, 1H), 2.92 (dd, J = 15.6, 7.2 Hz, 1H), 2.81 ( d, J = 16 Hz, 1H), 2.72-2.67(m, 1H), 2.51 (m, 1H), 1.95-1.89 (m, 2H), 1.56-1.53(m, 2H), 1.32(m, 1H), 1.22(m, 2H), 0.68 (t, J = 7 Hz, 3H) | 372.18 | 373.1 | Compound was synthesized by method A using 3-ethyl-1-cycloheptanone and 3-cyano-1-benzyl bromide as appropriate building blocks |

TABLE 1-continued

| IUPAC Name | 1H NMR | Exact Mass (g) | Observed [M + H]/Z | Synthetic Method |
|---|---|---|---|---|
| 9-[(3-cyanophenyl)-methyl]-3-ethyl-2,3,4,9-tetrahydro-1H-carbazole-8-carboxylic acid | 500 MHz-DMSO d6: 12.82 (br s, 1H), 7.66 (t, J = 8 Hz, 2H), 7.45-7.41 (m, 2H), 7.25 (s, 1H), 7.06 (t, J = 8.0 Hz, 1H), 6.93 (d, J = 8.0 Hz, 1H), 5.66-5.58(m, 2H), 2.88(dd, J = 16, 4 Hz, 1H), 2.75-2.70 (m, 1H), 2.65-2.60 (m, 1H), 2.54-2.48 (m, 2H), 2.30-2.25 (m, 1H), 2.03-2.00 (m, 1H), 1.67 (m, 1H), 1.53-1.42(m, 3H), 0.99 (t, J = 7.5 Hz, 3H) | 358.17 | 359.1 | Compound was synthesized by method A using 4-ethyl-1-cyclohexanone and 3-cyano-1-benzyl bromide as appropriate building blocks |
| 9-[(3-carbamoylphenyl)-methyl]-4-propyl-2,3,4,9-tetrahydro-1H-carbazole-8-carboxylic acid | 500 MHz-DMSO d6 : 12.8(br s, 1H), 7.86 (br s, 1H), 7.69 (d, J = 7.5 Hz, 1H), 7.64 (d, J = 7.5 Hz, 1H), 7.48 (s, 1H), 7.38 (d, J = 7.5 Hz, 1H), 7.30 (br s, 1H), 7.24 ( t, J = 7.5 Hz, 1H), 7.04 (t, J = 7.5 Hz, 1H), 6.66 (d, J = 7.5 Hz, 1H), 5.68 ( d, J = 17.0 Hz, 1H), 5.56( d, J = 17.0 Hz, 1H), 3.02-2.99 (m, 1H), 2.70-2.64(m, 1H), 2.51-2.49(m, 1H), 1.89-1.88(m, 1H), 1.82-1.75(m, 4H), 1.53-1.40(m, 3H), 0.95 (t, J = 7.2 hz, 3H) | 390.19 | 391.1 | Compound was synthesized by method A using 3-propyl-1-cyclohexanone and 3-cyano-1-benzyl bromide as appropriate building blocks |
| 9-[(3-carbamoylphenyl)-methyl]-3-propyl-2,3,4,9-tetrahydro-1H-carbazole-8-carboxylic acid | 400 MHz-DMSO d6: 12.8(br s, 1H), 7.87 (br s, 1H), 7.64 (m, 2H), 7.48 (s, 1H), 7.40(d, J = 7.6 Hz, 1H), 7.30(s, 1H), 7.24 (t, J - 8.0 Hz, 1H), 7.04(t, J - 8.0 Hz, 1H), 6.68 ( d, J = 7.6 Hz, 1H), 5.66-5.56(m, 2H) 2.90-2.85 (m, 1H), 2.72-2.62 (m, 2H), 2.33-2.25 (m, 1H), 2.02-1.98 (m, 1H), 1.76 (br s, 1H), 1.52-1.36(m, 5H), 0.92 (t, J = 7.0 Hz, 3H) | 390.19 | 391.1 | Compound was synthesized by method A using 4-propyl-1-cyclohexanone and 3-cyano-1-benzyl bromide as appropriate building blocks |
| 9-[(3-cyanophenyl)-methyl]-3-propyl-2,3,4,9-tetrahydro-1H-carbazole-8-carboxylic acid | 400 MHz-DMSO d6: 12.82 (br s, 1H), 7.66-7.63 (m, 2H), 7.44-7.40 (m, 2H), 7.24 (s, 1H), 7.06 (t, J = 8 Hz, 1H), 6.94 (d, J = 8 Hz, 1H), 5.62 (s, 2H), 2.87(dd, J = 16, 4 Hz, 1H), 2.70-2.55 (m, 2H), 2.31-2.45 (m, 1H), 2.05-1.95 (m, 1H), 1.78 (br s, 1H), 1.52-1.41(m,, 5H), 0.93 (t, J = 8 Hz, 3H) | 372.18 | 373.1 | Compound was synthesized by method A using 4-propyl-1-cyclohexanone and 3-cyano-1-benzyl bromide as appropriate building blocks |
| 4-butyl-9-[(3-carbamoylphenyl)-methyl]-2,3,4,9-tetrahydro-1H-carbazole-8-carboxylic acid | 500 MHz-DMSO d6: 12.8(br s, 1H), 7.86 (br s, 1H), 7.68-7.64 (m, 2H), 7.48 (s, 1H), 7.37 (d, J = 7.0 Hz, 1H), 7.31 (br s, 1H), 7.24 ( t, J = 7.5 Hz, 1H), 7.04 (t, J = 7.5 Hz, 1H), 6.65 (d, J = 7.5 Hz, 1H), 5.68 ( d, J = 17.0 Hz, 1H), 5.56 (d, J = 17.0 Hz, 1H), 3.01-2.98 (m, 1H), 2.70-2.64(m, 2H), 1.89-1.76 (m, 5H), 1.52-1.31(m, 5H), 0.90 (t, J = 7.0 hz, 3H) | 404.21 | 405.1 | Compound was synthesized by method A using 3-butyl-1-cyclohexanone and 3-cyano-1-benzyl bromide as appropriate building blocks |
| 4-butyl-9-[(3-cyanophenyl)-methyl]-2,3,4,9-tetrahydro-1H-carbazole-8-carboxylic acid | 500 MHz-DMSO d6: 12.8(br s, 1H), 7.709-7.65 (m, 2H), 7.44-7.38 (m, 2H), 7.22 (br s, 1H), 7.06 (t, J = 8.0 Hz, 1H), 6.93 (d, J = 8.0 Hz, 1H), 5.64 ( d, J = 17.5 Hz, 1H), 5.56 (d, J = 17.5 Hz, 1H), 3.01-2.98 (m, 1H), 2.65-2.62(m, 1H), 2.56-2.50(m, 1H), 1.89-1.76 (m, 5H), 1.54-1.50(m, 1H), 1.42-1.31(m, 4H), 0.90 (t, J = 7.0 hz, 3H) | 386.20 | 387.1 | Compound was synthesized by method A using 3-butyl-1-cyclohexanone and 3-cyano-1-benzyl bromide as appropriate building blocks |
| 3-butyl-9-[(3-carbamoylphenyl)-methyl]-2,3,4,9-tetrahydro-1H-carbazole-8-carboxylic acid | 400 MHz-DMSO d6: 8.14(br s, 1H), 7.86 (br s, 1H), 7.57 (d, J = 9 Hz, 1H), 7.30-7.16 (m, 3H), 7.10-6.95 (m, 2H), 6.82 ( t, J = 7.2 Hz, 1H), 5.85 ( d, J = 16 Hz, 1H), 5.71( d, J = 16 Hz, 1H) 2.80-2.70 (m, 2H), 2.65-2.55 (m, 1H), 2.25-2.15 (m, 1H), 1.98-1.94 (m, 1H), 1.67 (br s, 1H), 1.50-1.24(m, 8H), 0.89 (t, J = 6.4 Hz, 3H) | 404.21 | 405.1 | Compound was synthesized by method A using 3-pentyl-1-cyclohexanone and 3-cyano-1-benzyl bromide as appropriate building blocks |
| 3-butyl-9-[(3-cyanophenyl)-methyl]-2,3,4,9-tetrahydro-1H-carbazole-8-carboxylic acid | 400 MHz-DMSO d6: 12.82 (br s, 1H), 7.65 (t, J = 8 Hz, 2H), 7.42 (t, J = 8 Hz, 2H), 7.23 (s, 1H), 7.05 (t, J = 8 Hz, 1H), 6.93 (d, J = 8 Hz, 1H), 5.62(s, 2H), 2.86(dd, J = 16, 4 Hz, 1H), 2.75-2.65 (m, 1H), 2.65-2.55 (m, 1H), 2.28 (dd, J = 15, 5 Hz, 1H), 2.05-1.95 (m, 1H), 1.75 (m, 1H), 1.55-1.45(m, 1H), 1.45-1.30(m, 6H), 0.90 (t, J = 8 Hz, 3H) | 386.20 | 387.4 | Compound was synthesized by method A using 4-butyl-1-cyclohexanone and 3-cyano-1-benzyl bromide as appropriate building blocks |

TABLE 1-continued

| IUPAC Name | 1H NMR | Exact Mass (g) | Observed [M + H]/Z | Synthetic Method |
|---|---|---|---|---|
| 9-[(3-carbamoylphenyl)-methyl]-4-pentyl-2,3,4,9-tetrahydro-1H-carbazole-8-carboxylic acid | 400 MHz-DMSO d6: 12.8(br s, 1H), 7.87 (br s, 1H), 7.66 (t, J = 8.4 Hz, 2H), 7.49 (s, 1H), 7.38 (d, J = 7.2 Hz, 1H), 7.30 (br s, 1H), 7.24 ( t, J = 7.6 Hz, 1H), 7.04 (t, J = 7.6 Hz, 1H), 6.65 (d, J = 8.0 Hz, 1H), 5.67 ( d, J = 17.6 Hz, 1H), 5.55 (d, J = 17.6 Hz, 1H), 3.01-2.98 (m, 1H), 2.71-2.64(m, 1H), 2.55-2.48(m, 1H), 1.89-1.76 (m, 5H), 1.55-1.33(m, 7H), 0.88 (t, J = 6.8 hz, 3H) | 418.23 | 419.1 | Compound was synthesized by method A using 3-pentyl-1-cyclohexanone and 3-cyano-1-benzyl bromide as appropriate building blocks |
| 9-[(3-cyanophenyl)-methyl]-4-pentyl-2,3,4,9-tetrahydro-1H-carbazole-8-carboxylic acid | 500 MHz-DMSO d6: 12.8(br s, 1H), 7.70-7.65 (m, 2H), 7.44-7.38 (m, 2H), 7.22 (br s, 1H), 7.06 (t, J = 8.0 Hz, 1H), 6.93 (d, J = 8.0 Hz, 1H), 5.64 ( d, J = 17.6 Hz, 1H), 5.56 (d, J = 17.6 Hz, 1H), 3.01-2.98 (m, 1H), 2.68-2.63(m, 1H), 2.56-2.50(m, 1H), 1.89-1.76 (m, 5H), 1.57-1.31(m, 7H), 0.88 (t, J = 7.2 hz, 3H) | 400.22 | 401.1 | Compound was synthesized by method A using 3-pentyl-1-cyclohexanone and 3-cyano-1-benzyl bromide as appropriate building blocks |
| 9-[(3-carbamoylphenyl)-methyl]-3-pentyl-2,3,4,9-tetrahydro-1H-carbazole-8-carboxylic acid | 400 MHz-DMSO d6: 12.8(br s, 1H), 7.66 (d, J = 7.6 Hz, 2H), 7.44-7.40(m, 2H), 7.23(s, 1H), 7.05(t, J = 7.6 Hz, 1h), 6.93 ( t, J = 7.2 Hz, 1H), 5.61 (s, 2H) 2.90-2.85(m, 1H), 2.73-2.60 (m, 2H), 2.32-2.25 (m, 1H), 2.02-1.98 (m, 1H), 1.75 (br s, 1H), 1.55-1.51(m, 1H), 1.41(br s, 4H), 1.34-1.23(m, 4H), 0.88 (t, J = 6.8 Hz, 3H) | 418.23 | 419.1 | Compound was synthesized by method A using 4-pentyl-1-cyclohexanone and 3-cyano-1-benzyl bromide as appropriate building blocks |
| 9-[(3-cyanophenyl)-methyl]-3-pentyl-2,3,4,9-tetrahydro-1H-carbazole-8-carboxylic acid | 400 MHz-DMSO d6: 12.8(br s, 1H), 7.87 (br s, 1H), 7.64 (d, J = 6.8 Hz, 1H), 7.48(s, 1H), 7.40 (d, J = 7.6 Hz, 1H) 7.30(s, 1H), 7.24(t, J = 7.6 Hz, 1H), 7.03(t, J = 7.6 Hz, 1h), 6.67 ( t, J = 7.2 Hz, 1H), 5.64 ( s, 2H) 2.87(dd, J =12.0, 4.8 Hz, 1H), 2.71-2.50 (m, 2H), 2.32-2.25 (m, 1H), 2.02-1.98 (m, 1H), 1.74 (br s, 1H), 1.51-1.24(m, 9H), 0.88 (t, J = 6.8 Hz, 3H) | 400.22 | 401.1 | Compound was synthesized by method A using 4-hexyl-1-cyclohexanone and 3-cyano-1-benzyl bromide as appropriate building blocks |
| 4-[(3-carbamoylphenyl)-methyl]-3-propyl-1H, 2H, 3H, 4H-cyclopenta[b]-indole-5-carboxylic acid | 400 MHz-DMSO d6: 12.76 (br s, 1H), 7.86 (br s, 1H), 7.65 (d, J = 7.6 Hz, 1H), 7.56 (d, J = 8.0 Hz, 1H) 7.49 (s, 1H), 7.36 (d, J = 7.6 Hz, 1H), 7.30 (s, 1H), 7.24(t, J = 7.6 Hz, 1H), 7.04(t, J = 7.6 Hz, 1h), 6.71 ( d, J = 7.6 Hz, 1H), 5.72 ( d, J = 16.4 Hz, 1H) 5.50 ( d, J = 16.4 Hz, 1H), 3.28-3.24(m, 1H), 2.87-2.64 (m, 3H), 2.22-2.17 (m, 1H), 1.58-1.52(m, 1H), 1.42-1.23(m, 3H), 0.79 (t, J = 6.8 Hz, 3H) | 376.18 | 377.1 | Compound was synthesized by method B using cyclopentantone and propyl-magnesium bromide as appropriate building blocks |
| 4-[(3-cyanophenyl)-methyl]-3-propyl-1H, 2H, 3H, 4H-cyclopenta[b]-dole-5-carboxylic acid | 400 MHz-DMSO d6 : 12.81(br s, 1H), 7.66 (d, J = 7.2 Hz, 1H), 7.59 (d, J = 8.0 Hz, 1H), 7.42(t, J = 8.0 Hz, 1H), 7.37(d, J - 7.2 Hz, 1H), 7.26 (s, 1H), 7.05 (t, J = 8.0 Hz, 1H), 5.70 ( d, J = 17.2 Hz, 1H), 5.53 (d, J = 17.2 Hz, 1H), 3.28-3.24(m, 1H), 2.87-2.64 (m, 3H), 2.22-2.17 (m, 1H), 1.58-1.52(m, 1H), 1.42-1.25(m, 3H), 0.79 (t, J = 6.8 Hz, 3H) | 358.17 | 359.1 | Compound was synthesized by method B using cyclopentantone and butyl-magnesium bromide as appropriate building blocks |
| 2-({7-butyl-5-[(3-carbamoylphenyl)-methyl]-5H,6H,7H,8H,9H,10H-cyclohepta[b]-indol-4-yl}formamido) acetic acid | 400 MHz-DMSO d6: 12.85(br s, 1H), 8.01 (br s, 1H), 7.62 (d, J = 8 Hz, 2H), 7.54 (d, J = 7.2 Hz, 1H), 7.51 ( s, 1H), 7.25-7.21 (m, 2H), 7.06 ( d, J = 6.0 Hz, 1H), 7.00 ( t, J = 8 Hz, 1H), 6.71(d, J = 7.6 Hz, 1H), 5.66 ( d, J = 17.6 Hz, 1H), 5.47 ( d, J = 17.6 Hz, 1H), 3.44-3.32 (m, 1H), 2.93-2.88 (m, 1H), 2.80(d, J = 15.2 Hz, 1H), 2.70-2.66(m, 1H), 2.51-2.42 (m, 2H), 1.92-1.85 (m, 2H), 1.55-1.47(m, 2H), 1.45-1.39(m, 1H), 1.12-0.95(m, 6H), 0.75 (t, J = 7 Hz, 3H) | 475.25 | 476.1 | Compound was synthesized by method C using 7-butyl-5-[(3-carbamoylphenyl) methyl]-5H,6H,7H,8H,9H, 10H-cyclohepta[b]-indole-4-carboxylic acid and alanine |
| 2-({7-butyl-5-[(3-cyanophenyl)-methyl]- | 400 MHz-DMSO d6: 12.60(br s, 1H), 8.71 (m, 1H), 7.64 (d, J = 8 Hz, 2H), 7.59 (d, J = 7.2 Hz, 1H), 7.43 ( t, J = 8 Hz, 1H), 7.21 ( s, 1H), 7.11-7.03 | 457.24 | 458.1 | Compound was synthesized by method C using 7-butyl-5-[(3- |

TABLE 1-continued

| IUPAC Name | 1H NMR | Exact Mass (g) | Observed [M + H]/Z | Synthetic Method |
|---|---|---|---|---|
| 5H,6H,7H,8H, 9H,10H-cyclohepta[b]-indol-4-yl}formamido) acetic acid | (m, 3H), 5.68 (d, J = 18.4 Hz, 1H), 5.49 (d, J = 18.4 Hz, 1H), 3.78-3.71 (m, 2H), 2.94-2.88 (m, 1H), 2.80-2.66(m, 2H), 2.47-2.42 (m, 2H), 1.92-1.85 (m, 2H), 1.53-1.47(m, 2H), 1.35-1.29(m, 1H), 1.13-0.95(m, 6H), 0.76 (t, J = 7.6 Hz, 3H) | | | cyanophenyl)-methyl]-5H,6H,7H,8H, 9H, 10H-cyclohepta[b]-indole-4-carboxylic acid and alanine |
| 7-butyl-5-[(3-carbamoylphenyl)-methyl]-N-(2-hydroxyethyl)-5H,6H,7H,8H, 9H,10H-cyclohepta[b]-indole-4-carboxamide | 400 MHz-DMSO d6: 12.85(br s, 1H), 8.22(t, J = 5.2 Hz, 1H), 7.87 (br s, 1H), 7.68 (d, J = 8.0 Hz, 2H), 7.54 (dd, J = 6.0, 2.8 Hz, 1H), 7.51 (s, 1H), 7.30-7.25 (m, 2H), 7.03-6.98 (m, 2H), 6.82(d, J = 8.0 Hz, 1H), 5.63 (d, J = 17.6 Hz, 1H), 5.47 (d, J = 17.6 Hz, 1H), 4.57(t, J = 6.0 Hz, 1H), 3.26-3.23 (m, 2H), 3.12(m, 2H), 2.93-2.88 (m, 1H), 2.78 (d, J = 15.2 Hz, 1H), 2.70-2.66(m, 1H), 2.51-2.42 (m, 2H), 1.92-1.85 (m, 2H), 1.53-1.47(m, 2H), 1.43-1.33(m, 1H), 1.12-0.95(m, 6H), 0.75 (t, J = 7 Hz, 3H) | 461.27 | 462.2 | Compound was synthesized by method C using 7-butyl-5-[(3-carbamoylphenyl) methyl]-5H,6H,7H,8H,9H, 10H-cyclohepta[b]-indole-4-carboxylic acid and 2-amine-1-ol |
| 7-butyl-5-[(3-cyanophenyl)-methyl]-N-(2-hydroxyethyl)-5H,6H,7H,8H, 9H,10H-cyclohepta[b]-indol-4-carboxamide | 400 MHz-DMSO d6: 8.31-8.27(m, 1H), 7.67 (d, J = 7.2 Hz, 2H), 7.60-7.56 (m, 1H), 7.45 (t, J = 8.p0 Hz, 1H), 7.17-7.07 (m, 2H), 7.05-7.02 (m, 2H), 5.63 (d, J = 18.0 Hz, 1H), 5.50 (d, J = 18.0 Hz, 1H), 4.57(t, J = 6.0 Hz, 1H), 3.26-3.20 (m, 2H), 3.14-3.06 (m, 2H), 2.92-2.86 (m, 1H), 2.77-2.69 (m, 1H), 2.47-2.42 (m, 2H), 1.93-1.85 (m, 2H), 1.53-1.47(m, 2H), 1.35-1.23(m, 1H), 1.12-0.95(m, 6H), 0.74 (t, J = 7 Hz, 3H) | 443.26 | 444.1 | Compound was synthesized by method C using 7-butyl-5-[(3-cyanomoylphenyl) methyl]-5H,6H,7H,8H,9H, 10H-cyclohepta[b]-indole-4-carboxylic acid and 2-amine-1-ol |
| 7-butyl-5-[(3-fluorophenyl)-methyl]-5H,6H,7H,8H, 9H,10H-cyclohepta[b]-indole-4-carboxylic acid | 400 MHz-DMSO d6: 12.85(br s, 1H), 7.65 (d, J = 8 Hz, 1H), 7.38 (d, J = 8 Hz, 1H), 7.25 (m, 1H), 7.04-6.96 (m, 2H), 6.58-6.64(m, 2H), 5.80 (d, J = 16.8 Hz, 1H), 5.60( d, J = 17 Hz, 1H), 2.93-2.87 (m, 1H), 2.83( d, J = 16 Hz, 1H), 2.72-2.66(m, 1H), 2.47 (m, 1H), 1.92-1.84 (m, 2H), 1.58-1.48(m, 2H), 1.45-1.36(m, 1H), 1.11-0.95(m, 6H), 0.77 (t, | 393.21 | 394.1 | Compound was synthesized by method A using 3-butyl-1-cycloheptanone and 3-methyl-1-benzyl bromide as appropriate building blocks |
| 7-butyl-5-[(3-carboxyphenyl) methyl]-5H,6H,7H,8H, 9H,10H-cyclohepta[b]-indole-4-carboxylic acid | 400 MHz-DMSO d6: 12.85(br s, 1H), 7.75 (d, J = 8 Hz, 1H), 7.65 (d, J = 8 Hz, 1H), 7.47(s, 1H), 7.40-7.330(m, 2H), 7.05(t, J = 7.2 Hz, 1H), 6.97(d, J = 7.2 Hz, 1H), 5.82 (d, J = 16.8 Hz, 1H), 5.61 (d, J = 17 Hz, 1H), 2.93-2.88 (m, 1H), 2.81( d, J = 16 Hz, 1H), 2.72-2.66(m, 1H), 2.47 (m, 1H), 1.92-1.84 (m, 2H), 1.52-1.46(m, 2H), 1.36(br s, 1H), 1.12-0.93(m, 6H), 0.72 (t, J = 0 6.8 Hz, 3H) | 419.21 | 420.1 | Compound was synthesized by method A using 3-butyl-1-cycloheptanone and 3-cyano-1-benzyl bromide as appropriate building blocks |

Representative HPLC methods that may be used include the following:

Method A
 Column: Kinetex EVO C18 (50 mm×4.6 mm, 5 um)
 Mobile Phase: B1: 0.1% FA IN WATER A1: 0.1% FA IN ACN
 Gradient: Time (min)/% A1: 0/2, 0.4/2, 2.7/98, 3.40/98, 3.41/2, 3.5/2
 Column Flow Rate: 2.0 ml/min
 Column Temperature: 45° C.
Method B
 Column: ACQUITY UPLC BEH C18 (50 mm×2.1 mm, 1.7 um)
 Mobile Phase: B1: 0.1% FA IN WATER A1: 0.1% FA IN ACN
 Gradient: Time (min)/% A1: 0/2, 0.4/2, 2.8/98, 3.4/98, 3.41/2, 3.5/2
 Column Flow Rate: 0.6 ml/min
 Column Temperature: 60° C.
Method C
 Column: ACQUITY UPLC BEH C18 (50 mm×2.1 mm, 1.7 um)
 Mobile Phase: B1: 0.1% FA IN WATER A1: 0.1% FA IN ACN
 Gradient: Time (min)/% A1: 0/2, 0.3/2, 2.3/98, 2.8/98, 2.81/2, 3.0/2
 Column Flow Rate: 0.8 ml/min
 Column Temperature: 60° C.
Method D
 Column: X-BRIDGE C18 (4.6×150 mm) 5 μm
 Mobile Phase: A:10 mM Ammonium acetate (aqs), B: Acetonitrile
 Gradient Time % B: Diluent 0/10, 1/10, 12/95, 15/98,20/98, 20.01/10
 Column Temp Flow Rate: Ambient : 1 ml/min:(ACN: WATER)

Method E
  Column: ACQUITY UPLC BEH C18 (50 mm×2.1 mm, 1.7 um)
  Mobile Phase: B1: 0.1% FA IN WATER A1: 0.1% FA IN ACNACN:
  Gradient: Time (min)/% A1: 0/2, 0.2/2, 5.0/98, 5.8/98, 5.81/2.0, 6.00/2.0
  Column Flow Rate: 0.8 ml/min
  Column Temperature: 60° C.

Method F
  Mobile Phase A: 0.1% FA in Water
  Mobile Phase B: 0.1% FA in ACN
  Gradient % of B:
  0/5, 0.3/5, 1.5/60, 2/98, 4/98, 5/5
  Flow: 0.6 ml/min
  Column: BEH C18, 2.1*50 mm, 1.7 um, Table 2 below correlates the HPLC methods used with the IUPAC name:

TABLE 2

| IUPAC Name | Mol. Weight | HPLC method/rt |
|---|---|---|
| 7-butyl-5-[(3-cyanophenyl)methyl]-N-(2-hydroxyethyl)-5H,6H,7H,8H,9H,10H-cyclohepta[b]indole-4-carboxamide | 443.59 | Method B/2.51 |
| 2-({7-butyl-5-[(3-cyanophenyl)methyl]-5H,6H,7H,8H,9H,10H-cyclohepta[b]indol-4-yl}formamido)acetic acid | 457.57 | Method B/2.54 |
| 2-({7-butyl-5-[(3-carbamoylphenyl)methyl]-5H,6H,7H,8H,9H,10H-cyclohepta[b]indol-4-yl}formamido)acetic acid | 475.59 | Method B/2.296 |
| 4-[3-cyanophenyl)methyl]-3-propyl-1H,2H,3H,4H-cyclopenta[b]indole-5-carboxylic acid | 358.44 | Method B/2.454 |
| 4-[(3-carbamoylphenyl)methyl]-3-propyl-1H,2H,3H,4H-cyclopenta[b]indole-5-carboxylic acid | 376.46 | Method B/2.220 |
| 9-[(3-cyanophenyl)methyl]-3-pentyl-2,3,4,9-tetrahydro-1H-carbazole-8-carboxylic acid | 400.52 | Method B/2.755 |
| 9-[(3-carbamoylphenyl)methyl]-3-pentyl-2,3,4,9-tetrahydro-1H-carbazole-8-carboxylic acid | 418.54 | Method B/2.54 |
| 9-3[(3-cyanophenyl)methyl]-4-pentyl-2,3,4,9-tetrahydro-1H-carbazole-8-carboxylic acid | 400.52 | Method B/2.878 |
| 9-[(3-carbamoylphenyl)methyl]-4-pentyl-2,3,4,9-tetrahydro-1H-carbazole-8-carboxylic acid | 418.54 | Method B/2.64 |
| 3-butyl-9-[(3-cyanophenyl)methyl]-2,3,4,9-tetrahydro-1H-carbazole-8-carboxylic acid | 386.50 | Method B/2.83 |
| 3-butyl-9-[(3-carbamoylphenyl)methyl]-2,3,4,9-tetrahydro-1H-carbazole-8-carboxylic acid | 404.51 | Method B/2.65 |
| 4-butyl-9-[3-cyanophenyl)methyl]-2,3,4,9-tetrahydro-1H-carbazole-8-carboxylic acid | 386.50 | Method C/2.79 |
| 4-butyl-9-[(3-carbamoylphenyl)methyl]-2,3,4,9-tetrahydro-1H-carbazole-8-carboxylic acid | 404.51 | Method C/2.53 |
| 9-[(3-cyanophenyl)methyl]-3-propyl-2,3,4,9-tetrahydro-1H-carbazole-8-carboxylic acid | 372.47 | Method C/2.27 |
| 9-[(3-carbamoylphenyl)methyl]-3-propyl-2,3,4,9-tetrahydro-1H-carbazole-8-carboxylic acid | 390.48 | Method B/2.35 |
| 9-[(3-carbamoylphenyl)methyl]-4-propyl-2,3,4,9-tetrahydro-1H-carbazole-8-carboxylic acid | 390.48 | Method B/2.29 |
| 9-[(3-cyanophenyl)methyl]-3-ethyl-2,3,4,9-tetrahydro-1H-carbazole-8-carboxylic acid | 358.44 | Method B/2.47 |
| 5-[(3-cyanophenyl)methyl]-7-ethyl-5H,6H,7H 8H,9H,10H-cyclohepta[b]indole-4-carboxylic acid | 372.47 | Method B/2.66 |
| 5-[(3-carbamoylphenyl)methyl]-7-ethyl-5H,6H,7H,8H,9H,10H-cyclohepta[b]indole-4-carboxylic acid | 390.48 | Method B/2.37 |
| 9-[(3-carboxyphenyl)methyl]-2-ethyl-2,3,4,9-tetrahydro-1H-carbazole-8-carboxylic acid | 377.44 | Method B/2.496 |
| 9-[(3-carbamoylphenyl)methyl]-2-ethyl-2,3,4,9-tetrahydro-1H-carbazole-8-carboxylic acid | 376.46 | Method B/2.38 |
| 4-[(3-cyanophenyl)methyl]-2-pentyl-1H,2H,3H,4H-cyclopenta[b]indole-5-carboxylic acid | 386.50 | Method B/2.69 |
| 4-[(3-carbamoylphenyl)methyl]-2-pentyl-1H,2H,3H,4H-cyclopenta[b]indole-5-carboxylic acid | 404.51 | Method B/2.48 |
| 5-[(3-cyanophenyl)methyl]-10-pentyl-5H,6H,7H,8H,9H,10H-cyclohepta[b]indole-4-carboxylic acid | 414.55 | Method B/2.746 |
| 5-[(3-carbamoylphenyl)methyl]-10-pentyl-5H,6H,7H,8H,9H,10H-cyclohepta[b]indole-4-carboxylic acid | 432.56 | Method B/2.54 |
| 10-butyl-5-[(3-cyanophenyl)methyl]-5H,6H,7H,8H,9H,10H-cyclohepta[b]indole-4-carboxylic acid | 400.52 | Method B/2.663 |
| 10-butyl-5-[(3-carbamoylphenyl)methyl]-5H,6H,7H,8H,9H,10H-cyclohepta[b]indole-4-carboxylic acid | 418.54 | Method B/2.441 |
| 9-[(3-carbamoylphenyl)methyl]-3-ethyl-2,3,4,9-tetrahydro-1H-carbazole-8-carboxylic acid | 376.46 | Method B/2.23 |
| 5-[(3-cyanophenyl)methyl]-10-propyl-5H,6H,7H,8H,9H,10H-cyclohepta[b]indole-4-carboxylic acid | 386.50 | Method B/2.58 |
| 5-[(3-carbamoylphenyl)methyl]-10-propyl-5H,6H,7H,8H,9H,10H-cyclohepta[b]indole-4-carboxylic acid | 404.51 | Method B/2.34 |
| 5-[(3-cyanophenyl)methyl]-10-ethyl-5H,6H,7H,8H,9H,10H-cyclohepta[b]indole-4-carboxylic acid | 372.47 | Method B/2.64 |

TABLE 2-continued

| IUPAC Name | Mol. Weight | HPLC method/rt |
|---|---|---|
| 5-[(3-carbamoylphenyl)methyl]-10-ethyl-5H,6H,7H, 8H,9H,10H-cyclohepta[b]indole-4-carboxylic acid | 390.48 | Method B/2.35 |
| 2-butyl-4-[(3-cyanophenyl)methyl]-1H,2H,3H,4H-cyclopenta[b]indole-5-carboxylic acid | 372.47 | Method B/2.77 |
| 2-butyl-4-[(3-carbamoylphenyl)methyl]-1H,2H,3H,4H-cyclopenta[b]indole-5-carboxylic acid | 390.48 | Method B/2.51 |
| 3-butyl-4-[(3-cyanophenyl)methyl]-1H,2H,3H,4H-cyclopenta[b]indole-5-carboxylic acid | 372.47 | Method B/2.54 |
| 3-butyl-4-[(3-carbamoylphenyl)methyl]-1H,2H,3H,4H-cyclopenta[b]indole-5-carboxylic acid | 390.48 | Method B/2.31 |
| 9-[(3-carbamoylphenyl)methyl]-4-ethyl-2,3,4,9-tetrahydro-1H-carbazole-8-carboxylic acid | 376.46 | Method A/2.30 |
| 9-[(3-carbamoylphenyl)methyl]-1-propoxy-2,3,4,9-tetrahydro-1H-carbazole-8-carboxylic acid | 406.48 | Method B/2.18 |
| 9-[(3-carboxyphenyl)methyl]-1-ethyl-2,3,4,9-tetrahydro-1H-carbazole-8-carboxylic acid | 377.44 | Method B/2.34 |
| 9-[(3-carbamoylphenyl)methyl]-1-ethyl-2,3,4,9-tetrahydro-1H-carbazole-8-carboxylic acid | 376.46 | Method B/2.24 |
| 6-butyl-5-[(3-carbamoylphenyl)methyl]-5H,6H,7H, 8H,9H,10H-cyclohepta[b]indole-4-carboxylic acid | 418.54 | Method B/2.50 |
| 1-butyl-9-[(3-cyanophenyl)methyl]-2,3,4,9-tetrahydro-1H-carbazole-8-carboxylic acid | 386.50 | Method B/2.63 |
| 9-[(3-cyanophenyl)methyl]-1-(pentyloxy)-2,3,4,9-tetrahydro-1H-carbazole-8-carboxylic acid | 416.52 | Method B/2.64 |
| 9-[(3-carbamoylphenyl)methyl]-1-(pentyloxy)-2,3,4,9-tetrahydro-1H-carbazole-8-carboxylic acid | 434.54 | Method B/2.33 |
| 1-butyl-9-[(3-carbamoylphenyl)methyl]-2,3,4,9-tetrahydro-1H-carbazole-8-carboxylic acid | 404.51 | Method B/2.40 |
| 9-[(3-cyanophenyl)methyl]-2-pentyl-2,3,4,9-tetrahydro-1H-carbazole-8-carboxylic acid | 400.52 | Method A/2.69 |
| 9-[(3-carbamoylphenyl)methyl]-2-pentyl-2,3,4,9-tetrahydro-1H-carbazole-8-carboxylic acid | 418.54 | Method A/2.42 |
| 2-butyl-9-[(3-carbamoylphenyl)methyl]-2,3,4,9-tetrahydro-1H-carbazole-8-carboxylic acid | 404.51 | Method D/9.11 |
| 9-[(3-cyanophenyl)methyl]-2-propyl-2,3,4,9-tetrahydro-1H-carbazole-8-carboxylic acid | 372.47 | Method A/2.50 |
| 9-[(3-carbamoylphenyl)methyl]-2-propyl-2,3,4,9-tetrahydro-1H-carbazole-8-carboxylic acid | 390.48 | Method A/2.20 |
| 9-[(2-fluorophenyl)methyl]-2-hexyl-2,3,4,9-tetrahydro-1H-carbazole-8-carboxylic acid | 407.53 | Method E/3.343 |
| 2-hexyl-9-[(2-methylphenyl)methyl]-2,3,4,9-tetrahydro-1H-carbazole-8-carboxylic acid | 403.57 | Method E/3.513 |
| 9-[(2-cyanophenyl)methyl]-2-hexyl-2,3,4,9-tetrahydro-1H-carbazole-8-carboxylic acid | 414.55 | Method E/3.133 |
| 9-[(4-cyanophenyl)methyl]-2-hexyl-2,3,4,9-tetrahydro-1H-carbazole-8-carboxylic acid | 414.55 | Method B/3.066 |
| 2-hexyl-9-[(4-methylphenyl)methyl]-2,3,4,9-tetrahydro-1H-carbazole-8-carboxylic acid | 403.57 | Method E/3.441 |
| 9-[(3-carboxyphenyl)methyl]-2-hexyl-2,3,4,9-tetrahydro-1H-carbazole-8-carboxylic acid | 433.55 | Method B/2.908 |
| 9-[(3-carboxyphenyl)methyl]-2-hexyl-2,3,4,9-tetrahydro-1H-carbazole-8-carboxylic acid | 433.55 | Method B/2.77 |
| 9-[(3-cyanophenyl)methyl]-2-hexyl-2,3,4,9-tetrahydro-1H-carbazole-8-carboxylic acid | 414.55 | Method B/2.91 |
| 9-[(3-carbamoylphenyl)methyl]-2-hexyl-2,3,4,9-tetrahydro-1H-carbazole-8-carboxylic acid | 432.56 | Method B/2.70 |
| 5-[(4-flurophenyl)methyl]-7-hexyl-5H,6H,7H, 8H,9H,10H-cyclohepta[b]indole-4-carboxylic acid | 421.56 | Method F/3.82 |
| 5-[(2-fluorophenyl)methyl]-7-hexyl-5H,6H,7H,8H, 9H,10H-cyclohepta[b]indole-4-carboxylic acid | 421.56 | Method F/3.86 |
| 7-hexyl-5-[(2-methylphenyl)methyl]-5H,6H,7H,8H, 9H,10H-cyclohepta[b]indole-4-carboxylic acid | 417.59 | Method B/3.685 |
| 5-[(4-cyanophenyl)methyl]-7-hexyl-5H,6H,7H,8H, 9H,10H-cyclohepta[b]indole-4-carboxylic acid | 428.58 | Method F/3.70 |
| 7-hexyl-5-[(4-methylphenyl)methyl]-5H,6H,7H,8H,9H, 10H-cyclohepta[b]indole-4-carboxylic acid | 417.59 | Method F/3.93 |
| 5-[3-chlorophenyl)methyl]-7-hexyl-5H,6H,7H,9H, 10H-cyclohepta[b]indole-4-carboxylic acid | 438.01 | Method B/3.669 |
| 7-hexyl-5-[(3-methoxyphenyl)methyl]-5H,6H,7H,8H, 9H,10H-cyclohepta[b]indole-4-carboxylic acid | 433.59 | Method B/3.359 |
| 7-hexyl-5-[(3-methylphenyl)methyl]-5H,6H,7H,8H, 9H,10H-cyclohepta[b]indole-4-carboxylic acid | 417.59 | Method F/3.92 |
| 5-[(3-fluorophenyl)methyl]-7-hexyl-5H,6H,7H,8H, 9H,10H-cyclohepta[b]indole-4-carboxylic acid | 421.56 | Method B/3.448 |
| 5-[(3-cyanophenyl)methyl]-7-hexyl-5H,6H,7H,8H, 9H,10H-cyclohepta[b]indole-4-carboxylic acid | 428.58 | Method B/2.83 |
| 5-[(3-carbamoylphenyl)methyl]-7-hexyl-5H,6H,7H,8H, 9H,10H-cyclohepta[b]indole-4-carboxylic acid | 446.59 | Method B/2.72 |

TABLE 2-continued

| IUPAC Name | Mol. Weight | HPLC method/rt |
|---|---|---|
| 9-[(3-cyanophenyl)methyl]-2,3,4,9-tetrahydro-1H-carbazole-8-carboxylic acid | 330.39 | Method C/1.87 |
| 9-[(3-carbamoylphenyl)methyl]-2,3,4,9-tetrahydro-1H-carbazole-8-carboxylic acid | 348.40 | Method C/1.65 |
| 5-[3-cyanophenyl)methyl]-7-(2-phenylethyl)-5H,6H,7H,8H,9H,10H-cyclohepta[b]indol-4-carboxylic acid | 448.57 | Method C/2.16 |
| 5-[(3-carbamoylphenyl)methyl]-7-(2-phenylethyl)-5H,6H,7H,8H,9H,10H-cyclohepta[b]indole-4-carboxylic aid | 466.58 | Method C/1.98 |
| 5-[(3-cyanophenyl)methyl]-7-pentyl-5H,6H,7H,8H,9H,10H-cyclohepta[b]indole-4-carboxylic acid | 414.55 | Method B/2.60 |
| 5-[(3-carbamoylphenyl)methyl]-7-pentyl-5H,6H,7H,8H,9H,10H-cyclohepta[b]indole-4-carboxylic acid | 432.56 | Method B/2.42 |
| 7-butyl-5-[(2-fluorophenyl)methyl]-5H,6H,7H,8H,9H 10H-cyclohepta[b]indole-4-carboxylic acid | 393.50 | Method B/3.010 |
| 7-butyl-5-[(2-methylphenyl)methyl]-5H,6H,7H,8H,9H,10H-cyclohepta[b]indole-4-carboxylic acid | 389.54 | Method B/3.049 |
| 7-butyl-5-[(2-cyanophenyl)methyl]-5H,6H,7H,8H,9H,10H-cyclohepta[b]indole-4-carboxylic acid | 400.52 | Method F/3.55 |
| 7-butyl-5-[(4-methylphenyl)methyl]-5H,6H,7H,8H,9H,10H-cyclohepta[b]indole-4-carboxylic acid | 389.54 | Meethod B/3.058 |
| 7-butyl-5-[2-carbamoylphenyl)methyl]-5H,6H,7H,8H,9H,10H-cyclohepta[b]indole-4-carboxylic acid | 418.54 | Method B/2.729 |
| 7-butyl-5-[(4-carbamoylphenyl)methyl]-5H,6H,7H,8H,9H,10H-cyclohepta[b]indole-4-carboxylic acid | 418.54 | Method B/2.594 |
| 7-butyl-5-[(3-carboxyphenyl)methyl]-5H,6H,7H,8H,9H,10H-cyclohepta[b]indole-4-carboxylic acid | 419.52 | Method B/2.726 |
| 7-butyl-5-[(2-methoxypyridin-4-yl)methyl]-5H,6H,7H,8H,9H,10H-cyclohepta[b]indole-4-carboxylic acid | 406.53 | Method B/2.8 |
| 7-butyl-5-[(3-hydroxyphenyl)methyl]-5H,6H,7H,8H,9H,10H-cyclohepta[b]indole-4-carboxylic acid | 391.51 | Method B/3.38 |
| 7-butyl-5-[(3-chlorophenyl)methyl]-5H,6H,7H,8H,9H,10H-cyclohepta[b]indole-4-carboxylic acid | 409.95 | Method B/3.037 |
| 7-butyl-5-[(3-methoxyphenyl)methyl]-5H,6H,7H,8H,9H,10H-cyclohepta[b]indole-4-carboxylic acid | 405.54 | Method B/2.967 |
| 7-butyl-5-[(3-methylphenyl)methyl]-5H,6H,7H,8H,9H,10H-cyclohepta[b]indole-4-carboxylic acid | 389.54 | Method B/3.057 |
| 7-butyl-5-[(pyridin-3-yl)methyl]-5H,6H,7H,8H,9H,10H-cyclohepta[b]indole-4-carboxylic acid | 376.50 | Method B/3.16 |
| 7-butyl-5-[(3-fluorophenyl)methyl]-5H,6H,7H,8H,9H,10H-cyclohepta[b]indole-4-carboxylic acid | 393.50 | Method E/2.723 |
| 7-butyl-5-[(3-cyanophenyl)methyl]-5H,6H,7H,8H,9H,10H-cyclohepta[b]indole-4-carboxylic acid | 400.52 | Method B/2.68 |
| 7-butyl-5-[(3-carbamoylphenyl)methyl]-5H,6H,7H,8H,9H,10H-cyclohepta[b]indole-4-carboxylic acid | 418.54 | Method B/2.45 |
| 5-[(3-carbamoylphenyl)methyl]-7-propyl-5H,6H,7H,8H,9H,10H-cyclohepta[b]indole-4-carboxylic acid | 404.51 | Method A/2.23 |

Activity of compounds on adipocyte glucose consumption was tested in differentiated 3T3-L1 mouse adipocyte cells. 3T3-L1 preadipocytes (ATCC) were routinely cultured in a growth medium composed of DMEM high-glucose (Sigma), 1000 FBS (Gibco), 10 U/ml penicillin and 10 µg/ml streptomycin (P/S; Gibco). To induce adipogenic differentiation, a confluent layer of 3T3-L1 cells were incubated with the growth medium containing 2 µM rosiglitazone, 1 µM dexamethasone, 500 µM IBMX, and 1 µg/ml insulin (Sigma). Forty-eight (48) hours later (on day 2) and on days 4 and 6, medium of the cells was replaced with fresh medium containing 1 µg/ml insulin. On days 8 and 10, the medium was refreshed with regular growth medium and addition of insulin was omitted. On day 11 or 12, medium of the cells were replaced with fresh medium containing either the indicated compounds (10 µM) or the vehicle in which the compounds were dissolved (DMSO). The final concentration of DMSO was 0.1% (v/v). Growth medium containing 0.1% DMSO was incubated in culture wells containing no cells and used as control. Twenty-two to 24 hours later, medium was harvested and subjected to centrifugation at 10,000 g for 5 min. Glucose concentration in the supernatants was determined using a colorimetric assay (Glucose Assay Kit I, Eton Biosciences). Glucose consumption in compound and vehicle treated cells was measured as loss of glucose from the culture medium and represented as mean fold change (compound/DMSO)±standard deviation (SD).

Activity of compounds with FABP4 was profiled using a Terbium (Tb) based time resolved fluorescence energy transfer (TR-FRET) assay. The assay measures the compound mediated displacement of the fluorescent fatty acid BODIPY FL C12 (Thermo Fisher; catalog number D3822) from His6 tagged human recombinant FABP4 (His6-FABP4; Cayman Chemicals, catalog number 10009549) via recording the energy transfer from TB donor molecule on anti-His6-tag antibody to acceptor BODIPY moiety. Briefly, compounds were prepared at a concentration of 0.362 mM and 0.0362 mM, and BODIPY FL C12 was prepared at 4.2 µM, in DMSO. 1.2 µL of each compound or DMSO (vehicle control) and 1.2 µL of BODIPY FL C12 were added into the wells of a 384-well black polypropylene plate. His6-FABP4 and Tb anti-His6 antibody were prepared in the assay buffer (25 mM Tris/HCl, pH 7.4, 0.4 mg/ml y-globulins, 0.010% NP-40, 1 mM DTT) at a concentration of 83 nM and 49.6 nM, respectively. The protein and antibody solutions were then mixed at a ratio of 34:7 (v/v) and incubated on ice for 30 minutes. The assay was initiated by adding 41 µL of the resulting protein/antibody solution into the wells containing the compounds and BODIPY FL C12. The plate was centrifuged and incubated at room temperature for 10 min. The TR-FRET signals were recorded using an EnVision Multi-label plate reader (PerkinElmer; TB excitation 320 nm, BODIPY FL C12 emission 520 nm; TB emission 615 nm). Relative fluorescence ratio (520 nm*10,000/615 nm) were used to calculate the compound mediated inhibition of BODIPY C12 FL fatty acid binding to FABP4. The compounds were tested in triplicates and the results were displayed as mean percent inhibition (compound*100/DMSO) ±standard deviation (SD). Glucose consumption and FABP4 inhibition is shown below in Table 3 below.

TABLE 3

| IUPAC Name | Glucose consumption (fold change) Mean | Standard Deviation | FABP4 inhibition (%) at 10 µM Mean | Standard Deviation | FABP4 inhibition (%) at 1 µM Mean | Standard Deviation |
|---|---|---|---|---|---|---|
| 5-[(3-cyanophenyl)methyl]-2-fluoro-7-hexyl-5H,6H,7H,8H,9H,10H-cyclohepta[b]indole-4-carboxylic acid | 1.33 | 0.16 | 93.93 | 5.33 | 87.33 | 2.21 |
| 5-[(6-cyanopyridin-2-yl)methyl]-7-hexyl-5H,6H,7H,8H,9H,10H-cyclohepta[b]indole-4-carboxylic acid | 1.28 | 0.05 | 88.08 | 2.75 | 93.45 | 3.71 |
| 5-[(6-carbamoylpyridin-2-yl)methyl]-7-hexyl-5H,6H,7H,8H,9H,10H-cyclohepta[b]indole-4-carboxylic acid | 1.23 | 0.07 | 95.20 | 1.10 | 93.97 | 0.72 |
| 6-({4-carboxy-7-hexyl-5H,6H,7H,8H,9H,10H-cyclohepta[b]indol-5-yl]methyl)pyridine-2-carboxylic acid | 0.96 | 0.06 | 96.52 | 4.41 | 91.60 | 2.01 |
| 5-[(3-cyano-2-fluorophenyl)methyl]-7-hexyl-5H,6H,7H,8H,9H,10H-cyclohepta[b]indole-4-carboxylic acid | 1.36 | 0.11 | 95.46 | 2.28 | 87.86 | 2.41 |
| 5-[(1,3-benzoxazol-6-yl)methyl]-7-hexyl-5H,6H,7H,8H,9H,10H-cyclohepta[b]indole-4-carboxylic acid | 1.17 | 0.00 | 94.89 | 6.25 | 101.45 | 5.49 |

TABLE 3-continued

| IUPAC Name | Glucose consumption (fold change) Mean | Standard Deviation | FABP4 inhibition (%) at 10 μM Mean | Standard Deviation | FABP4 inhibition (%) at 1 μM Mean | Standard Deviation |
| --- | --- | --- | --- | --- | --- | --- |
| 5-[(1,3-benzoxazol-5-ylmethyl]-7-hexyl-5H,6H,7H,8H,9H,10H-cyclohepta[b]indole-4-carboxylic acid | 0.87 | 0.05 | 88.48 | 3.59 | 88.05 | 4.24 |
| 5-[(6-fluoropyridin-2-yl)methyl]-7-hexyl-5H,6H,7H,8H,9H,10H-cyclohepta[b]indole-4-carboxylic acid | 1.25 | 0.07 | 91.85 | 6.14 | 86.45 | 3.56 |
| 5-[(2-fluoropyridin-4-yl)methyl]-7-hexyl-5H,6H,7H,8H,9H,10H-cyclohepta[b]indole-4-carboxylic acid | N.D. | | 90.36 | 6.43 | 92.85 | 2.17 |
| 7-hexyl-5-{[6-(trifluoromethyl)pyridin-2-yl]methyl}-5H,6H,7H,8H,9H,10H-cyclohepta[b]indole-4-carboxylic acid | N.D. | | 79.79 | 5.72 | 79.67 | 6.79 |
| 7-hexyl-5-{[2-(trifluoromethyl)pyridin-4-yl]methyl}-5H,6H,7H,8H,9H,10H-cyclohepta[b]indole-4-carboxylic acid | N.D. | | 94.69 | 4.08 | 87.58 | 3.36 |
| 5-[(5-cyanopyridin-3-yl)methyl]-7-hexyl-5H,6H,7H,8H,9H,10H-cyclohepta[b]indole-4-carboxylic acid | 1.06 | 0.04 | 91.85 | 5.52 | 90.51 | 1.79 |
| 5-[(5-cyanothiophen-2-yl)methyl]-7-hexyl-5H,6H,7H,8H,9H,10H- | 1.05 | 0.03 | 87.32 | 3.51 | 86.60 | 1.60 |

TABLE 3-continued

| IUPAC Name | Glucose consumption (fold change) Mean | Standard Deviation | FABP4 inhibition (%) at 10 μM Mean | Standard Deviation | FABP4 inhibition (%) at 1 μM Mean | Standard Deviation |
|---|---|---|---|---|---|---|
| cyclohepta[b]indole-4-carboxylic acid | | | | | | |
| 5-[(5-cyanothiophen-2-yl)methyl]-7-hexyl-5H,6H,7H,8H,9H,10H-cyclohepta[b]indole-4-carboxylic acid | N.D. | | 89.42 | 3.25 | 83.31 | 4.04 |
| 5-[(5-cyanofuran-2-yl)methyl]-7-hexyl-5H,6H,7H,8H,9H,10H-cyclohepta[b]indole-4-carboxylic acid | 1.29 | 0.10 | 90.01 | 4.54 | 81.35 | 3.96 |
| 5-[(3,5-dimethyl-1,2-oxazol-4-yl)methyl]-7-hexyl-5H,6H,7H,8H,9H,10H-cyclohepta[b]indole-4-carboxylic acid | 0.95 | 0.00 | 95.64 | 4.70 | 79.75 | 2.98 |
| 5-(3-cyanobenzoyl)-7-hexyl-5H,6H,7H,8H,9H,10H-cyclohepta[b]indole-4-carboxylic acid | N.D. | | 88.54 | 2.91 | 87.12 | 3.59 |
| 5-[(1,3-benzoxazol-7-yl)methyl]-7-hexyl-5H,6H,7H,8H,9H,10H-cyclohepta[b]indole-4-carboxylic acid | N.D. | | 95.32 | 4.32 | 92.05 | 8.03 |
| 5-[(5-cyanothiophen-3-yl)methyl]-7-hexyl-5H,6H,7H,8 9H,10H-H,cyclohepta[b]indole-4-carboxylic acid | 1.20 | 0.00 | N.D. | | N.D. | |
| 5-[(3-carbamoyl-phenyl)methyl]-7-propyl-5H,6H,7H,8H, | 1.06 | 0.05 | 91.42 | 3.55 | 85.14 | 1.91 |

TABLE 3-continued

| IUPAC Name | Glucose consumption (fold change) Mean | Standard Deviation | FABP4 inhibition (%) at 10 µM Mean | Standard Deviation | FABP4 inhibition (%) at 1 µM Mean | Standard Deviation |
|---|---|---|---|---|---|---|
| 9H,10H-cyclohepta[b]indole-4-carboxylic acid | | | | | | |
| 7-butyl-5-[(3-carbamoyl-pheny)methyl]-5H,6H,7H,8H,9H,10H-cyclohepta[b]indole-4-carboxylic acid | 1.12 | 0.08 | 116.71 | 37.23 | 89.41 | 2.63 |
| 7-butyl-5-[(3-cyanophenyl)methyl]-5H,6H,7H,8H,9H,10H-cyclohepta[b]indole-4-carboxylic acid | 1.29 | 0.02 | 112.30 | 41.26 | 73.46 | 6.37 |
| 7-butyl-5-[(pyridin-3-yl)methyl]-5H,6H,7H,8H,9H,10H-cyclohepta[b]indole-4-carboxylic acid | 1.21 | 0.00 | 83.81 | 1.55 | 71.63 | 5.54 |
| 7-butyl-5-[(3-methylphenyl)methyl]-5H,6H,7H,8H,9H,10H-cyclohepta[b]indole-4-carboxylic acid | 1.32 | 0.05 | 91.05 | 1.76 | 94.75 | 7.89 |
| 7-butyl-5-[(3-methoxyphenyl)methyl]-5H,6H,7H,8H,9H,10H-cyclohepta[b]indole-4-carboxylic acid | 1.23 | 0.02 | 86.49 | 3.46 | 91.65 | 4.14 |
| 7-butyl-5-[(3-chlorophenyl)methyl]-5H,6H,7H,8H,9H,10H-cyclohepta[b]indole-4-carboxylic acid | 1.18 | 0.04 | 83.05 | 5.99 | 84.25 | 4.37 |
| 7-butyl-5-[(3-hydroxyphenyl)methyl]-5H,6H,7H,8H,9H,10H-cyclohepta[b]indole-4-carboxylic acid | 1.14 | 0.08 | 96.10 | 6.35 | 98.73 | 1.50 |

TABLE 3-continued

| IUPAC Name | Glucose consumption (fold change) Mean | Standard Deviation | FABP4 inhibition (%) at 10 μM Mean | Standard Deviation | FABP4 inhibition (%) at 1 μM Mean | Standard Deviation |
|---|---|---|---|---|---|---|
| 7-butyl-5-[(2-methoxypyridin-4-yl)methyl]-5H,6H,7H,8H,9H,10H-cyclohepta[b]indole-4-carboxylic acid | N.D. | | 88.17 | 2.64 | 83.40 | 3.63 |
| 7-butyl-5-[(4-carbamoylphenyl)methyl]-5H,6H,7H,8H,9H,10H-cyclohepta[b]indole-4-carboxylic acid | 1.13 | 0.09 | 95.47 | 2.56 | 92.59 | 3.07 |
| 7-butyl-5-[(2-carbamoylphenyl)methyl]-5H,6H,7H,8H,9H,10H-cyclohepta[b]indole-4-carboxylic acid | 1.11 | 0.07 | 94.50 | 4.71 | 71.33 | 6.27 |
| 7-butyl-5-[(4-methylphenyl)methyl]-5H,6H,7H,8H,9H,10H-cyclohepta[b]indole-4-carboxylic acid | 1.27 | 0.02 | 92.42 | 2.91 | 106.31 | 4.76 |
| 7-butyl-5-[(2-cyanophenyl)methyl]-5H,6H,7H,8H,9H,10H-cyclohepta[b]indole-4-carboxylic acid | 1.10 | 0.03 | 87.30 | 0.72 | 91.50 | 7.07 |
| 7-butyl-5-[(2-methylphenyl)methyl]-5H,6H,7H,8H,9H,10H-cyclohepta[b]indole-4-carboxylic acid | 1.12 | 0.03 | 95.31 | 3.47 | 100.87 | 3.68 |
| 7-butyl-5-[(2-fluorophenyl)methyl]-5H,6H,7H,8H,9H,10H-cyclohepta[b]indole-4-carboxylic acid | 1.11 | 0.09 | 88.10 | 5.30 | 92.06 | 4.48 |
| 5-[(3-carbamoylphenyl)methyl]- | 1.27 | 0.01 | 93.32 | 2.47 | 91.21 | 3.77 |

TABLE 3-continued

| IUPAC Name | Glucose consumption (fold change) Mean | Standard Deviation | FABP4 inhibition (%) at 10 µM Mean | Standard Deviation | FABP4 inhibition (%) at 1 µM Mean | Standard Deviation |
| --- | --- | --- | --- | --- | --- | --- |
| 7-pentyl-5H,6H,7H,8H,9H,10H-cyclohepta[b]indole-4-carboxylic acid | | | | | | |
| 5-[(3-cyanophenyl)methyl]-7-pentyl-5H,6H,7H,8H,9H,10H-cyclohepta[b]indole-4-carboxylic acid | 1.35 | 0.00 | 96.09 | 3.74 | 100.38 | 6.94 |
| 5-[(3-carbamoylphenyl)methyl]-7-(2-phenylethyl)-5H,6H,7H,8H,9H,10H-cyclohepta[b]indole-4-carboxylic acid | N.D. | | 98.04 | 2.98 | 99.08 | 2.15 |
| 5-[(3-cyanophenyl)methyl]-7-(2-phenylethyl)-5H,6H,7H,8H,9H,10H-cyclohepta[b]indole-4-carboxylic acid | 1.02 | 0.10 | 94.55 | 1.81 | 93.10 | 2.67 |
| 5-[(3-carbamoylphenyl)methyl]-7-hexyl-5H,6H,7H,8H,9H,10H-cyclohepta[b]indole-4-carboxylic acid | 1.26 | 0.03 | 94.16 | 3.93 | 101.55 | 6.09 |
| 5-[(3-cyanophenyl)methyl]-7-hexyl-5H,6H,7H,8H,9H,10H-cyclohepta[b]indole-4-carboxylic acid | 1.26 | 0.01 | 88.70 | 1.75 | 94.10 | 5.70 |
| 5-[(3-carbamoylphenyl)methyl]-7-octyl-5H,6H,7H,8H,9H,10H-cyclohepta[b]indole-4-carboxylic acid | 1.13 | 0.03 | 93.61 | 5.74 | 98.10 | 12.50 |
| 5-[(3-cyanophenyl)methyl]-7-octyl-5H,6H,7H,8H,9H,10H- | 1.12 | 0.04 | 93.03 | 3.55 | 94.55 | 2.06 |

TABLE 3-continued

| IUPAC Name | Glucose consumption (fold change) Mean | Standard Deviation | FABP4 inhibition (%) at 10 μM Mean | Standard Deviation | FABP4 inhibition (%) at 1 μM Mean | Standard Deviation |
|---|---|---|---|---|---|---|
| cyclohepta[b]indole-4-carboxylic acid | | | | | | |
| 5-[(3-fluorophenyl)methyl]-7-hexyl-5H,6H,7H,8H,9H,10H-cyclohepta[b]indole-4-carboxylic acid | 1.14 | 0.07 | 92.94 | 2.30 | 93.56 | 6.10 |
| 7-hexyl-5-[(pyridin-3-yl)methyl]-5H,6H,7H,8H,9H,10H-cyclohepta[b]indole-4-carboxylic acid | 1.14 | 0.05 | 97.30 | 1.45 | 105.24 | 9.00 |
| 7-hexyl-5-[(3-methylphenyl)methyl]-5H,6H,7H,8H,9H,10H-cyclohepta[b]indole-4-carboxylic acid | 1.13 | 0.03 | 94.68 | 4.27 | 98.63 | 3.46 |
| 7-hexyl-5-[(3-methoxyphenyl)methyl]-5H,6H,7H,8H,9H,10H-cyclohepta[b]indole-4-carboxylic acid | 1.13 | 0.00 | 93.59 | 5.69 | 93.23 | 4.03 |
| 5-[(3-chlorophenyl)methyl]-7-hexyl-5H,6H,7H,8H,9H,10H-cyclohepta[b]indole-4-carboxylic acid | 1.18 | 0.00 | 45.91 | 42.86 | 102.84 | 4.45 |
| 7-hexyl-5-[(2-methoxypyridin-4-yl)methyl]-5H,6H,7H,8H,9H,10H-cyclohepta[b]indole-4-carboxylic acid | 1.12 | 0.03 | 82.81 | 1.77 | 78.13 | 5.92 |
| 5-[(3-carboxyphenyl)methyl]-7-hexyl-5H,6H,7H,8H,9H,10H-cyclohepta[b]indole-4-carboxylic acid | 1.15 | 0.00 | 89.21 | 1.85 | 89.78 | 3.93 |

TABLE 3-continued

| IUPAC Name | Glucose consumption (fold change) Mean | Standard Deviation | FABP4 inhibition (%) at 10 μM Mean | Standard Deviation | FABP4 inhibition (%) at 1 μM Mean | Standard Deviation |
|---|---|---|---|---|---|---|
| 5-[(4-carbamoylphenyl)methyl]-7-hexyl-5H,6H,7H,8H,9H,10H-cyclohepta[b]indole-4-carboxylic acid | 1.05 | 0.00 | 83.82 | 1.05 | 77.65 | 2.37 |
| 5-[(2-carbamoylphenyl)methyl]-7-hexyl-5H,6H,7H,8H,9H,10H-cyclohepta[b]indole-4-carboxylic acid | 0.97 | 0.05 | 82.04 | 2.38 | 79.18 | 6.48 |
| 7-hexyl-5-[(4-methylphenyl)methyl]-5H,6H,7H,8H,9H,10H-cyclohepta[b]indole-4-carboxylic acid | 1.05 | 0.02 | 91.67 | 11.79 | 95.59 | 4.31 |
| 5-[(4-cyanophenyl)methyl]-7-hexyl-5H,6H,7H,8H,9H,10H-cyclohepta[b]indole-4-carboxylic acid | 0.94 | 0.03 | 84.65 | 4.88 | 81.28 | 2.79 |
| 5-[(2-cyanophenyl)methyl]-7-hexyl-5H,6H,7H,8H,9H,10H-cyclohepta[b]indole-4-carboxylic acid | 0.91 | 0.00 | 88.61 | 0.70 | 88.51 | 3.49 |
| 7-hexyl-5-[(2-methylphenyl)methyl]-5H,6H,7H,8H,9H,10H-cyclohepta[b]indole-4-carboxylic acid | 1.00 | 0.03 | 84.23 | 3.88 | 92.71 | 1.33 |
| 5-[(2-fluorophenyl)methyl]-7-hexyl-5H,6H,7H,8H,9H,10H-cyclohepta[b]indole-4-carboxylic acid | 1.17 | 0.04 | 87.30 | 6.15 | 77.54 | 5.88 |
| 5-[(4-fluorophenyl)methyl]-7-hexyl- | 1.17 | 0.10 | 77.60 | 2.50 | 74.41 | 4.82 |

TABLE 3-continued

| IUPAC Name | Glucose consumption (fold change) Mean | Standard Deviation | FABP4 inhibition (%) at 10 μM Mean | Standard Deviation | FABP4 inhibition (%) at 1 μM Mean | Standard Deviation |
|---|---|---|---|---|---|---|
| 5H,6H,7H,8H,9H,10H-cyclohepta[b]indole-4-carboxylic acid | | | | | | |
| 9-[(3-carbamoylphenyl)methyl]-2-hexyl-2,3,4,9-tetrahydro-1H-carbazole-8-carboxylic acid | 1.13 | 0.03 | 90.45 | 0.43 | 92.76 | 4.16 |
| 9-[(3-cyanophenyl)methyl]-2-hexyl-2,3,4,9-tetrahydro-1H-carbazole-8-carboxylic acid | 1.16 | 0.03 | 83.38 | 8.29 | 63.63 | 1.64 |
| 9-[(3-carboxyphenyl)methyl]-2-hexyl-2,3,4,9-tetrahydro-1H-carbazole-8-carboxylic acid | 1.01 | 0.11 | 72.96 | 5.81 | 23.88 | 14.24 |
| 2-hexyl-9-[(pyridin-3-yl)methyl]-2,3,4,9-tetrahydro-1H-carbazole-8-carboxylic acid | 1.21 | 0.07 | N.D. | | N.D. | |
| 2-hexyl-9-[(3-hydroxyphenyl)methyl]-2,3,4,9-tetrahydro-1H-carbazole-8-carboxylic acid | 1.11 | 0.00 | 93.09 | 4.30 | 77.86 | 5.25 |
| 2-hexyl-9-[(2-methoxypyridin-4-yl)methyl]-2,3,4,9-tetrahydro-1H-carbazole-8-carboxylic acid | 1.19 | 0.04 | 77.82 | 4.70 | 44.22 | 7.18 |
| 9-[(3-carboxyphenyl)methyl]-2-hexyl-2,3,4,9-tetrahydro- | N.D. | | 80.24 | 4.24 | 42.40 | 4.80 |

TABLE 3-continued

| IUPAC Name | Glucose consumption (fold change) Mean | Standard Deviation | FABP4 inhibition (%) at 10 μM Mean | Standard Deviation | FABP4 inhibition (%) at 1 μM Mean | Standard Deviation |
|---|---|---|---|---|---|---|
| 1H-carbazole-8-carboxylic acid | | | | | | |
| 9-[(4-carbamoylphenyl)methyl]-2-hexyl-2,3,4,9-tetrahydro-1H-carbazole-8-carboxylic acid | N.D. | | 89.27 | 7.22 | 87.30 | 5.09 |
| 9-[(2-carbamoylphenyl)methyl]-2-hexyl-2,3,4,9-tetrahydro-1H-carbazole-8-carboxylic acid | N.D. | | 80.74 | 5.59 | 31.12 | 6.48 |
| 2-hexyl-9-[(4-methylphenyl)methyl]-2,3,4,9-tetrahydro-1H-carbazole-8-carboxylic acid | N.D. | | 88.47 | 4.23 | 74.28 | 6.79 |
| 9-[(4-cyanophenyl)methyl]-2-hexyl-2,3,4,9-tetrahydro-1H-carbazole-8-carboxylic acid | N.D. | | 78.90 | 4.26 | 39.74 | 4.51 |
| 9-[(2-cyanophenyl)methyl]-2-hexyl-2,3,4,9-tetrahydro-1H-carbazole-8-carboxylic acid | 1.13 | 0.03 | 92.72 | 3.52 | 87.33 | 7.02 |
| 2-hexyl-9-[(2-methylphenyl)methyl]-2,3,4,9-tetrahydro-1H-carbazole-8-carboxylic acid | 1.23 | 0.01 | 83.16 | 6.50 | 87.40 | 2.66 |
| 9-[(2-fluorophenyl)methyl]-2-hexyl-2,3,4,9-tetrahydro-1H-carbazole-8-carboxylic acid | 1.24 | 0.02 | 84.93 | 4.93 | 81.82 | 9.38 |

TABLE 3-continued

| IUPAC Name | Glucose consumption (fold change) Mean | Standard Deviation | FABP4 inhibition (%) at 10 μM Mean | Standard Deviation | FABP4 inhibition (%) at 1 μM Mean | Standard Deviation |
|---|---|---|---|---|---|---|
| 9-[(3-carbamoylphenyl)methyl]-2-(2-phenylethyl)-2,3,4,9-tetrahydro-1H-carbazole-8-carboxylic acid | n.d. | | 94.12 | 6.56 | 98.44 | 3.55 |
| 9-[(3-cyanophenyl)methyl]-2-(2-phenylethyl)-2,3,4,9-tetrahydro-1H-carbazole-8-carboxylic acid | n.d. | | 92.33 | 5.58 | 92.65 | 2.83 |
| 9[(3-carbamoylphenyl)methyl]-4-(2-phenylethyl)-2,3,4,9-tetrahydro-1H-carbazole-8-carboxylic acid | n.d. | | 77.91 | 0.56 | 44.14 | 3.62 |
| 9-[(3-cyanophenyl)methyl]-4-(2-phenylethyl)-2,3,4,9-tetrahydro-1H-carbazole-8-carboxylic acid | 1.10 | 0.01 | 53.44 | 4.98 | 31.03 | 7.46 |
| 9-[(3-carbamoylphenyl)methyl]-2-propyl-2,3,4,9-tetrahydro-1H-carbazole-8-carboxylic acid | 1.09 | 0.02 | 88.00 | 6.66 | 83.59 | 3.12 |
| 9-[(3-cyanophenyl)methyl]-2-propyl-2,3,4,9-tetrahydro-1H-carbazole-8-carboxylic acid | 1.21 | 0.00 | 81.41 | 4.67 | 55.57 | 7.71 |
| 2-butyl-9-[(3-carbamoyl-phenyl)methyl]-2,3,4,9-tetrahydro-1H-carbazole-8-carboxylic acid | 1.10 | 0.08 | 95.49 | 0.69 | 88.54 | 9.35 |

TABLE 3-continued

| IUPAC Name | Glucose consumption (fold change) Mean | Standard Deviation | FABP4 inhibition (%) at 10 μM Mean | Standard Deviation | FABP4 inhibition (%) at 1 μM Mean | Standard Deviation |
| --- | --- | --- | --- | --- | --- | --- |
| 9-[(3-carbamoyl-phenyl)methyl]-2-pentyl-2,3,4,9-tetrahydro-1H-carbazole-8-carboxylic acid | 1.13 | 0.04 | 67.03 | 28.39 | 75.03 | 5.11 |
| 9-[(3-cyanophenyl)methyl]-2-pentyl-2,3,4,9-tetrahydro-1H-carbazole-8-carboxylic acid | 1.34 | 0.03 | 77.06 | 3.04 | 60.75 | 9.35 |
| 1-butyl-9-[(3-carbamoyl-phenyl)methyl]-2,3,4,9-tetrahydro-1H-carbazole-8-carboxylic acid | 1.02 | 0.02 | 86.24 | 6.94 | 83.05 | 5.37 |
| 9-[(3-carbamoyl-phenyl)methyl]-1-(pentyloxy)-2,3,4,9-tetrahydro-1H-carbazole-8-carboxylic acid | 1.09 | 0.02 | 100.36 | 4.05 | 81.93 | 2.72 |
| 9-[(3-cyanophenyl)methyl]-1-(pentyloxy)-2,3,4,9-tetrahydro-1H-carbazole-8-carboxylic acid | 1.19 | 0.04 | 63.30 | 5.49 | 7.56 | 7.21 |
| 1-butyl-9-[(3-cyanophenyl)methyl]-2,3,4,9-tetrahydro-1H-carbazole-8-carboxylic acid | 1.14 | 0.00 | 93.67 | 1.80 | 57.97 | 3.09 |
| 6-butyl-5-[(3-carbamoyl-phenyl)methyl]-5H,6H,7H,8H,9H,10H-cyclohepta[b]indole-4-carboxylic acid | 1.03 | 0.02 | 95.15 | 2.57 | 91.41 | 4.19 |
| 6-butyl-5-[(3-cyanophenyl) | 1.16 | 0.04 | 85.67 | 7.45 | 71.34 | 3.30 |

TABLE 3-continued

| IUPAC Name | Glucose consumption (fold change) Mean | Standard Deviation | FABP4 inhibition (%) at 10 μM Mean | Standard Deviation | FABP4 inhibition (%) at 1 μM Mean | Standard Deviation |
|---|---|---|---|---|---|---|
| methyl]-5H,6H,7H,8H,9H,10H-cyclohepta[b]indole-4-carboxylic acid | | | | | | |
| 9-[(3-carbamoyl-phenyl)methyl]-1-ethyl-2,3,4,9-tetrahydro-1H-carbazole-8-carboxylic acid | 0.94 | 0.00 | 95.91 | 0.97 | 90.27 | 2.15 |
| 9-[(3-cyanophenyl)methyl]-1-ethyl-2,3,4,9-tetrahydro-1H-carbazole-8-carboxylic acid | 1.11 | 0.01 | 87.60 | 4.09 | 44.21 | 6.98 |
| 9-[(3-carboxyphenyl)methyl]-1-ethyl-2,3,4,9-tetrahydro-1H-carbazole-8-carboxylic acid | 1.09 | 0.01 | 78.55 | 4.96 | 39.62 | 3.73 |
| 9-[(3-carbamoyl-ephnyl)methyl]-1-propoxy-2,3,4,9-tetrahydro-1H-carbazole-8-carboxylic acid | 1.03 | 0.01 | 91.95 | 3.37 | 57.57 | 5.01 |
| 9-[(3-carbamoyl-phenyl)methyl]-4-ethyl-2,3,4,9-tetrahydro-1H-carbazole-8-carboxylic acid | 1.21 | 0.07 | 102.19 | 3.54 | 87.03 | 3.76 |
| 4-[(3-carbamoyl-phenyl)methyl]-3-ethyl-1H,2H,3H,4H-cyclopenta[b]indole-5-carboxylic acid | 1.02 | 0.05 | 101.60 | 8.01 | 87.35 | 2.64 |
| 4-[(3-cyanophenyl)methyl]-3-ethyl-1H,2H,3H,4H-cyclopenta[b]indole-5-carboxylic acid | 1.12 | 0.06 | 86.15 | 3.77 | 54.79 | 9.38 |

TABLE 3-continued

| IUPAC Name | Glucose consumption (fold change) Mean | Standard Deviation | FABP4 inhibition (%) at 10 μM Mean | Standard Deviation | FABP4 inhibition (%) at 1 μM Mean | Standard Deviation |
|---|---|---|---|---|---|---|
| 3-butyl-4-[(3-carbamoyl-phenyl)methyl]-1H,2H,3H,4H-cyclopenta[b]indole-5-carboxylic acid | 1.15 | 0.04 | 98.53 | 7.00 | 96.85 | 4.65 |
| 3-butyl-4-[(3-cyanophenyl)methyl]-1H,2H,3H,4H-cyclopenta[b]indole-5-carboxylic acid | 1.21 | 0.06 | 98.54 | 5.39 | 85.13 | 2.82 |
| 2-butyl-4-[(3-carbamoyl-phenyl)methyl]-1H,2H,3H,4H-cyclopenta[b]indole-5-carboxylic acid | 1.14 | 0.04 | 95.21 | 1.97 | 87.15 | 1.08 |
| 2-butyl-4-[(3-cyanophenyl)methyl]-1H,2H,3H,4H-cyclopenta[b]indole-5-carboxylic acid | 1.28 | 0.02 | 85.14 | 9.63 | 62.12 | 5.33 |
| 5-[(3-carbamoyl phenyl)methyl]-10-ethyl-5H,6H,7H,8H,9H,10H-cyclohepta[b]indole-4-carboxylic acid | 0.99 | 0.03 | 98.00 | 1.95 | 86.38 | 4.41 |
| 5-[(3-cyanophenyl)methyl]-10-ethyl-5H,6H,7H,8H,9H,10H-cyclohepta[b]indole-4-carboxylic acid | 1.15 | 0.00 | 98.24 | 4.40 | 92.43 | 5.77 |
| 5-[(3-carbamoyl phenyl)methyl]-10-propyl-5H,6H,7H,8H,9H,10H-cyclohepta[b]indole-4-carboxylic acid | 1.02 | 0.04 | 91.62 | 2.09 | 38.78 | 7.53 |
| 5-[(3-cyanophenyl)methyl]-10-propyl-5H,6H,7H,8H,9H,10H- | 1.18 | 0.01 | 97.55 | 4.36 | 73.32 | 4.30 |

TABLE 3-continued

| IUPAC Name | Glucose consumption (fold change) Mean | Standard Deviation | FABP4 inhibition (%) at 10 μM Mean | Standard Deviation | FABP4 inhibition (%) at 1 μM Mean | Standard Deviation |
| --- | --- | --- | --- | --- | --- | --- |
| cyclohepta[b]indole-4-carboxylic acid | | | | | | |
| 9-[(3-carboxyphenyl)methyl]-4-ethyl-2,3,4,9-tetrahydro-1H-carbazole-8-carboxylic acid | 1.06 | 0.01 | 85.38 | 3.02 | 52.11 | 3.11 |
| 9-[(3-carbamoyl-phenyl)methyl]-3-ethyl-2,3,4,9-tetrahydro-1H-carbazole-8-carboxylic acid | 1.10 | 0.02 | 103.25 | 3.15 | 98.24 | 1.74 |
| 10-butyl-5-[(3-carbamoyl-phenyl)methyl]-5H,6H,7H,8H,9H,10H-cyclohepta[b]indole-4-carboxylic acid | 1.14 | 0.00 | 87.88 | 6.31 | 63.30 | 6.49 |
| 10-butyl-5-[(3-cyanophenyl)methyl]-5H,6H,7H,8H,9H,10H-cyclohepta[b]indole-4-carboxylic acid | 1.24 | 0.05 | 73.63 | 1.45 | 30.87 | 9.67 |
| 5-[(3-carbamoyl-phenyl)methyl]-10-pentyl-5H,6H,7H,8H,9H,10H-cyclohepta[b]indole-4-carboxylic acid | 1.27 | 0.05 | 96.14 | 5.04 | 81.14 | 2.85 |
| 5-[(3-cyanophenyl)methyl]-10-pentyl-5H,6H,7H,8H,9H,10H-cyclohepta[b]indole-4-carboxylic acid | 1.20 | 0.03 | 76.96 | 3.53 | 44.31 | 1.32 |
| 4-[(3-carbamoyl-phenyl)methyl]-2-pentyl-1H,2H,3H,4H-cyclopenta[b]indole-5-carboxylic acid | 0.68 | 0.00 | 93.08 | 1.08 | 86.88 | 3.08 |

TABLE 3-continued

| IUPAC Name | Glucose consumption (fold change) Mean | Standard Deviation | FABP4 inhibition (%) at 10 μM Mean | Standard Deviation | FABP4 inhibition (%) at 1 μM Mean | Standard Deviation |
|---|---|---|---|---|---|---|
| 4-[3-cyanophenyl)methyl]-2-pentyl-1H,2H,3H,4H-cyclopenta[b]indole-5-carboxylic acid | 1.18 | 0.08 | 78.31 | 10.06 | 39.48 | 8.52 |
| 9-[(3-carbamoyl-phenyl)methyl]-2-ethyl-2,3,4,9-tetrahydro-1H-carbazole-8-carboxylic acid | 1.06 | 0.06 | 100.70 | 1.67 | 85.46 | 2.84 |
| 9-[(3-carboxyphenyl)methyl]-2-ethyl-2,3,4,9-tetrahydro-1H-carbazole-8-carboxylic acid | 1.11 | 0.06 | 69.18 | 8.93 | 23.47 | 0.85 |
| 5-[(3-carbamoyl-phenyl)methyl]-7-ethyl-5H,6H,7H,8H,9H,10H-cyclohepta[b]indole-4-carboxylic acid | 0.96 | 0.14 | 100.11 | 0.22 | 91.82 | 5.87 |
| 5-[(3-cyanophenyl)methyl]-7-ethyl-5H,6H,7H,8H,9H,10H-cyclohepta[b]indole-4-carboxylic acid | 1.16 | 0.03 | 97.05 | 4.07 | 90.00 | 4.80 |
| 9-[(3-cyanophenyl)methyl-3-ethyl-2,3,4,9-tetrahydro-1H-carbazole-8-carboxylic acid | 1.08 | 0.02 | 90.34 | 3.77 | 45.83 | 4.50 |
| 9-[(3-carbamoyl-phenyl)methy]-4-propyl-2,3,4,9-tetrahydro-1H-carbazole-8-carboxylic acid | 1.04 | 0.05 | 89.99 | 2.36 | 53.85 | 6.44 |
| 9-[(3-carbamoyl-phenyl)methyl]-3-propyl-2,3,4,9-tetrahydro-1H- | 1.10 | 0.01 | 99.18 | 1.85 | 87.33 | 5.21 |

TABLE 3-continued

| IUPAC Name | Glucose consumption (fold change) Mean | Standard Deviation | FABP4 inhibition (%) at 10 μM Mean | Standard Deviation | FABP4 inhibition (%) at 1 μM Mean | Standard Deviation |
|---|---|---|---|---|---|---|
| carbazole-8-carboxylic acid | | | | | | |
| 9-[(3-cyanophenyl)methyl]-3-propyl-2,3,4,9-tetrahydro-1H-carbazole-8-carboxylic acid | 1.20 | 0.04 | 85.39 | 2.92 | 46.78 | 4.58 |
| 4-butyl-9-[(3-carbamoyl-phenyl)methyl]-2,3,4,9-tetrahydro-1H-carbazole-8-carboxylic acid | 1.35 | 0.02 | 83.41 | 3.07 | 43.27 | 0.87 |
| 4-butyl-9-[(3-cyanophenyl)methyl]-2,3,4,9-tetrahydro-1H-carbazole-8-carboxylic acid | 1.28 | 0.02 | 65.48 | 5.25 | 25.30 | 11.15 |
| 3-butyl-9-[(3-carbamoyl-phenyl)methyl]-2,3,4,9-tetrahydro-1H-carbazole-8-carboxylic acid | 1.09 | 0.04 | 97.21 | 3.11 | 92.39 | 3.47 |
| 3-butyl-9-[(3-cyanophenyl)methyl]-2,3,4,9-tetrahydro-1H-carbazole-8-carboxylic acid | 1.14 | 0.07 | 81.09 | 3.73 | 35.80 | 1.49 |
| 9-[(3-carbamoyl-phenyl)methyl]-4-pentyl-2,3,4,9-tetrahydro-1H-carbazole-8-carboxylic acid | 1.12 | 0.02 | 84.44 | 2.27 | 42.64 | 4.86 |
| 9-[(3-cyanophenyl)methyl]-4-pentyl-2,3,4,9-tetrahydro-1H-carbazole-8-carboxylic acid | 1.13 | 0.04 | 73.70 | 3.05 | 26.27 | 6.63 |

TABLE 3-continued

| IUPAC Name | Glucose consumption (fold change) Mean | Standard Deviation | FABP4 inhibition (%) at 10 μM Mean | Standard Deviation | FABP4 inhibition (%) at 1 μM Mean | Standard Deviation |
| --- | --- | --- | --- | --- | --- | --- |
| 9-[(3-carbamoyl-phenyl)methyl]-3-pentyl-2,3,4,9-tetrahydro-1H-carbazole-8-carboxylic acid | 1.08 | 0.05 | 98.44 | 3.02 | 90.93 | 5.66 |
| 9-[(3-cyanophenyl)methyl]-3-pentyl-2,3,4,9-tetrahydro-1H-carbazole-8-carboxylic acid | 1.17 | 0.00 | 83.34 | 6.35 | 57.36 | 2.64 |
| 4-[(3-carbamoyl-phenyl)methyl]-3-propyl-1H,2H,3H,4H-cyclopenta[b]indole-5-carboxylic acid | 1.18 | 0.00 | 95.27 | 2.16 | 89.06 | 3.85 |
| 4-[(3-cyanophenyl)methyl]-3-propyl-1H,2H,3H,4H-cyclopenta[b]indole-5-carboxylic acid | 1.38 | 0.08 | 97.64 | 5.64 | 67.85 | 5.18 |
| 2-({7-butyl-5-[3-carbamoyl phenyl)methyl]-5H,6H,7H,8H,9H,10H-cyclohepta[b]indol-4-yl]formamido) acetic acid | 0.90 | 0.05 | 90.18 | 3.23 | 59.02 | 7.71 |
| 2-({7-butyl-5-[(3-cyanophenyl)methyl]-5H,6H,7H,8H,9H,10H-cyclohepta[b]indol-4-yl}formamido) acetic acid | 1.20 | 0.05 | 40.99 | 9.54 | 8.61 | 10.28 |
| 7-butyl-5-[(3-carbamoyl phenyl)methyl]-N-(2-hydroxyethyl)-5H,6H,7H,8H,9H,10H-cyclohepta[b]indole-4-carboxamide | 0.98 | 0.02 | N.A. | | 10.23 | 4.72 |
| 7-butyl-5-[(3-cyanophenyl)methyl]-N-(2- | 1.08 | 0.01 | 42.68 | 2.54 | 6.65 | 6.50 |

TABLE 3-continued

| IUPAC Name | Glucose consumption (fold change) Mean | Standard Deviation | FABP4 inhibition (%) at 10 µM Mean | Standard Deviation | FABP4 inhibition (%) at 1 µM Mean | Standard Deviation |
| --- | --- | --- | --- | --- | --- | --- |
| hydroxyethyl)-5H,6H,7H,8H,9H,10H-cyclohepta[b]indole-4-carboxamide | | | | | | |
| 7-butyl-5-[(3-fluorophenyl)methyl]-5H,6H,7H,8H,9H,10H-cyclohepta[b]indole-4-carboxylic acid | 1.12 | 0.03 | 90.57 | 5.37 | 96.96 | 1.18 |
| 7-butyl-5-[(3-carboxyphenyl)methyl]-5H,6H,7H,8H,9H,10H-cyclohepta[b]indole-4-carboxylic acid | 0.95 | 0.02 | 100.35 | 7.59 | 91.80 | 7.00 |

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A compound of Formula I-comprising:

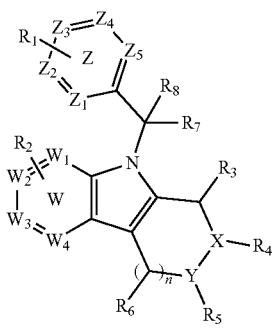

Formula (I)

Wherein:

$W_{1-4}$ and $Z_1$-$Z_5$ are each independently —C, —CH, O, S, or N;

X is independently $CH_2$, N or $CHR_4$;

Y is independently $CH_2$, or $CHR_5$;

n is a number between 0 and 3;

One or more $R_1$'s on the ring Z are independently selected from the group consisting of: CN, OH, COOH, $OCH_3$, $CF_3$, $CONH_2$, $B(OH)_2$, $B(OR)_2$, an acid isostere, a substituted amine, ethers, and a halogen, substituted or unsubstituted alkyl, substituted or unsubstituted cyclic or heterocyclic, substituted or unsubstituted cycloaryl or cycloheteroaryl, wherein the substituted cycloaryl or cycloheteroaryl may be substituted with hydrogen, CN, OH, COOH, $OCH_3$, $CF_3$, $CONH_2$, $B(OH)_2$, $B(OR)_2$, an acid isostere, a substituted amine, ethers, and a halogen, substituted or unsubstituted alkyl, substituted or unsubstituted cyclic or heterocyclic, substituted or unsubstituted cycloaryl or cycloheteroaryl, and $SO_2NH_2$;

One or more $R_2$'s on the ring W are independently selected from the group consisting of: CN, OH, $CHF_2$, $CH_2F$, $CF_3$, COOH, $CONH_2$, $B(OH)_2$, $B(OR)_2$, an acid isostere, a halogen, and a bicyclic heteroaryl;

$R_7$ is hydrogen or CN, COOH, $CONH_2$, $B(OH)_2$, $B(OR)_2$ or an acid isostere;

R is alkyl;

$R_3$, $R_4$, $R_5$ or $R_8$, or $R_6$ when n is not zero, is each independently selected from:

(1) hydrogen;

(2) an alkyl or ether having 2 to 12 carbon atoms, (3) a substituted amine, or (4) —$(CH_2)m$ G, wherein m is 1 to 12 and G is independently selected from:

(a) cycloalkyl containing 3 to 6 carbon atoms, (b) aryl or heteroaryl, (c) $CF_3$, $CF_2H$ or $CFH_2$, or (d) a heterocycle, provided that $R_3$, $R_4$, $R_5$, $R_8$, or $R_6$ are not all hydrogen; and wherein the acid isostere is selected from the group consisting of

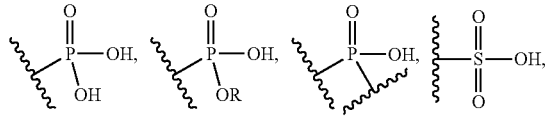

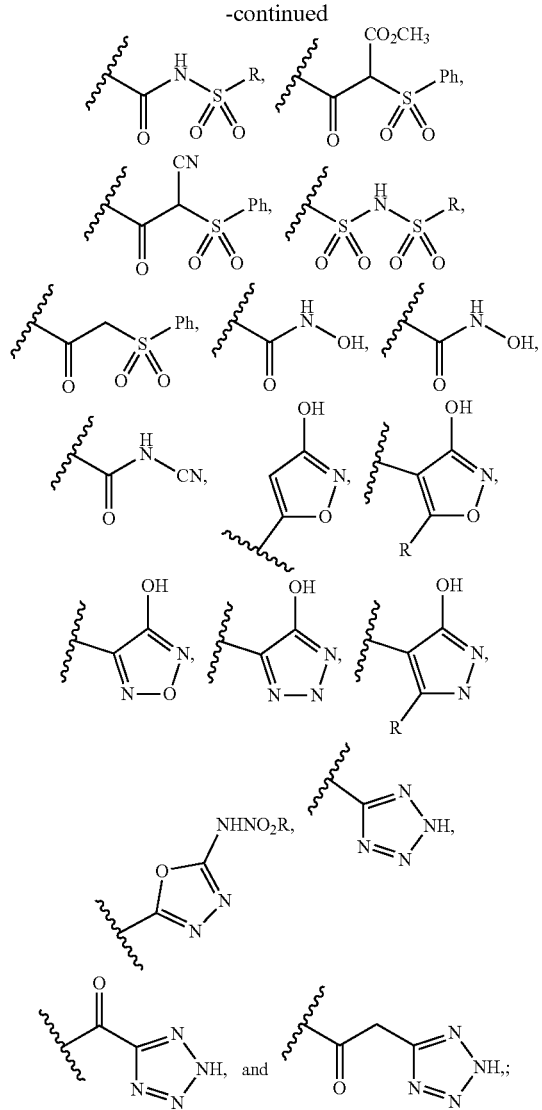

or pharmaceutically acceptable salts or stereoisomers thereof.

2. The compound according to claim 1, wherein Ri and $R_2$ are each independently CN, COOH, or $CONH_2$.

3. The compound according to claim 1, wherein the Formula I includes multiple $R_1$'s and $R_2$'s.

4. The compound according to claim 1, wherein $R_3$, $R_4$, $R_5$, $R_8$, or $R_6$ when n is not zero, is each independently alkyl having 4 carbon atoms.

5. The compound according to claim 1, wherein $R_3$, $R_4$, $R_5$, $R_8$, or $R_6$ when n is not zero, is each independently alkyl having 5 carbon atoms.

6. The compound according to claim 1, wherein $R_3$, $R_4$, $R_5$, $R_8$, or $R_6$ when n is not zero, is each independently alkyl having 6 carbon atoms.

7. The compound according to claim 1, wherein the ring Z is a phenyl group.

8. The compound according to claim 1, wherein the one or more $R_1$'s on the ring Z are independently selected from the group consisting of: CN, OH, COOH, $OCH_3$, $CF_3$, $CONH_2$, $B(OH)_2$, $B(OR)_2$, and a halogen.

9. The compound according to claim 1, wherein the one or more $R_1$'s on the ring Z is halogen.

10. The compound according to claim 1, wherein the one or more $R_1$'s on the ring Z is CN.

11. The compound according to claim 1, wherein the one or more $R_1$'s on the ring Z is $CF_3$.

12. The compound according to claim 1, wherein the one or more $R_2$'s on the ring W is halogen.

13. The compound according to claim 1, wherein the one or more $R_1$'s on the ring Z comprise are CN and/or halogen.

14. The compound according to claim 1, wherein the one or more $R_1$'s on the ring Z are CN and/or halogen, and wherein the one or more $R_2$'s on the ring W are another halogen.

15. The compound according to claim 14, wherein the halogen is identical to the other halogen.

16. The compound according to claim 14, wherein the halogen differs from the other halogen.

17. A compound of Formula II:

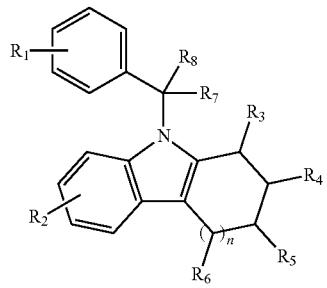

Wherein:

n=0, 1, or 2;

$R_1$ is selected from the group consisting of: CN, COOH, $CONH_2$, $B(OH)_2$, $B(OR)_2$, an acid isostere, and a halogen wherein the halogen is not a fluoro substituent;

$R_2$ is selected from the group consisting of: CN, COOH, $CONH_2$, $B(OH)_2$, $B(OR)_2$, an acid isostere, a halogen, and a bicyclic heteroaryl;

$R_7$ is hydrogen or CN, COOH, $CONH_2$, $B(OH)_2$, $B(OR)_2$ or an acid isostere, wherein the acid isostere is selected from the group consisting of;

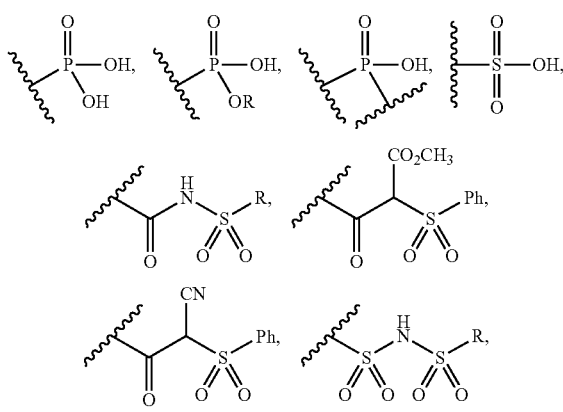

R is alkyl;

$R_3$, $R_4$, $R_5$ or $R_8$, or $R_6$ when n is not zero, is each independently selected from:
(1) hydrogen;
(2) alkyl having 1 to 12 carbon atoms, or
(3) —(CH$_2$)$_m$ G, wherein m is 1 to 12 and G is independently selected from:
   (a) cycloalkyl containing 3 to 6 carbon atoms,
   (b) aryl or heteroaryl, or
   (c) CF$_3$, CF$_2$H or CFH$_2$;
provided that G is not a nitrogen or oxygen-containing group; and
provided that $R_3$, $R_4$, $R_5$, $R_8$, or $R_6$ are not all hydrogen;
or pharmaceutically acceptable salts thereof.

18. The compound according to claim 17, wherein $R_1$ and $R_2$ are each independently CN, COOH, or CONH$_2$.

19. The compound according to claim 17, wherein the Formula II includes multiple $R_1$'s and $R_2$'s.

20. The compound according to claim 17, wherein $R_3$, $R_4$, $R_5$, $R_8$, or $R_6$ when n is not zero, is each independently alkyl having 4 carbon atoms.

21. The compound according to claim 17, wherein $R_3$, $R_4$, $R_5$, $R_8$, or $R_6$ when n is not zero, is each independently alkyl having 5 carbon atoms.

22. The compound according to claim 17, wherein $R_3$, $R_4$, $R_5$, $R_8$, or $R_6$ when n is not zero, is each independently alkyl having 6 carbon atoms.

23. A compound of Formula III &

Wherein:
n=0, 1 or 2;
$R_1$ and $R_2$ are each independently CN, COOH or CONH$_2$;
$R_3$ is independently selected from:
(1) alkyl having 1 to 12 carbon atoms;
(2) —(CH$_2$)$_m$G, wherein m is 1 to 12 and G is independently selected from:
   (a) cycloalkyl containing 3 to 6 carbon atoms;
   (b) phenyl;
or pharmaceutically acceptable salts thereof.

24. A compound according to claim 23, wherein n=0 and $R_3$ is attached to the h-, i-or j-position.

25. A compound according to claim 23, wherein: n=1 and $R_3$ is attached to the h-, i-or j-position.

26. A compound according to claim 23, wherein: n=2 and $R_3$ is attached to the h-, i-or j-position.

27. A compound according to claim 1, which is a pure optical isomer.

28. A compound according to claim 23, which is the (+)-isomer.

29. A compound according to claim 23, which is the (−)-isomer.

30. A compound selected from the group consisting of: 5-[(3-cyanophenyl)methyl]-2-fluoro-7-hexyl-5H,6H,7H, 8H,9H, 10H-cyclohepta[b]indole-4-carboxylic acid, 5-[(6-cyanopyridin-2-yl)methyl]-7-hexyl-5H,6H,7H,8H,9H,10H-cyclohepta[b]indole-4-carboxylic acid, 5-[(6-carbamoylpyridin-2-yl)methyl]-7-hexyl-5H,6H,7H,8H,9H, 10H-cyclohepta[b]indole-4-carboxylic acid, 6-({4-carboxy-7-hexyl-5H,6H,7H,8H,9H,10H-cyclohepta[b]indol-5-yl}methyl)pyridine-2-carboxylic acid, 5-[(3-cyano-2-fluorophenyl)methyl]-7-hexyl-5H,6H, 7H, 8H,9H, 10H-cyclohepta[b]indole-4-carboxylic acid, 5-[(1,3-benzoxazol-6-yl)methyl]-7-hexyl-5H,6H,7H,8H,9H,10H-cyclohepta[b]indole-4-carboxylic acid, 5-[(1,3-benzoxazol-5-yl)methyl]-7-hexyl-5H,6H,7H,8H,9H,10H-cyclohepta[b]indole-4-carboxylic acid, 5-[(6-fluoropyridin-2-yl)methyl]-7-hexyl-5H,6H,7H,8H,9H,10H-cyclohepta[b]indole-4-carboxylic acid, 5-[(2-fluoropyridin-4-yl)methyl]-7-hexyl-5H,6H,7H, 8H,9H, 10H-cyclohepta[b]indole-4-carboxylic acid, 7-hexyl-5-{[6-(trifluoromethyl)pyridin-2-yl]methyl}-5H, 6H,7H,8H,9H,10H-cyclohepta[b]indole-4-carboxylic acid, 7-hexyl-5-{[2-(trifluoromethyl)pyridin-4-yl]methyl}-5H, 6H, 7H, 8H,9H, 10H-cyclohepta[b]indole-4-carboxylic acid, 5-[(5-cyanopyridin-3-yl)methyl]-7-hexyl-5H,6H,7H, 8H,9H,10H-cyclohepta[b]indole-4-carboxylic acid, 5-[(5-cyanothiophen-2-yl)methyl]-7-hexyl-5H,6H,7H,8H,9H, 10H-cyclohepta[b]indole-4-carboxylic acid, 5-[(4-cyanothiophen-2-yl)methyl]-7-hexyl-5H,6H,7H,8H,9H, 10H-cyclohepta[b]indole-4-carboxylic acid, 5-[(5-cyanofuran-2-yl)methyl]-7-hexyl-5H,6H,7H,8H,9H, 10H-cyclohepta[b]indole-4-carboxylic acid, 5-[(3,5-dimethyl-1,2-oxazol-4-yl)methyl]-7-hexyl-5H,6H,7H,8H,9H,10H-cyclohepta[b]indole-4-carboxylic acid, 5-(3-cyanobenzoyl)-7-hexyl-5H,6H,7H,8H,9H,10H-cyclohepta[b]indole-4-carboxylic acid, 5-[(1,3-benzoxazol-7-yl)methyl]-7-hexyl-5H,6H,7H,8H,9H, 10H-cyclohepta[b]indole-4-carboxylic acid, 5-[(5-cyanothiophen-3-yl)methyl]-7-hexyl-5H,6H,7H,8H,9H,10H-cyclohepta[b]indole-4-carboxylic acid, 7-hexyl-5-[(1H-indol-4-yl)methyl]-5H,6H, 7H,8H,9H,10H-cyclohepta[b]indole-4-carboxylic acid, 5-[(3-carbamoylphenyl)methyl]-7-propyl-5H,6H,7H,8H,9H, 10H-cyclohepta[b]indole-4-carboxylic acid, 7-butyl-5-[(3-carbamoylphenyl)methyl]-5H,6H,7H,8H,9H,10H-cyclohepta[b]indole-4-carboxylic acid, 7-butyl-5-[(3-cyanophenyl)methyl]-5H,6H,7H,8H,9H,10H-cyclohepta[b]indole-4-carboxylic acid, 7-butyl-5-[(pyridin-3-yl)methyl]-5H,6H,7H,8H,9H, 10H-cyclohepta[b]indole-4-carboxylic acid, 7-butyl-5-[(3-methylphenyl)methyl]-5H,6H,7H,8H,9H, 10H-cyclohepta[b]indole-4-carboxylic acid, 7-butyl-5-[(3-methoxyphenyl)methyl]-5H,6H, 7H,8H,9H, 10H-cyclohepta[b]indole-4-carboxylic acid, 7-butyl-5-[(3-chlorophenyl)methyl]-5H,6H,7H,8H,9H, 10H-cyclohepta[b]indole-4-carboxylic acid, 7-butyl-5-[(3-hydroxyphenyl)methyl]-5H,6H,7H,8H,9H,10H-cyclohepta[b]indole-4-carboxylic acid, 7-butyl-5-[(2-methoxypyridin-4-yl)methyl]-5H,6H,7H,8H,9H,10H-cyclohepta[b]indole-4-carboxylic acid, 7-butyl-5-[(4-carbamoylphenyl)methyl]-5H,6H, 7H,8H,9H,10H-cyclohepta[b]indole-4-carboxylic acid, 7-butyl-5-[(2-carbamoylphenyl)methyl]-5H,6H, 7H,8H,9H, 10H-cyclohepta[b]indole-4-carboxylic acid, 7-butyl-5-[(4-methylphenyl)methyl]-5H,6H,7H,8H,9H, 10H-cyclohepta[b]indole-4-carboxylic acid, 7-butyl-5-[(2-cyanophenyl)methyl]-5H,6H,7H,8H,9H,10H-cyclohepta[b]indole-4-carboxylic acid, 7-butyl-5-[(2-methylphenyl)methyl]-5H,6H,7H,8H,9H,10H-cyclohepta[b]indole-4-carboxylic acid, 7-butyl-5-[(2-fluorophenyl)methyl]-5H,6H,7H,8H,9H,10H-cyclohepta[b]indole-4-carboxylic acid, 5-[(3-carbamoylphenyl)methyl]-7-pentyl-5H,6H,7H,8H, 9H, 10H-cyclohepta[b]indole-4-carboxylic acid, 5-[(3-cyanophenyl)methyl]-7-pentyl-5H,6H,7H,8H,9H, 10H-cyclohepta[b]indole-4-carboxylic acid, 5-[(3-carbamoylphenyl)methyl]-7-(2-phenylethyl)-5H,6H, 7H, 8H,9H, 10H-cyclohepta[b]indole-4-carboxylic acid, 5-[(3-cyanophenyl)methyl]-7-(2-phenylethyl)-5H,6H,7H,8H,9H,10H-cyclohepta[b]indole-4-carboxylic acid, 5-[(3-carbamoylphenyl)methyl]-7-hexyl-5H,6H,7H,8H,9H,10H-cyclohepta[b]indole-4-carboxylic acid, 5-[(3-cyanophenyl)methyl]-7-hexyl-5H,6H,7H,8H,9H,10H-cyclohepta[b]indole-4-carboxylic acid, 5-[(3-carbamoylphenyl)methyl]-7-octyl-5H,6H,7H,8H,9H,10H-cyclohepta[b]indole-4-carboxylic acid, 5-[(3-cyanophenyl)methyl]-7-octyl-5H,6H, 7H, 8H,9H, 10H-cyclohepta[b]indole-4-carboxylic acid, 5-[(3-fluorophenyl)methyl]-7-hexyl-5H,6H,7H,8H,9H, 10H-cyclohepta[b]indole-4-carboxylic acid, 7-hexyl-5-[(pyridin-3-yl)methyl]-5H,6H,7H,8H,9H, 10H-cyclohepta[b]indole-4-carboxylic acid, 7-hexyl-5-[(3-methylphenyl)methyl]-5H,6H,7H,8H,9H,10H-cyclohepta[b]indole-4-carboxylic acid, 7-hexyl-5-[(3-methoxyphenyl)methyl]-5H,6H,7H,8H,9H, 10H-cyclohepta[b]indole-4-carboxylic acid, 5-[(3-chlorophenyl)methyl]-7-hexyl-5H,6H,7H,8H,9H,10H-cyclohepta[b]indole-4-carboxylic acid, 7-hexyl-5-[(2-methoxypyridin-4-yl)methyl]-5H,6H,7H,8H,9H, 10H-cyclohepta[b]indole-4-carboxylic acid, 5-[(3-carboxyphenyl)methyl]-7-hexyl-5H,6H,7H,8H,9H, 10H-cyclohepta[b]indole-4-carboxylic acid, 5-[(4-carbamoylphenyl)methyl]-7-hexyl-5H,6H, 7H, 8H,9H, 10H-cyclohepta[b]indole-4-carboxylic acid, 5-[(2-carbamoylphenyl)methyl]-7-hexyl-5H,6H, 7H,8H,9H,10H-cyclohepta[b]indole-4-carboxylic acid, 7-hexyl-5-[(4-methylphenyl)methyl]-5H,6H,7H,8H,9H,10H-cyclohepta[b]indole-4-carboxylic acid, 5-[(4-cyanophenyl)methyl]-7-hexyl-5H,6H,7H,8H,9H, 10H-cyclohepta[b]indole-4-carboxylic acid, 5-[(2-cyanophenyl)methyl]-7-hexyl-5H,6H,7H,8H,9H,10H-cyclohepta[b]indole-4-carboxylic acid, 7-hexyl-5-[(2-methylphenyl)methyl]-5H,6H,7H,8H,9H,10H-cyclohepta[b]indole-4-carboxylic acid, 5-[(2-fluorophenyl)methyl]-7-hexyl-5H,6H,7H,8H,9H,10H-cyclohepta[b]indole-4-carboxylic acid, 5-[(4-fluorophenyl)methyl]-7-hexyl-5H,6H,7H,8H,9H, 10H-cyclohepta[b]indole-4-carboxylic acid, 9-[(3-carbamoylphenyl)methyl]-2-hexyl-2,3,4,9-tetrahydro-1H-carbazole-8-carboxylic acid, 9-[(3-cyanophenyl)methyl]-2-hexyl-2,3,4,9-tetrahydro-1H-carbazole-8-carboxylic acid, 9-[(3-carboxyphenyl)methyl]-2-hexyl-2,3,4,9-tetrahydro-1H-carbazole-8-carboxylic acid, 9-[(3-fluorophenyl)methyl]-2-hexyl-2,3,4,9-tetrahydro-1H-carbazole-8-carboxylic acid, 2-hexyl-9-[(pyridin-3-yl)methyl]-2,3,4,9-tetrahydro-1H-carbazole-8-carboxylic acid, 2-hexyl-9-[(3-methylphenyl)methyl]-2,3,4,9-tetrahydro-1H-carbazole-8-carboxylic acid, 2-hexyl-9-[(3-methoxyphenyl)methyl]-2,3,4,9-tetrahydro-1H-carbazole-8-carboxylic acid, 9-[(3-chlorophenyl)methyl]-2-hexyl-2,3,4,9-tetrahydro-1H-carbazole-8-carboxylic acid, 2-hexyl-9-[(3-hydroxyphenyl)methyl]-2,3,4,9-tetrahydro-1H-carbazole-8-carboxylic acid, 2-hexyl-9-[(2-methoxypyridin-4-yl)methyl]-2,3,4,9-tetrahydro-1H-carbazole-8-carboxylic acid, 9-[(3-carboxyphenyl)methyl]-2-hexyl-2,3,4,9-tetrahydro-1H-carbazole-8-carboxylic acid, 9-[(4-carbamoylphenyl)methyl]-2-hexyl-2,3,4,9-tetrahydro-1H-carbazole-8-carboxylic acid, 9-[(2-carbamoylphenyl)methyl]-2-hexyl-2,3,4,9-tetrahydro-1H-carbazole-8-carboxylic acid, 2-hexyl-9-[(4-methylphenyl)methyl]-2,3,4,9-tetrahydro-1H-carbazole-8-carboxylic acid, 9-[(4-cyanophenyl)methyl]-2-hexyl-2,3,4,9-tetrahydro-1H-carbazole-8-carboxylic acid, 9-[(2-cyanophenyl)methyl]-2-hexyl-2,3,4,9-tetrahydro-1H-carbazole-8-carboxylic acid, 2-hexyl-9-[(2-methylphenyl)methyl]-2,3,4,9-tetrahydro-1H-carbazole-8-carboxylic acid, 9-[(2-fluorophenyl)methyl]-2-hexyl-2,3,4,9-tetrahydro-1H-carbazole-8-carboxylic acid, 9-[(3-carbamoylphenyl)methyl]-2-(2-phenylethyl)-2,3,4,9-tetrahydro-1H-carbazole-8-carboxylic acid, 9-[(3-cyanophenyl)methyl]-2-(2-phenylethyl)-2,3,4,9-tetrahydro-1H-carbazole-8-carboxylic acid, 9-[(3-carbamoylphenyl)methyl]-4-(2-phenylethyl)-2,3,4,9-tetrahydro-1H-carbazole-8-carboxylic acid, 9-[(3-cyanophenyl)methyl]-4-(2-phenylethyl)-2,3,4,9-tetrahydro-1H-carbazole-8-carboxylic acid, 9-[(3-carbamoylphenyl)methyl]-2-propyl-2,3,4,9-tetrahydro-1H-carbazole-8-carboxylic acid, 9-[(3-cyanophenyl)methyl]-2-propyl-2,3,4,9-tetrahydro-1H-carbazole-8-carboxylic acid, 2-butyl-9-[(3-carbamoylphenyl)methyl]-2,3,4,9-tetrahydro-1H-carbazole-8-carboxylic acid, 9-[(3-carbamoylphenyl)methyl]-2-pentyl-2,3,4,9-tetrahydro-1H-carbazole-8-carboxylic acid, 9-[(3-cyanophenyl)methyl]-2-pentyl-2,3,4,9-tetrahydro-1H-carbazole-8-carboxylic acid, 1-butyl-9-[(3-carbamoylphenyl)methyl]-2,3,4,9-tetrahydro-1H-carbazole-8-carboxylic acid, 9-[(3-carbamoylphenyl)methyl]-1-(pentyloxy)-2,3,4,9-tetrahydro-1H-carbazole-8-carboxylic acid, 9-[(3-cyanophenyl)methyl]-1-(pentyloxy)-2,3,4,9-tetrahydro-1H-carbazole-8-carboxylic acid, 1-butyl-9-[(3-cyanophenyl)methyl]-2,3,4,9-tetrahydro-1H-carbazole-8-carboxylic acid, 6-butyl-5-[(3-carbamoylphenyl)methyl]-5H,6H,7H,8H,9H, 10H-cyclohepta[b]indole-4-carboxylic acid, 6-butyl-5-[(3-cyanophenyl)methyl]-5H,6H,7H,8H,9H,10H-cyclohepta[b]indole-4-carboxylic acid, 9-[(3-carbamoylphenyl)methyl]-1-ethyl-2,3,4,9-tetrahydro-1H-carbazole-8-carboxylic acid, 9-[(3-cyanophenyl)methyl]-1-ethyl-2,3,4,9-tetrahydro-1H-carbazole-8-carboxylic acid, 9-[(3-carboxyphenyl)methyl]-1-ethyl-2,3,4,9-tetrahydro-1H-carbazole-8-carboxylic acid, 9-[(3-carbamoylphenyl)methyl]-1-propoxy-2,3,4,9-tetrahydro-1H-carbazole-8-carboxylic acid, 9-[(3-carbamoylphenyl)methyl]-4-ethyl-2,3,4,9-tetrahydro-1H-carbazole-8-carboxylic acid, 4-[(3-carbamoylphenyl)methyl]-3-ethyl-1H,2H,3H,4H-cyclopenta[b]indole-5-carboxylic acid, 4-[(3-cyanophenyl)methyl]-3-ethyl-1H,2H,3H,4H-cyclopenta[b]indole-5-carboxylic acid, 3-butyl-4-[(3-carbamoylphenyl)methyl]-1H,2H,3H,4H-cyclopenta[b]indole-5-carboxylic acid, 3-butyl-4-[(3-cyanophenyl)methyl]-1H,2H,3H,4H-cyclopenta[b]indole-5-carboxylic acid, 2-butyl-4-[(3-carbamoylphenyl)methyl]-1H,2H,3H,4H-cyclopenta[b]indole-5-carboxylic acid, 2-butyl-4-[(3-cyanophenyl)methyl]-1H,2H,3H,4H-cyclopenta[b]indole-5-carboxylic acid, 5-[(3-carbamoylphenyl)methyl]-10-ethyl-5H,6H,7H,8H,9H,10H-cyclohepta[b]indole-4-carboxylic acid, 5-[(3-cyanophenyl)methyl]-10-ethyl-5H,6H,7H,8H,9H,10H-cyclohepta[b]indole-4-carboxylic acid, 5-[(3-carbamoylphenyl)methyl]-10-propyl-5H,6H,7H,8H,9H,10H-cyclohepta[b]indole-4-carboxylic acid, 5-[(3-cyanophenyl)methyl]-10-propyl-5H,6H, 7H, 8H,9H, 10H-cyclohepta[b]indole-4-carboxylic acid, 9-[(3-carboxyphenyl)methyl]-4-ethyl-2,3,4,9-tetrahydro-1H-carbazole-8-carboxylic acid, 9-[(3-carbamoylphenyl)methyl]-3-ethyl-2,3,4,9-tetrahydro-1H-carbazole-8-carboxylic acid, 10-butyl-5-[(3-carbamoylphenyl)methyl]-5H,6H,7H,8H,9H,10H-cyclohepta[b]indole-4-carboxylic acid, 10-butyl-5-[(3-cyanophenyl)methyl]-5H,6H,7H,8H,9H,10H-cyclohepta[b]indole-4-carboxylic acid, 5-[(3-carbamoylphenyl)methyl]-10-pentyl-5H,6H,7H,8H,9H, 10H-cyclohepta[b]indole-4-carboxylic acid, 5-[(3-cyanophenyl)methyl]-10-pentyl-5H,6H,7H,8H,9H, 10H-cyclohepta[b]indole-4-carboxylic acid, 4-[(3-carbamoylphenyl)methyl]-2-pentyl-1H,2H,3H,4H-cyclopenta[b]indole-5-carboxylic acid, 4-[(3-cyanophenyl)methyl]-2-pentyl-1H,2H,3H,4H-cyclopenta[b]indole-5-carboxylic acid, 9-[(3-carbamoylphenyl)methyl]-2-ethyl-2,3,4,9-tetrahydro-1H-carbazole-8-carboxylic acid, 9-[(3-carboxyphenyl)methyl]-2-ethyl-2,3,4,9-tetrahydro-1H-carbazole-8-carboxylic acid, 5-[(3-carbamoylphenyl)methyl]-7-ethyl-5H,6H, 7H, 8H,9H, 10H-cyclohepta[b]indole-4-carboxylic acid, 5-[(3-cyanophenyl)methyl]-7-ethyl-5H,6H,7H,8H,9H,10H-cyclohepta[b]indole-4-carboxylic acid, 9-[(3-cyanophenyl)methyl]-3-ethyl-2,3,4,9-tetrahydro-1H-carbazole-8-carboxylic acid, 9-[(3-carbamoylphenyl)methyl]-4-propyl-2,3,4,9-tetrahydro-1H-carbazole-8-carboxylic acid, 9-[(3-carbamoylphenyl)methyl]-3-propyl-2,3,4,9-tetrahydro-1H-carbazole-8-carboxylic acid, 9-[(3-cyanophenyl)methyl]-3-propyl-2,3,4,9-tetrahydro-1H-carbazole-8-carboxylic acid, 4-butyl-9-[(3-carbamoylphenyl)methyl]-2,3,4,9-tetrahydro-1H-carbazole-8-carboxylic acid, 4-butyl-9-[(3-cyanophenyl)methyl]-2,3,4,9-tetrahydro-1H-carbazole-8-carboxylic acid, 3-butyl-9-[(3-carbamoylphenyl)methyl]-2,3,4,9-tetrahydro-1H-carbazole-8-carboxylic acid, 3-butyl-9-[(3-cyanophenyl)methyl]-2,3,4,9-tetrahydro-1H-carbazole-8-carboxylic acid, 9-[(3-carbamoylphenyl)methyl]-4-pentyl-2,3,4,9-tetrahydro-1H-carbazole-8-carboxylic acid, 9-[(3-cyanophenyl)methyl]-4-pentyl-2,3,4,9-tetrahydro-1H-carbazole-8-carboxylic acid, 9-[(3-carbamoylphenyl)methyl]-3-pentyl-2,3,4,9-tetrahydro-1H-carbazole-8-carboxylic acid, 9-[(3-cyanophenyl)methyl]-3-pentyl-2,3,4,9-tetrahydro-1H-carbazole-8-carboxylic acid, 4-[(3-carbamoylphenyl)methyl]-3-propyl-1H,2H,3H,4H-cyclopenta[b]indole-5-carboxylic acid, 4-[(3-cyanophenyl)methyl]-3-propyl-1H,2H,3H,4H-cyclopenta[b]indole-5-carboxylic acid, 2-({7-butyl-5-[(3-carbamoylphenyl)methyl]-5H,6H,7H,8H,9H,10H-cyclohepta[b]indol-4-yl}formamido)acetic acid, 2-({7-butyl-5-[(3-cyanophenyl)methyl]-5H,6H,7H,8H,9H,10H-cyclohepta[b]indol-4-yl}formamido)acetic acid, 7-butyl-5-[(3-carbamoylphenyl)methyl]-N-(2-hydroxyethyl)-5H,6H,7H,8H,9H, 10H-cyclohepta[b]indole-4-carboxamide, 7-butyl-5-[(3-cyanophenyl)methyl]-N-(2-hydroxyethyl)-5H,6H,7H,8H,9H,10H-cyclohepta[b]indole-4-carboxamide, 7-butyl-5-[(3-fluorophenyl)methyl]-5H,6H,7H,8H,9H,10H-cyclohepta[b]indole-4-carboxylic acid, and 7-butyl-5-[(3-carboxyphenyl)methyl]-5H,6H,7H,8H,9H,10H-cyclohepta[b]indole-4-carboxylic acid, or pharmaceutically acceptable salts or stereoisomers thereof.

31. A compound according to claim 30 which is a pure optical isomer.

32. A method of inhibiting the fatty acid binding protein FABP4 in a mammal, which comprises administering to a mammal an effective amount of a compound of claim 1.

33. A method according to claim 32, wherein the subject is a human.

34. The compound according to claim 1 for use in the prophylaxis or treatment of disorders acting on the fatty acid binding protein FABP4.

35. The compound according to claim 34, wherein the disorders are selected from type 2 diabetes, hyperglycemia, metabolic syndrome, obesity, atherosclerosis, intracranial atherosclerotic disease, non-alcoholic steatohepatitis, asthma, vascular dementia, multiple sclerosis, Alzheimer's disease, other chronic inflammatory and autoimmune/inflammatory diseases, chronic heart disease, polycystic ovary syndrome, preeclampsia, and cancer.

36. A pharmaceutical composition comprising a compound according to claim 1 as the active ingredient, in combination with a pharmaceutically acceptable diluent or carrier.

37. The pharmaceutical composition of claim 36, for use in the prophylaxis or treatment of disorders acting on the fatty acid binding protein FABP4.

38. The pharmaceutical composition according to claim 37, wherein the disorders are selected from type 2 diabetes, hyperglycemia, metabolic syndrome, obesity, atherosclerosis, intracranial atherosclerotic disease, non-alcoholic steatohepatitis, asthma, vascular dementia, multiple sclerosis, Alzheimer's disease, other chronic inflammatory and autoimmune/inflammatory diseases, chronic heart disease, polycystic ovary syndrome, preeclampsia, and cancer.

39. The pharmaceutical composition according to claim 37, further comprising an additional therapeutically active agent.

40. A method for the prophylaxis or treatment of disorders acting on the fatty acid binding protein FABP4, which comprises administering to a subject in need of such treatment an effective amount of a compound according to claim 1.

41. A method according to claim 40, wherein the subject is a human.

42. The method according to claim 40, wherein the disorders are selected from type 2 diabetes, hyperglycemia, metabolic syndrome, obesity, atherosclerosis, intracranial atherosclerotic disease, non-alcoholic steatohepatitis, asthma, vascular dementia, multiple sclerosis, Alzheimer's disease, other chronic inflammatory and autoimmune/inflammatory diseases, chronic heart disease, polycystic ovary syndrome, preeclampsia, and cancer.

43. A method for inhibiting FABP4, which comprises administering to a subject in need of such treatment an effective amount of a compound according to claim 1.

44. A method according to claim 43, wherein the subject is a human.

\* \* \* \* \*